(12) United States Patent
Okumura et al.

(10) Patent No.: US 11,773,207 B2
(45) Date of Patent: Oct. 3, 2023

(54) THIOL COMPOUND, METHOD FOR SYNTHESIZING SAME, AND USES FOR SAID THIOL COMPOUND

(71) Applicant: SHIKOKU CHEMICALS CORPORATION, Kagawa (JP)

(72) Inventors: Naoto Okumura, Kagawa (JP); Yusuke Araki, Kagawa (JP); Takeshi Kumano, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 217 days.

(21) Appl. No.: 17/421,139

(22) PCT Filed: Dec. 23, 2019

(86) PCT No.: PCT/JP2019/050360
§ 371 (c)(1),
(2) Date: Jul. 7, 2021

(87) PCT Pub. No.: WO2020/145111
PCT Pub. Date: Jul. 16, 2020

(65) Prior Publication Data
US 2022/0112330 A1  Apr. 14, 2022

(30) Foreign Application Priority Data
Jan. 7, 2019  (JP) .................. 2019-000860

(51) Int. Cl.
*C08G 59/66*   (2006.01)
*C07C 319/18*  (2006.01)
(Continued)

(52) U.S. Cl.
CPC ............ *C08G 59/66* (2013.01); *C07C 319/18* (2013.01); *C07C 323/12* (2013.01);
(Continued)

(58) Field of Classification Search
None
See application file for complete search history.

(56) References Cited

U.S. PATENT DOCUMENTS 5,288,844 A   2/1994  Sakagami
5,430,112 A   7/1995  Sakata et al.
(Continued)

FOREIGN PATENT DOCUMENTS

| CN | 1166168 | 11/1997 |
| JP | 2-38418 | 2/1990 |

(Continued)

OTHER PUBLICATIONS

International Search Report dated Mar. 24, 2020 in International (PCT) Application No. PCT/JP2019/050360, with English translation.

(Continued)

*Primary Examiner* — Megan Mcculley
(74) *Attorney, Agent, or Firm* — Wenderoth, Lind & Ponack, L.L.P.

(57) ABSTRACT

An objective of the present invention is to provide: a novel thiol compound; a method for synthesizing the thiol compound; a curing agent containing the thiol compound; a resin composition containing the thiol compound and an epoxy compound; and a resin composition containing the thiol compound and an enic compound having an intramolecular carbon-carbon double bond. The thiol compound of the present invention, as exemplified by the compounds listed below, is a reaction product of a certain type of dialkene compound and a thiol compound, and has two or more intramolecular thioether bonds but no ester bonds.

(Continued)

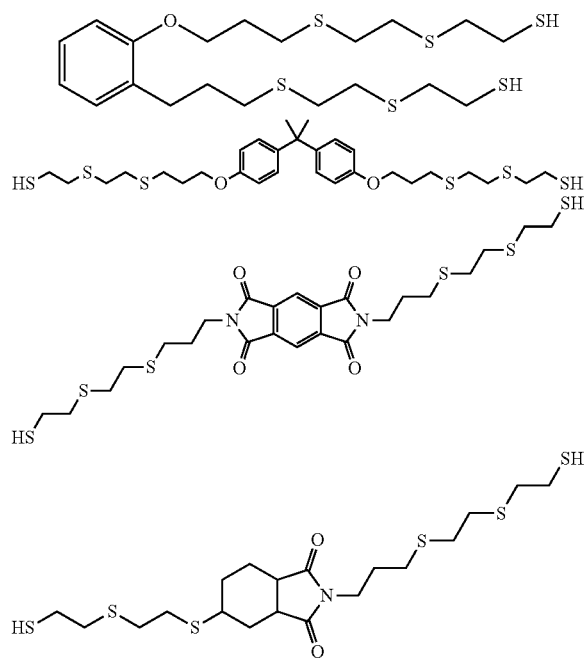

12 Claims, 10 Drawing Sheets

(51) Int. Cl.
| | |
|---|---|
| C07C 323/12 | (2006.01) |
| C07C 323/19 | (2006.01) |
| C07D 233/70 | (2006.01) |
| C07D 235/02 | (2006.01) |
| C07D 235/26 | (2006.01) |
| C07D 495/04 | (2006.01) |
| C09J 4/00 | (2006.01) |
| C09J 163/00 | (2006.01) |

(52) U.S. Cl.
CPC .......... *C07C 323/19* (2013.01); *C07D 233/70* (2013.01); *C07D 235/02* (2013.01); *C07D 235/26* (2013.01); *C07D 495/04* (2013.01); *C09J 4/00* (2013.01); *C09J 163/00* (2013.01)

(56) References Cited

U.S. PATENT DOCUMENTS

| | | | |
|---|---|---|---|
| 5,834,621 A | 11/1998 | Yamamoto et al. | |
| 2003/0166808 A1 | 9/2003 | Okazaki et al. | |
| 2012/0286435 A1* | 11/2012 | Bojkova | B29B 7/74 264/1.1 |
| 2013/0344340 A1* | 12/2013 | Senkfor | C08G 18/12 428/419 |
| 2016/0289237 A1 | 10/2016 | Kumano et al. | |
| 2017/0114208 A1* | 4/2017 | Rao | C08L 81/04 |
| 2019/0169465 A1* | 6/2019 | Virnelson | C09J 175/14 |
| 2020/0369606 A1 | 11/2020 | Okumura et al. | |

FOREIGN PATENT DOCUMENTS

| | | |
|---|---|---|
| JP | 5-32724 | 2/1993 |
| JP | 5-155798 | 6/1993 |
| JP | 6-211969 | 8/1994 |
| JP | 6-211970 | 8/1994 |
| JP | 9-59248 | 3/1997 |
| JP | 10-330450 | 12/1998 |
| JP | 11-125701 | 5/1999 |
| JP | 2007-332091 | 12/2007 |
| JP | 2009-73809 | 4/2009 |
| JP | 2014-058667 | 4/2014 |
| JP | 2016-164134 | 9/2016 |
| JP | 2019-85403 | 6/2019 |
| TW | 201529577 | 8/2015 |
| WO | 97/19964 | 6/1997 |
| WO | 02/36662 | 5/2002 |
| WO | 2011-78060 | 6/2011 |
| WO | 2013/114987 | 8/2013 |

OTHER PUBLICATIONS

Written Opinion of the International Searching Authority dated Mar. 24, 2020 in International (PCT) Application No. PCT/JP2019/050360, with English translation.

Kornblum et al., "Heterogeneity as a Factor in the Alkylation of Ambident Anions: Phenoxide Ions", J. Am. Chem. Soc., 1959, vol. 81, pp. 2705-2715.

Bhattacharjee et al., "Oxamidation of Unsaturated O-Alkyl Hydroxamates: Synthesis of the Madangamine Diazatricylic (ABC Rings) Skeleton", Organic Letters, 2017, vol. 19, pp. 6570-6573.

Agar et al., "Synthesis and Characterization of New Phthalocyanines Containing Four 15-Membered Tetrathiaoxa Macrocycles", Synthesis and Reactivity in Inorganic and Metal-Organic Chemistry, 1999. vol. 3, No. 29, pp. 473-485.

Clark et al., "Synthesis of Some Substituted Benzimidazolones", J. Am. Chem. Soc., 1958, vol. 80, pp. 1657-1662.

Kolodzluk et al., "An Easy and Efficient Access to Bis-Allyloxy-Arenes", Synthetic Communication, 2000, vol. 30, pp. 3955-3961.

Office Action dated Nov. 11, 2022 in Chinese Application No. 201980088293.4, with English translation thereof.

Notification of Reasons for Refusal dated Oct. 31, 2022 in Japanese Application No. 2019-000860, with English translation thereof.

Office Action dated Aug. 31, 2022 in Taiwanese Application No. 108147888, with English translation thereof.

Office Action dated May 25, 2023 in corresponding Chinese Patent Application No. 201980088293.4, with English-language translation.

\* cited by examiner

THIOL COMPOUND, METHOD FOR SYNTHESIZING SAME, AND USES FOR SAID THIOL COMPOUND

TECHNICAL FIELD

The present invention relates to a novel thiol compound, a synthesis method of the thiol compound, and utilization of the thiol compound.

BACKGROUND ART

Compounds having a plurality of thiol groups in the molecule (hereinafter, may be referred to as a polythiol compound) have been known as a curing agent of an epoxy compound (note: epoxy resin before curing).

For example, Patent Literature 1 proposes an epoxy resin composition using a polythiol compound as a curing agent and also containing a reaction product between an amine and an epoxy compound as a curing accelerator. The epoxy resin composition is said to have a long pot life and additionally be promptly cured at relatively low temperature.

[Chem. 1]

Patent Literature 2 proposes an epoxy resin composition containing, as a curing accelerator, a reaction product between an isocyanate compound having one or more isocyanate groups in the molecule and a compound having at least one primary and/or secondary amino group in the molecule. The epoxy resin composition is also said to have a long pot life and have excellent curability.

Further, the polythiol compounds and enic compounds having a carbon-carbon double bond in the molecule are promptly polymerized (cured) by a polymerization initiator, and therefore utilization thereof in various uses is being considered.

For example, Patent Literature 3 discloses that tris[(3-mercaptopropanoyloxy)-ethyl]isocyanurate having three thiol groups in the molecule as a thiol compound is promptly reacted with an enic compound to provide a cured product having excellent properties.

However, those thiol compounds have an ester bond in the molecule. As a result, there is a problem on moisture resistance of the cured product obtained since the ester bond is hydrolyzed under humidification conditions.

In addition to those patent literatures, the following Patent Literatures 4 and 5 are listed as literatures describing inventions relating to the present invention.

The invention described in Patent Literature 4 relates to a polythiol compound for curing an epoxy resin.

This literature discloses tris(9-mercapto-4,7-dithianonyl)isocyanurate (see chemical formula (II)) as an example of the polythiol compound, and discloses that this polythiol compound is a reaction product using triallyl isocyanurate and 1,5-dimercapto-3-thiapentane (corresponding to 3-thiapentane-1,5-dithiol described later) as raw materials.

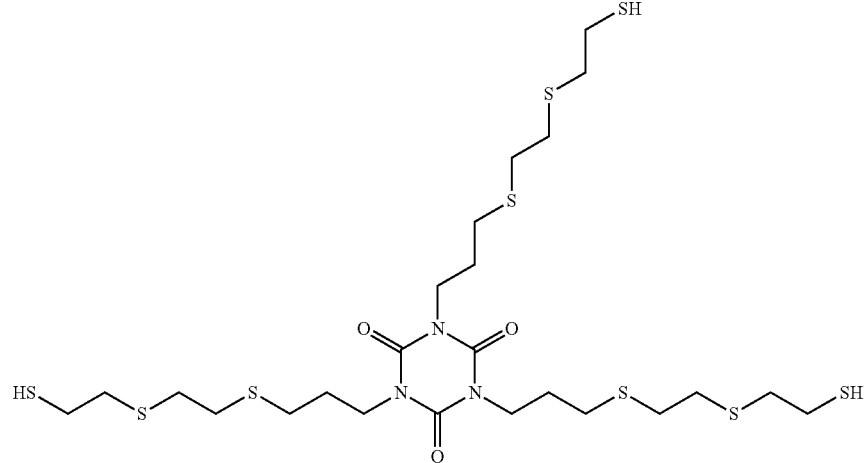

The invention described in Patent Literature 5 relates to glycoluril having a thioether bond and a mercapto group and utilization thereof.

This literature discloses 1,3,4,6-tetrakis{3-[2-(2-mercaptoethylsulfanyl)ethylsulfanyl]propyl}glycoluril (see chemical formula (III)) as an example of glycoluril compounds that are expected to be used as the curing agent for an epoxy resin, and discloses that this glycoluril compound is an reaction product using 1,3,4,6-tetraallyl glycoluril and bis(2-mercaptoethyl) sulfide (corresponding to 3-thiapentane-1,5-dithiol described later) as raw materials.

[Chem. 2]

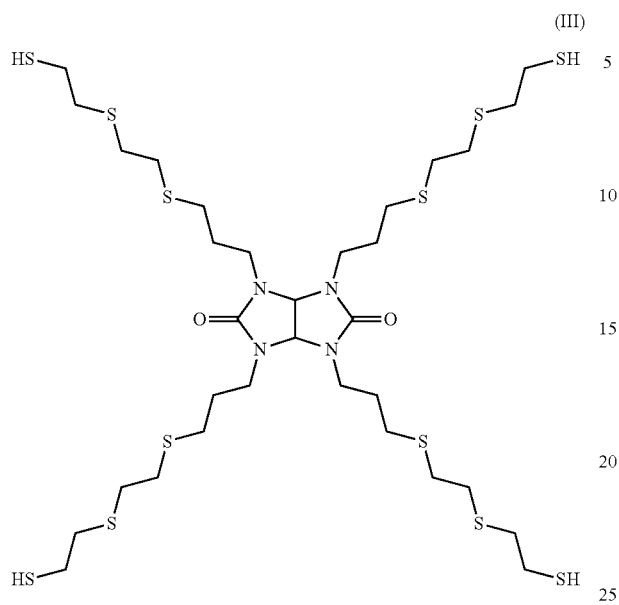

(III)

CITATION LIST

Patent Literature

Patent Literature 1: JP-A-H06-211969
Patent Literature 2: JP-A-H06-211970
Patent Literature 3: JP-A-2014-58667
Patent Literature 4: JP-A-H02-38418
Patent Literature 5: JP-A-2016-164134

SUMMARY OF INVENTION

Technical Problem

An object of the present invention is to provide a novel thiol compound, a synthesis method of the thiol compound, a curing agent containing the thiol compound, a resin composition containing the thiol compound and an epoxy compound, and a resin composition containing the thiol compound and an enic compound having a carbon-carbon double bond in the molecule.

Another object is to provide an adhesive and a sealant containing the above-mentioned resin composition as a component.

Solution to Problem

As a result of extensive investigations for solving the above-described problems, the present inventors have found that the intended objects can be achieved by using a reaction product between a certain dialkene compound and a certain thiol compound. Thus, the present invention has been completed.

That is a first invention is a thiol compound represented by the chemical formula (I).

[Chem. 3]

Y-A-Y   (I)

(In the chemical formula (I), A represents a divalent group represented by any one of the chemical formula (A-1) to the chemical formula (A-23), and Y's each represent a group represented by the chemical formula (Y).)

[Chem. 4]

(A-1)

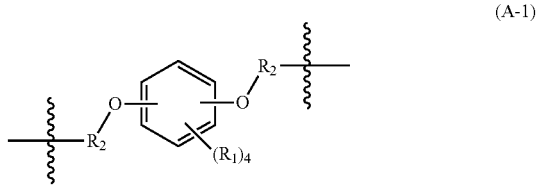
(A-2)

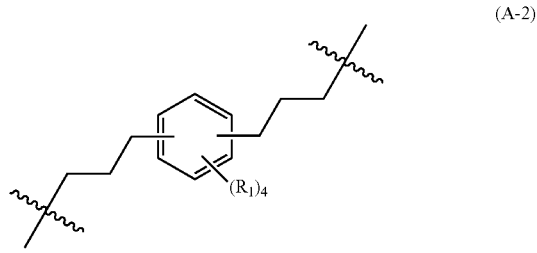
(A-3)

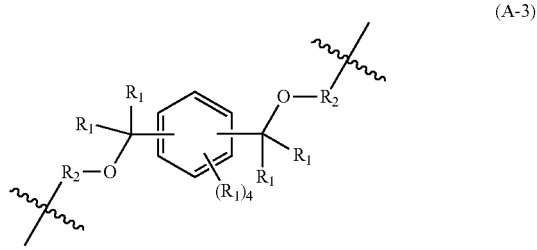
(A-4)

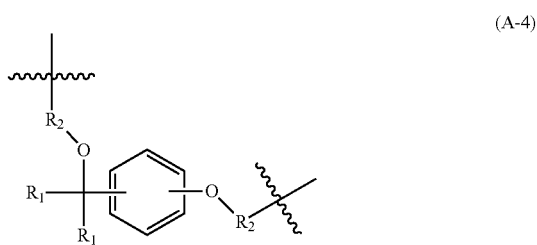
(A-5)

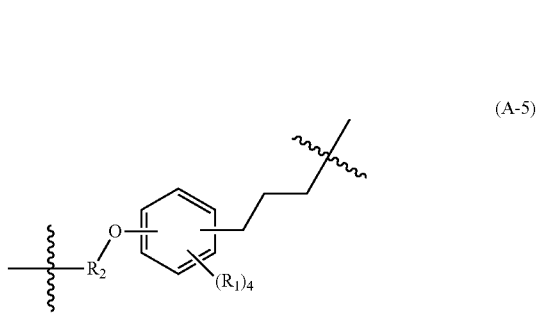
(A-6)

-continued
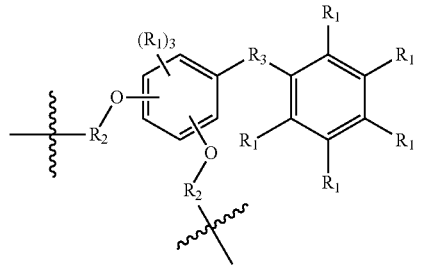
(A-7)
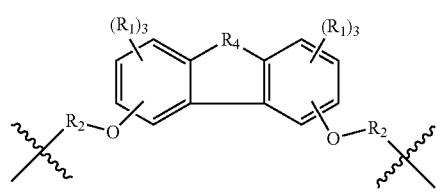
(A-8)
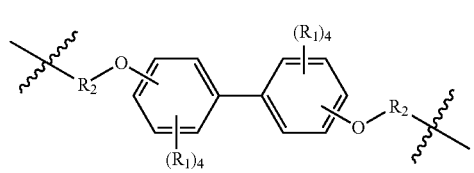
(A-9)
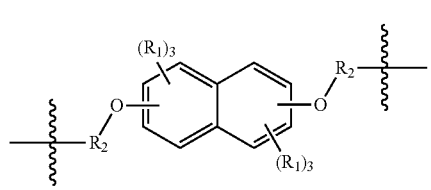
(A-10)
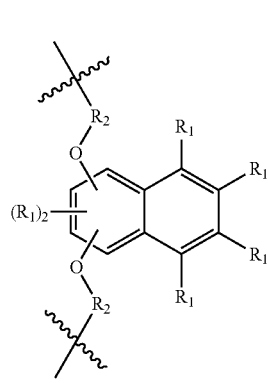
(A-11)
[Chem. 5]
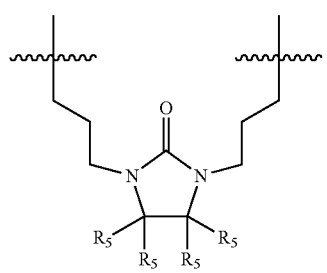
(A-12)
-continued
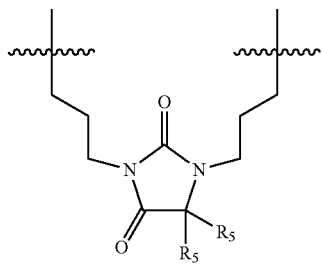
(A-13)
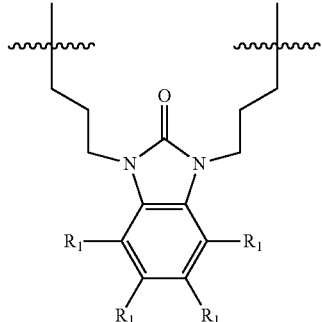
(A-14)
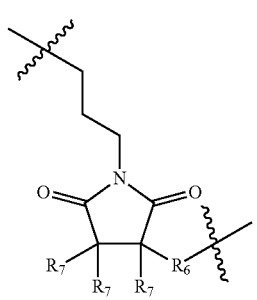
(A-15)
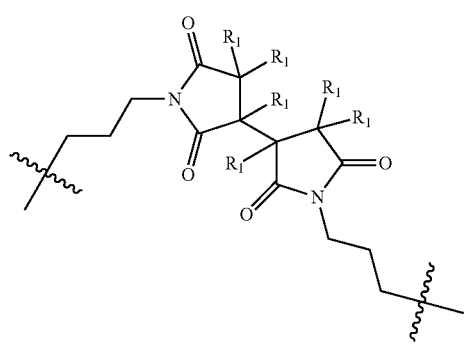
(A-16)
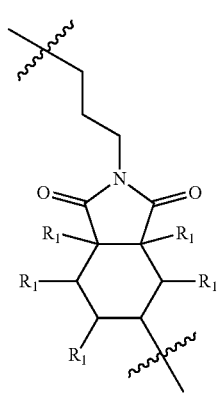
(A-17)

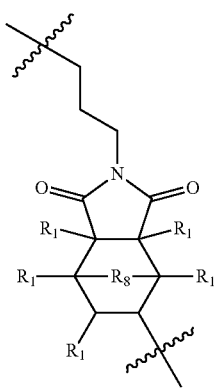
(A-18)

[Chem. 6]

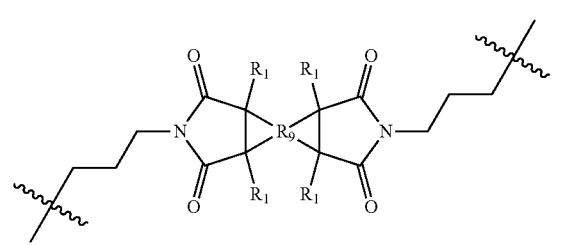
(A-19)

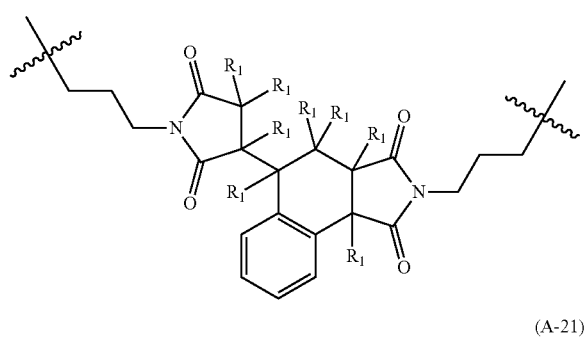
(A-20)

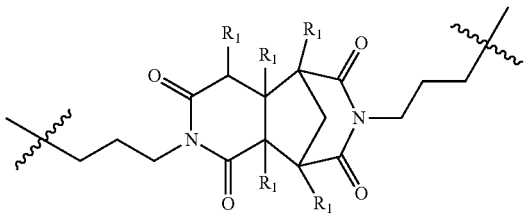
(A-21)

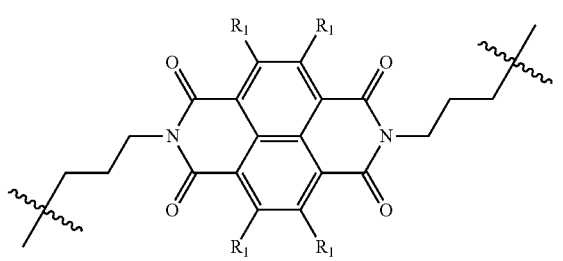
(A-22)

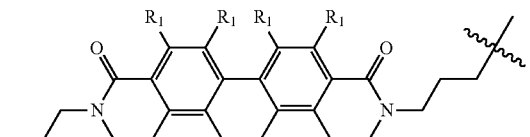
(A-23)

[Chem. 7]

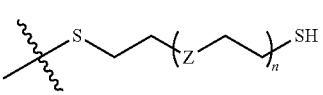
(Y)

(In the chemical formula (A-1) to the chemical formula (A-23), $R_1$'s are the same as or different from each other and each represent a hydrogen atom, a linear, branched or cyclic alkyl group or alkoxy group having 1 to 10 carbon atoms, or an aryl group, $R_2$'s are the same as or different from each other and each represent a divalent group represented by any one of the chemical formula (R2-1) to the chemical formula (R2-4), $R_3$ represents a divalent group represented by any one of the chemical formula (R3-1) to the chemical formula (R3-12), $R_4$ represents a divalent group represented by any one of the chemical formula (R3-1) to the chemical formula (R3-4), the chemical formula (R3-6) or any one of the chemical formula (R3-8) to the chemical formula (R3-12), $R_5$'s are the same as or different from each other and each represent a hydrogen atom, a linear, branched or cyclic alkyl group having 1 to 10 carbon atoms, $R_6$ represents an atomic bonding (a bond), or a divalent group represented by the chemical formula (R3-1) or any one of the chemical formula (R6-1) to the chemical formula (R6-6), $R_7$'s are the same as or different from each other and each represent a hydrogen atom, a linear, branched or cyclic alkyl group having 1 to 10 carbon atoms, or an aryl group, R7's may be linked to each other to form a ring, $R_8$ represents a divalent group represented by the chemical formula (R3-1), the chemical formula (R3-10) or the chemical formula (R8-1), and $R_9$ represents a tetravalent group represented by any one of the chemical formula (R9-1) to the chemical formula (R9-15).

In the chemical formula (Y), Z's represent the same as or different from each other, and each represent an oxygen atom or a sulfur atom, and n represents an integer of 1 to 3.

The wavy line portions in the chemical formula (A-1) to the chemical formula (A-23) and the chemical formula (Y) each represent an atomic bonding.)

[Chem. 8]

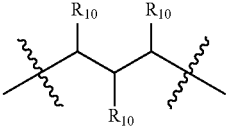
(R2-1)

-continued (R2-2)
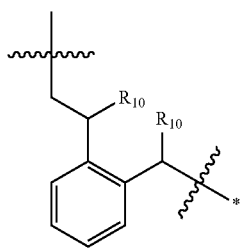

(R2-3)
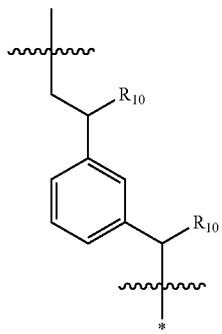

(R2-4)
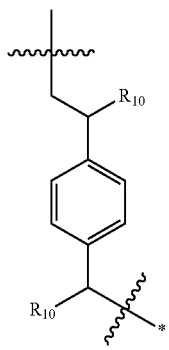

(In the chemical formula (R2-1) to the chemical formula (R2-4), $R_{10}$'s are the same as or different from each other and each represent a hydrogen atom or a methyl group. The wavy line portions each represent an atomic bonding, and those with * (asterisk) each represent a bond to an oxygen atom.)

[Chem. 9]

(R3-1)

(R3-2)
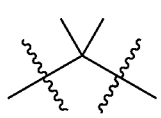

(R3-3)
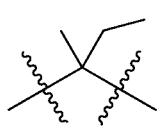

(R3-4)
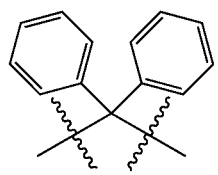

(R3-5)
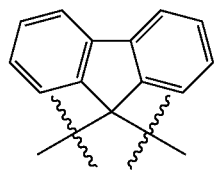

(R3-6)
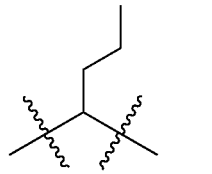

(R3-7)
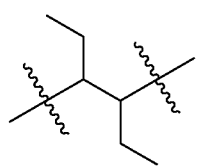

(R3-8)
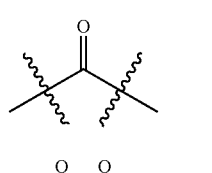

(R3-9)
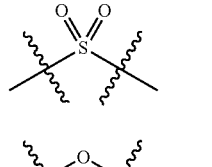

(R3-10)
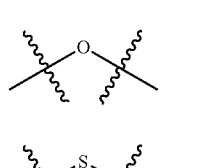

(R3-11)
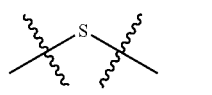

(R3-12)
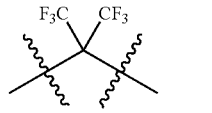

(In the chemical formula (R3-1) to the chemical formula (R3-12), the wavy line portions each represent an atomic bonding.)

[Chem. 10]

(R6-1)
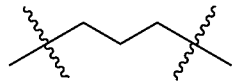

-continued
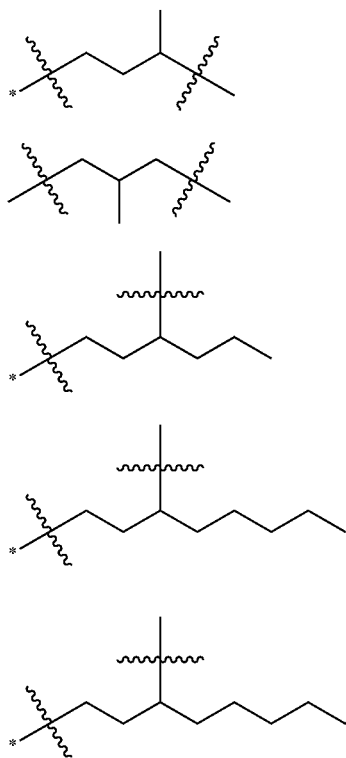
(R6-2)
(R6-3)
(R6-4)
(R6-5)
(R6-6)
(In the chemical formula (R6-1) to the chemical formula (R6-6), the wavy line portions each represent an atomic bonding, and those with * (asterisk) each represent a bond to an imide ring.)
[Chem. 11]
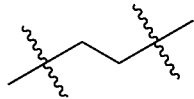
(R8-1)
(In the chemical formula (R8-1), the wavy line portions each represent an atomic bonding.)
[Chem. 12]
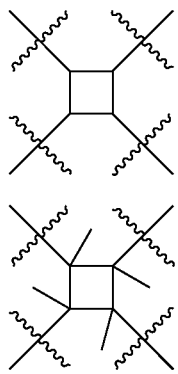
(R9-1)
(R9-2)
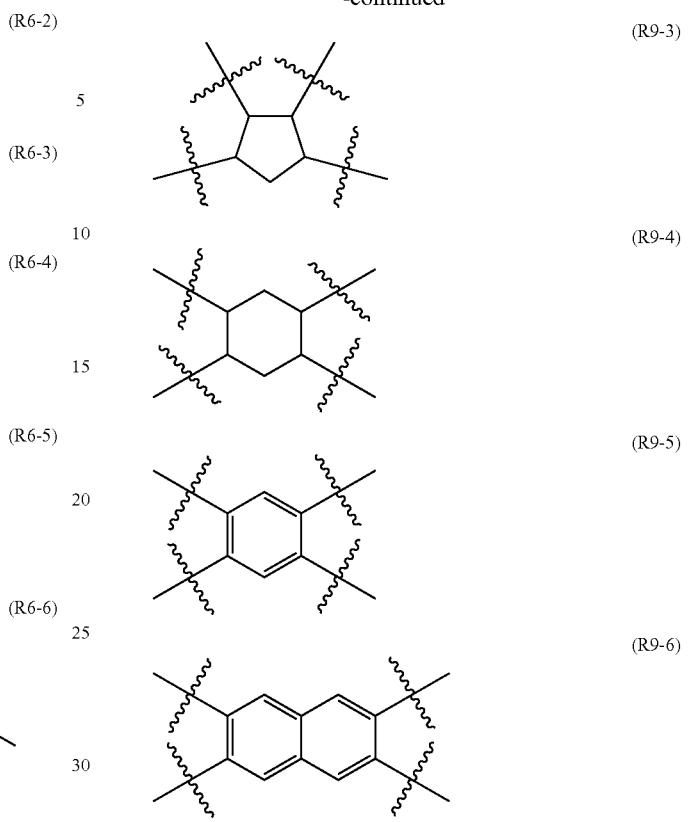
(R9-3)
(R9-4)
(R9-5)
(R9-6)
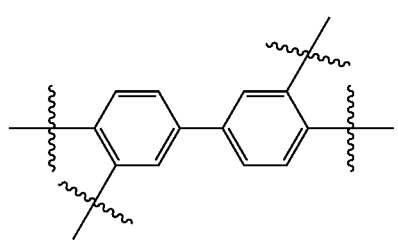
(R9-7)
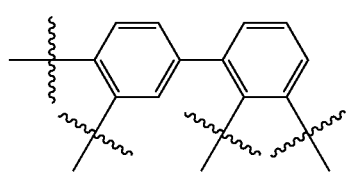
(R9-8)
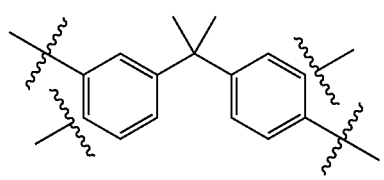
(R9-9)
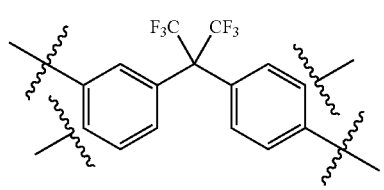
(R9-10)

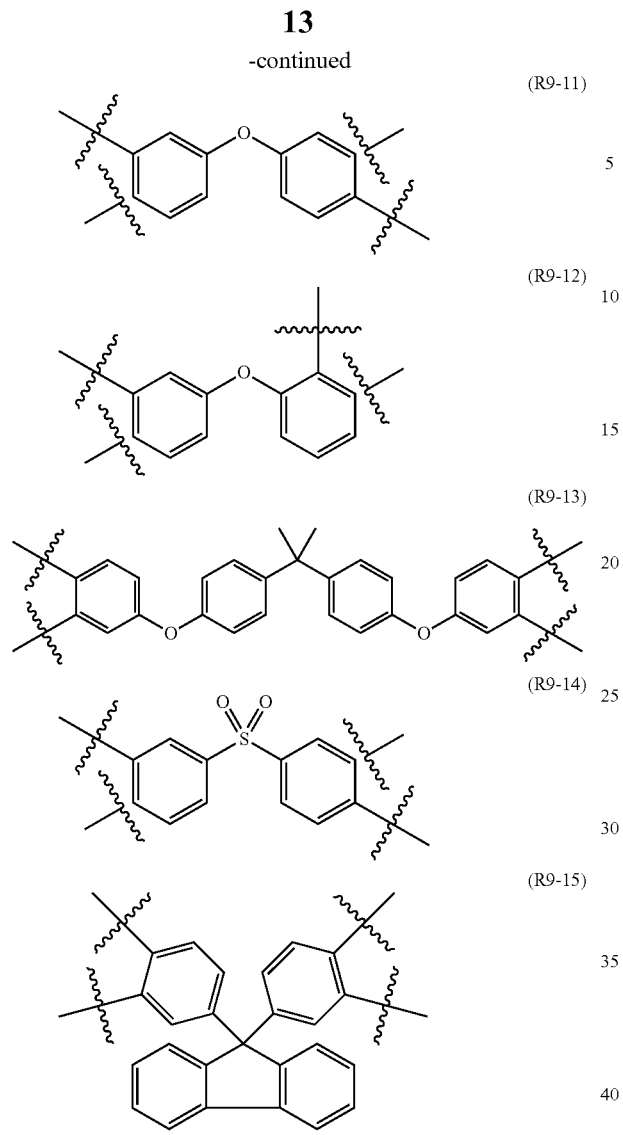

(In the chemical formula (R9-1) to the chemical formula (R9-15), the wavy line portions each represent an atomic bonding.)

A second invention is a synthesis method of the thiol compound of the first invention, including: reacting a dialkene compound represented by any one of the chemical formula (B-1) to the chemical formula (B-23) with a thiol compound represented by any one of the chemical formula (C-1) to the chemical formula (C-11).

[Chem. 13]

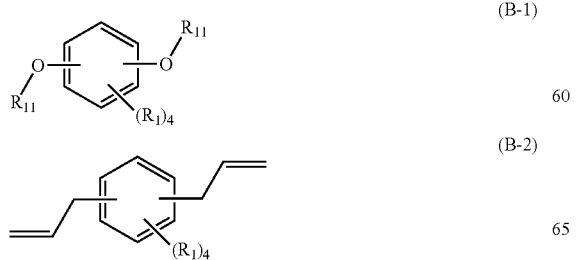

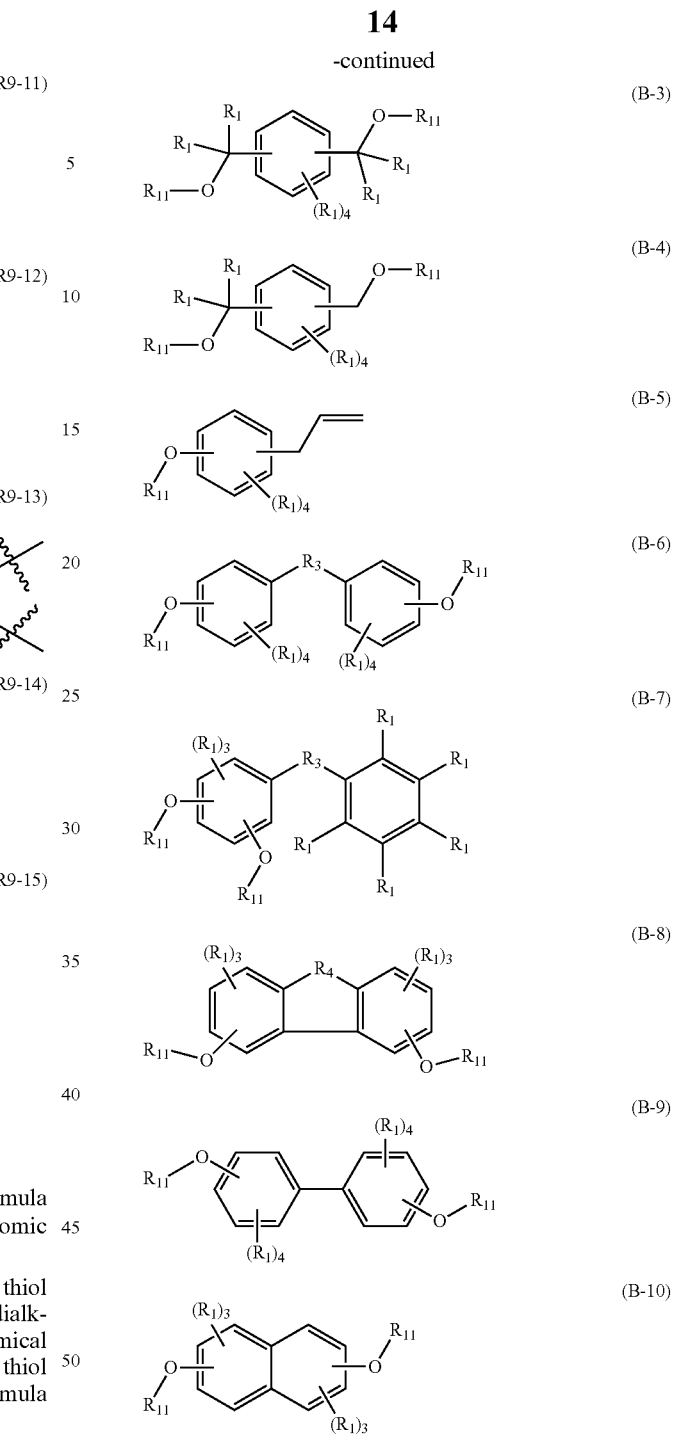

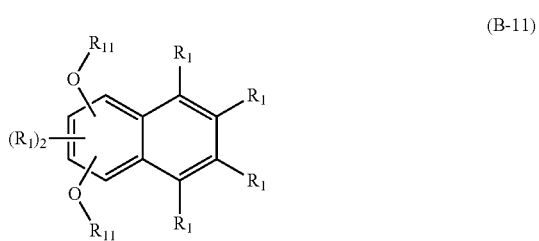

[Chem. 14]
(B-12) 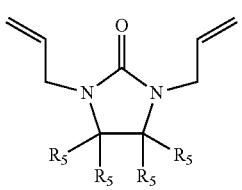
(B-13) 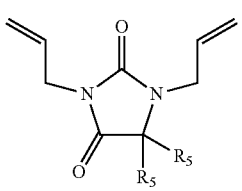
(B-14) 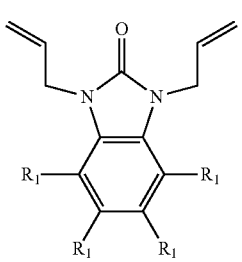
(B-15a) 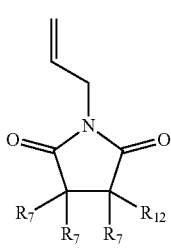
(B-15b) 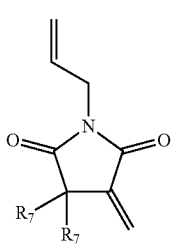
(B-15c) 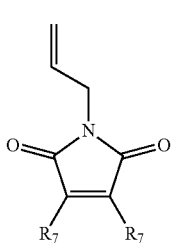
(B-16) 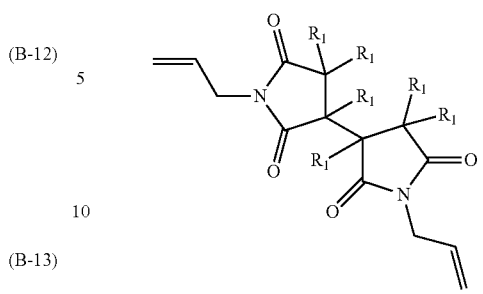
(B-17) 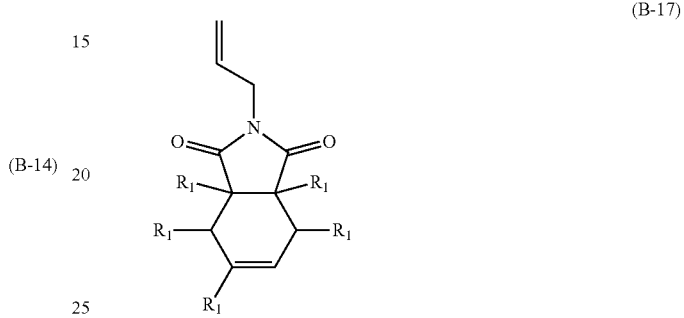
(B-18) 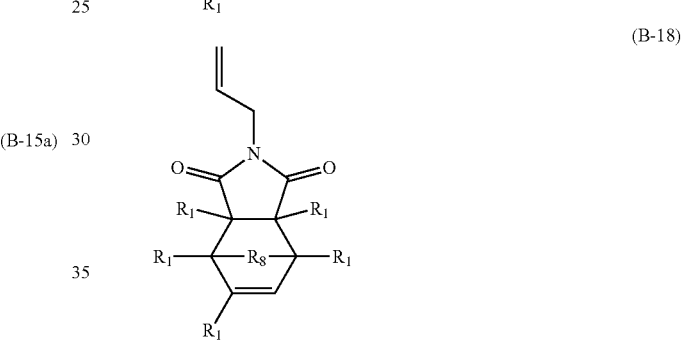
[Chem. 15]
(B-19) 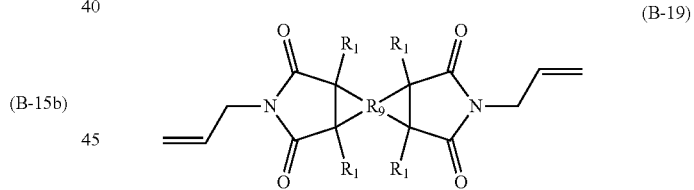
(B-20) 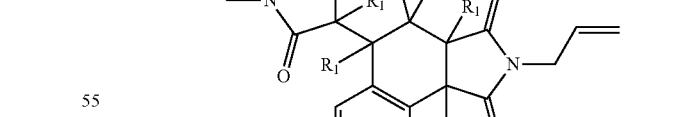
(B-21) 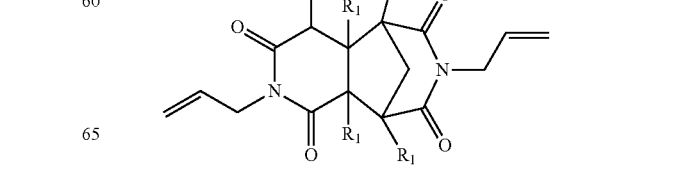

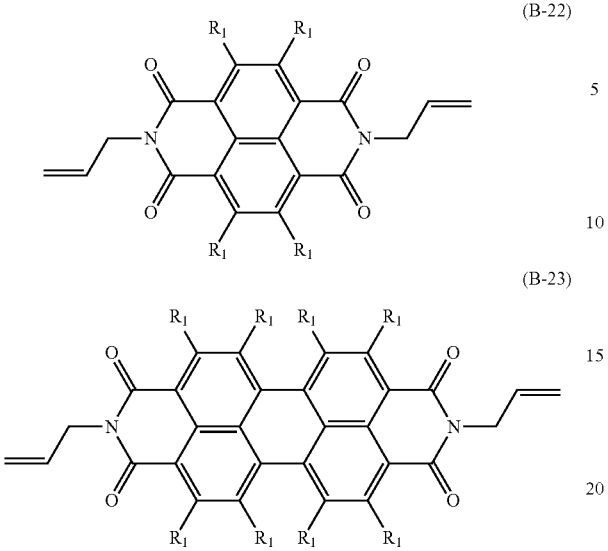
(B-22)
(B-23)

[Chem. 16]

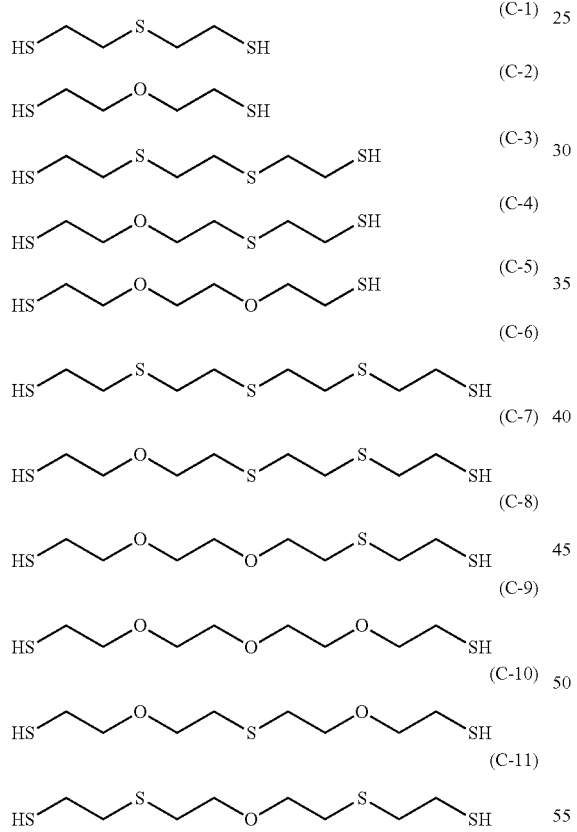

(In the chemical formula (B-1) to the chemical formula (B-23), $R_1$, $R_3$ to $R_5$ and $R_7$ to $R_9$ are the same as described above.

$R_{11}$'s each represent a group represented by any one of the chemical formula (R11-1) to the chemical formula (R11-5), and $R_{12}$ represents a group represented by any one of the chemical formula (R12-1) to the chemical formula (R12-10).)

[Chem. 17]

(R11-1)

(R11-2)

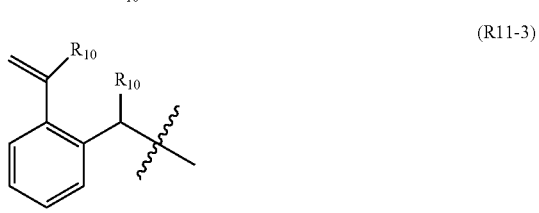
(R11-3)

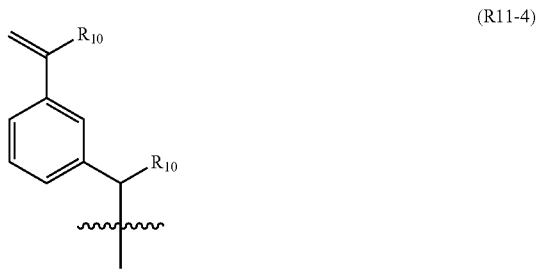
(R11-4)

(R11-5)

(In the chemical formula (R11-1) to the chemical formula (R11-5), $R_{10}$'s each are the same as described above. The wavy line portions each represent an atomic bonding.)

[Chem. 18]

(R12-1)

(R12-2)

(R12-3)

-continued

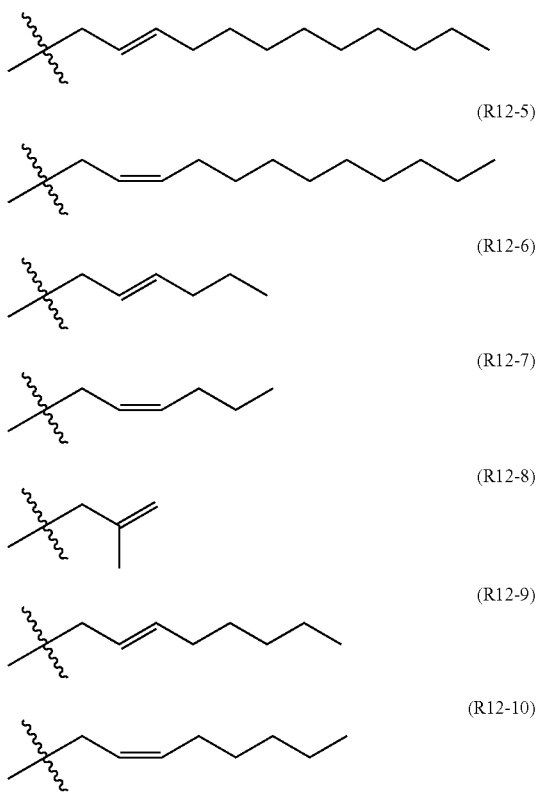

(R12-4)
(R12-5)
(R12-6)
(R12-7)
(R12-8)
(R12-9)
(R12-10)

(In the chemical formula (R12-1) to the chemical formula (R12-10), the wavy line portions each represent an atomic bonding.)

A third invention is a curing agent containing the thiol compound of the first invention.

A fourth invention is a resin composition (hereinafter, may be referred to as a "first resin composition") containing the thiol compound of the first invention and an epoxy compound.

A fifth invention is the resin composition of the fourth invention, further containing an amine as a curing accelerator.

A sixth invention is the resin composition of the fourth invention, further containing, as a curing accelerator, a reaction product between an epoxy compound and an amine.

A seventh invention is the resin composition of the fourth invention, further containing, as a curing accelerator, a reaction product between a compound having one or more isocyanate groups in a molecule and a compound having at least any of a primary amino group and a secondary amino group in a molecule.

An eighth invention is a resin composition (hereinafter, may be referred to as a "second resin composition") containing the thiol compound of the first invention, and an enic compound having a carbon-carbon double bond in a molecule.

A ninth invention is an adhesive containing the resin composition of any one of the fourth invention to the eighth invention.

A tenth invention is a sealant containing the resin composition of any one of the fourth invention to the eighth invention.

Advantageous Effects of Invention

The thiol compound of the present invention is a novel compound having two or more thioether bonds in the molecule. Such a thiol compound is expected to be used as a curing agent for resins, raw materials for resins, and an intermediate raw material for various sulfur-containing compounds. Furthermore, the thiol compound of the present invention is expected to have low volatility, and further, to have excellent compatibility with an epoxy compound, an enic compound and the like (low crystallinity).

Since the thiol compound of the present invention does not have an ester bond in the molecule, when used as a curing agent for resins or a raw material for resins, it is expected to provide a cured product having excellent hydrolysis resistance as compared with a case where a conventional polythiol compound is used. It is also expected to provide a cured product having low elasticity.

Furthermore, the adhesive and the sealant of the present invention are expected to have excellent moisture resistance, water resistance and the like.

DESCRIPTION OF EMBODIMENTS

Figure 1:
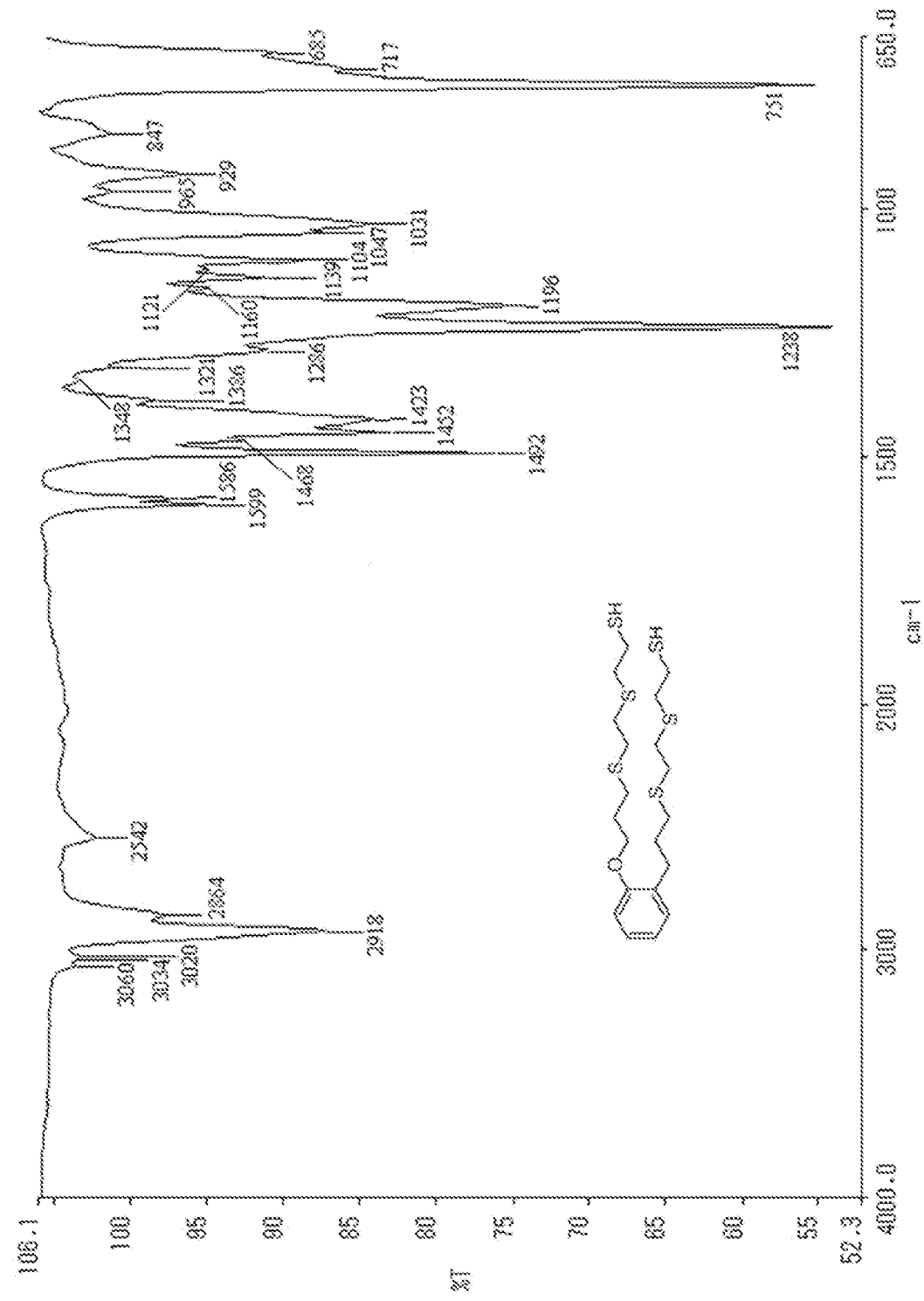
FIG. 1 is an IR spectral chart of a yellow liquid obtained in Example 1.

The present invention relates to the thiol compound represented by the above-described chemical formula (I), a synthesis method thereof, and the utilization of the thiol compound.

Examples of the thiol compound represented by the chemical formula (I) include thiol compounds represented by the chemical formula (I-1) to the chemical formula (I-128).

[Chem. 19]
(I-1)
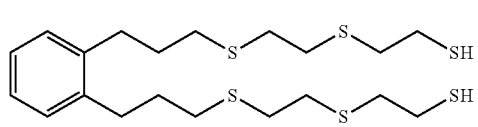
(I-2)
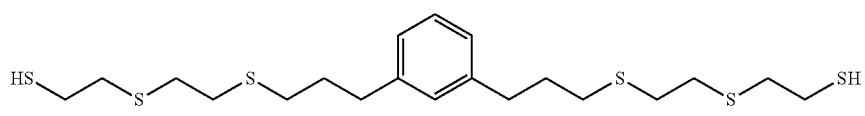
(I-3)
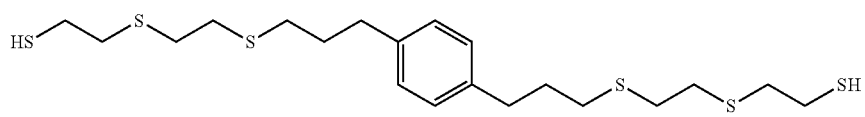
(I-4)
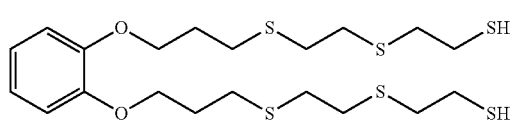
(I-5)
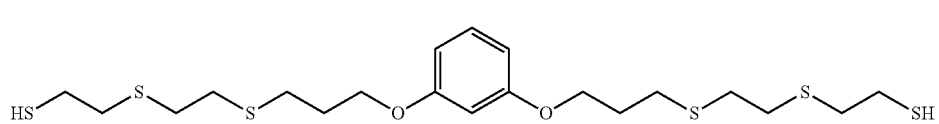
(I-6)
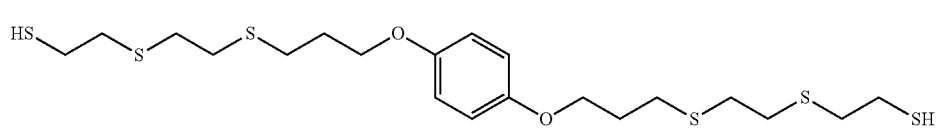
(I-7)
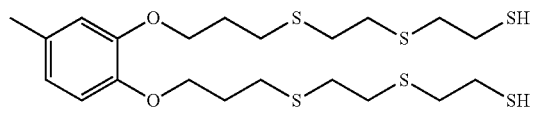
(I-8)
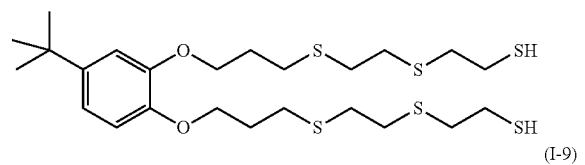
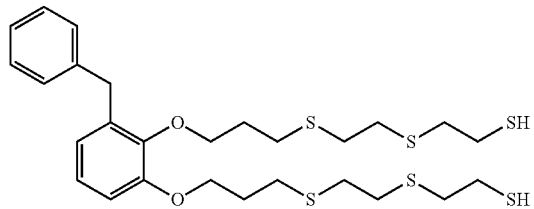
(I-9)
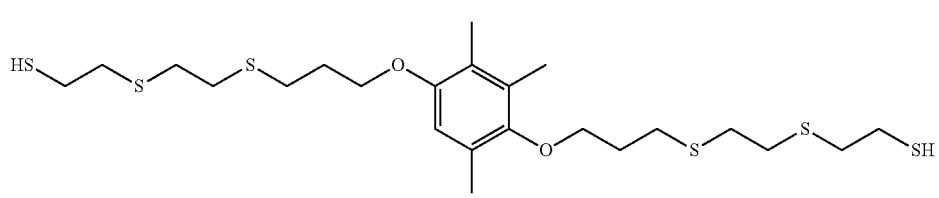
(I-10)
(I-11)
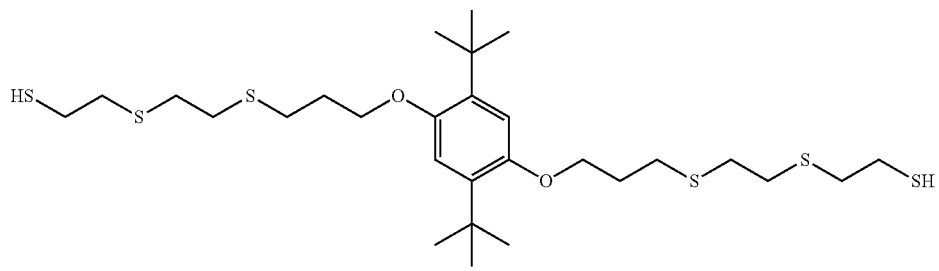

-continued
(I-12)
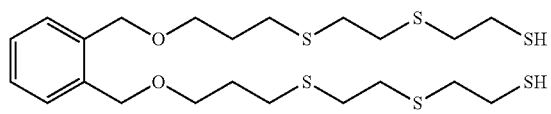
(I-13)
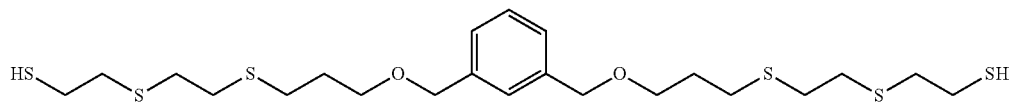
[Chem. 20]
(I-14)
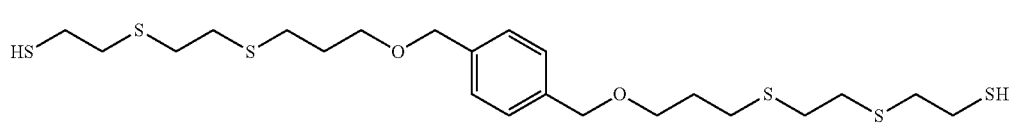
(I-15)
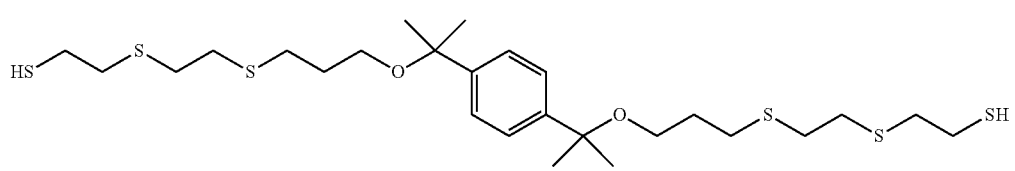
(I-16)
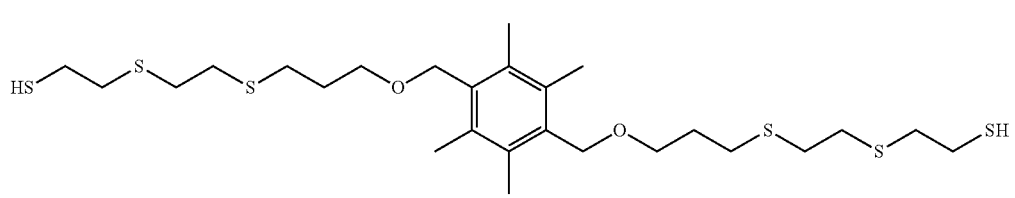
(I-17)
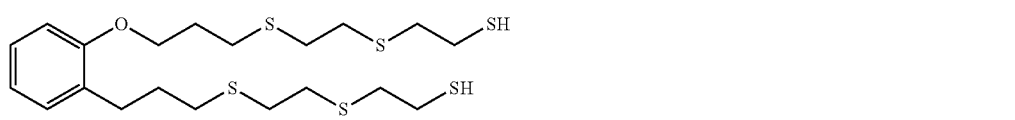
(I-18)
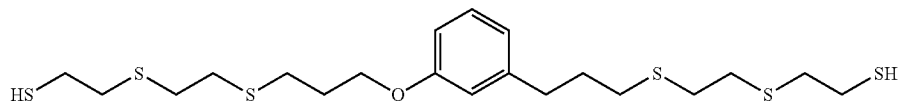
(I-19)
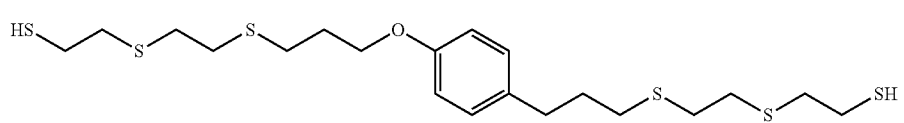
(I-20)
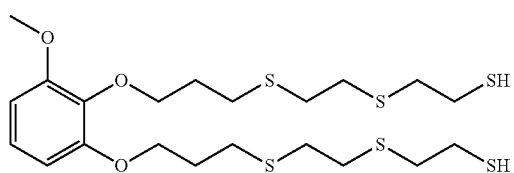
(I-21)
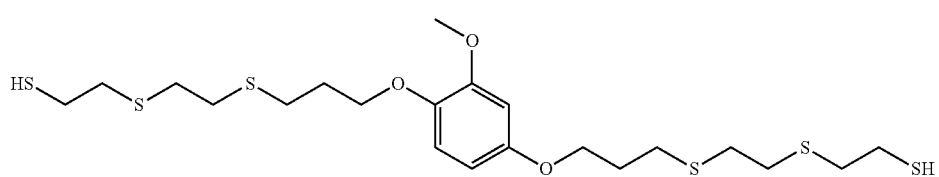

-continued
(I-22)
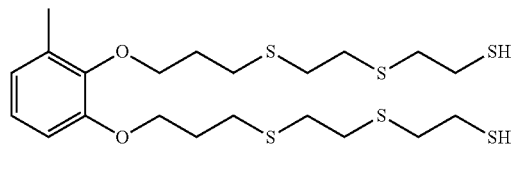
(I-23)
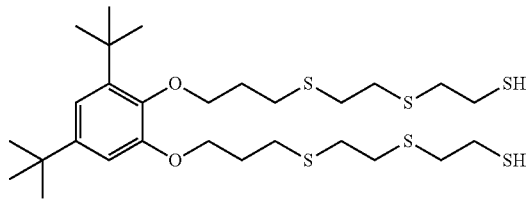
(I-24)
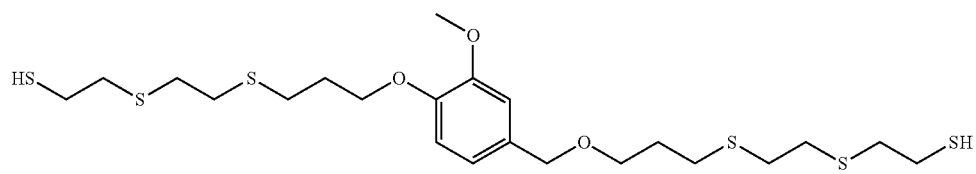
(I-25)
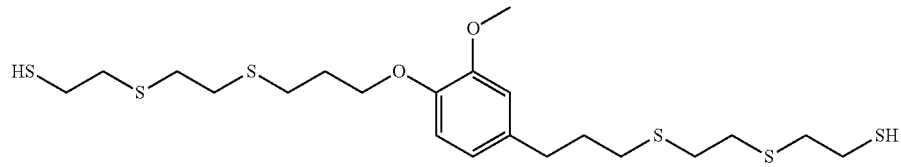
[Chem. 21]
(I-26)
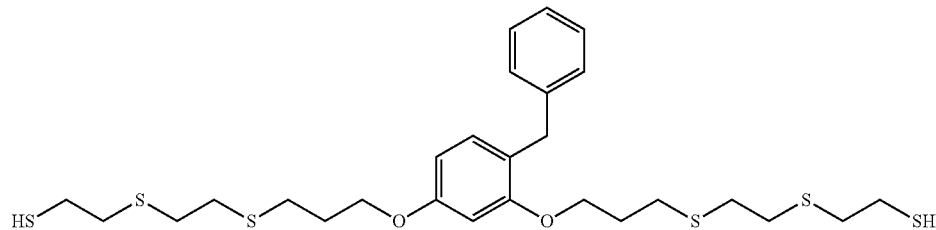
(I-27)
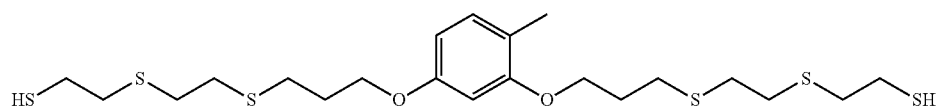
(I-28)
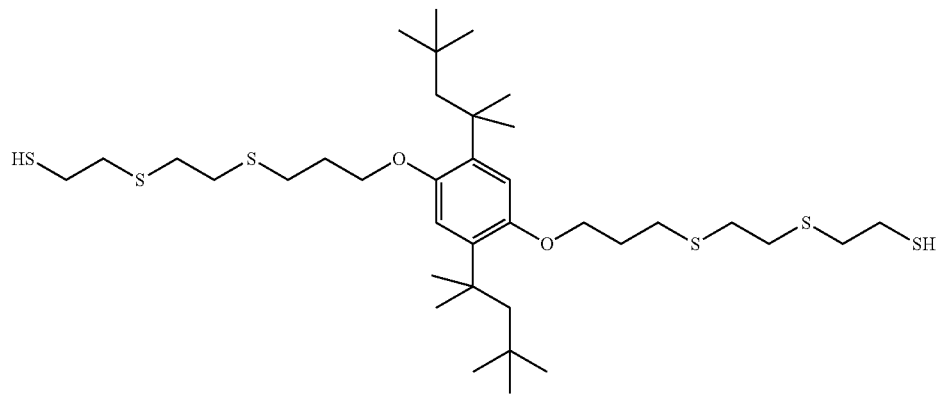

(I-29)
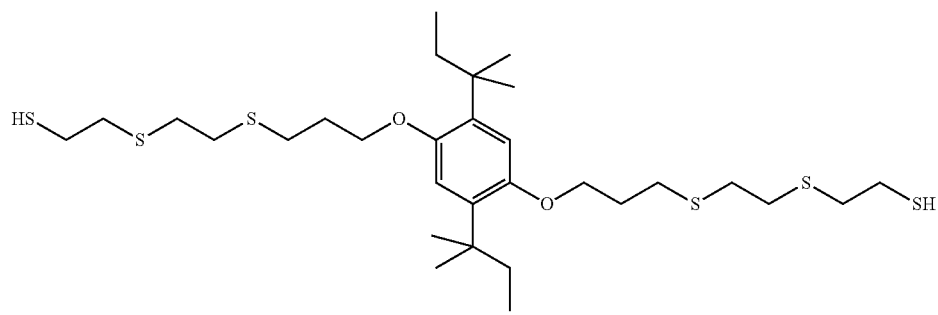
(I-30)
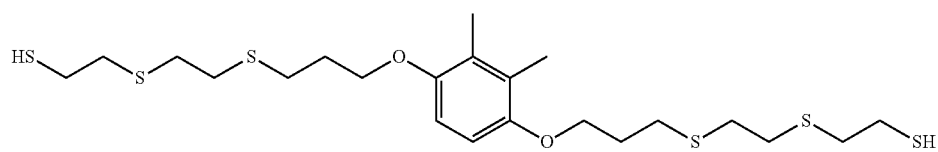
[Chem. 22]
(I-31)
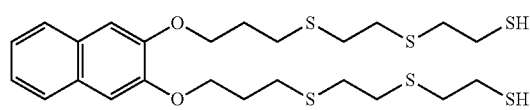
(I-32)
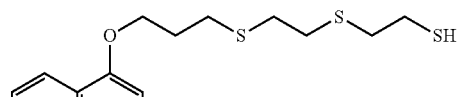
(I-33)
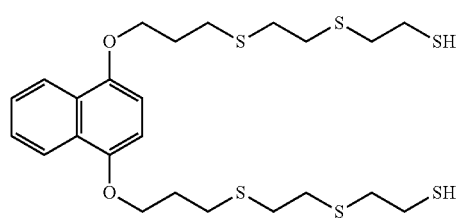
(I-34)
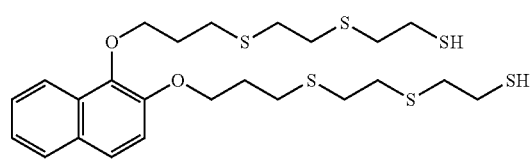
(I-35)
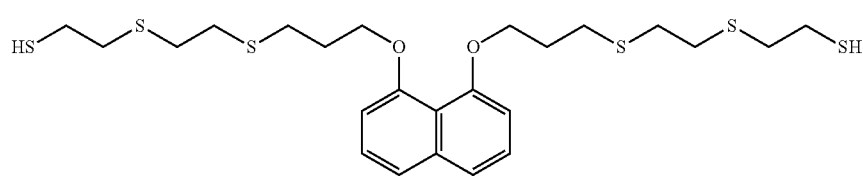
(I-36)
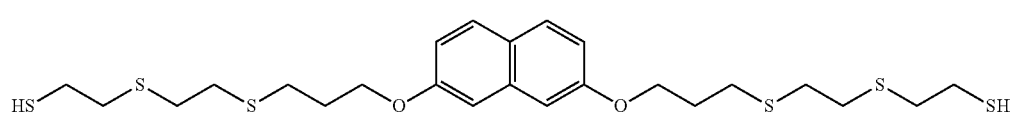
(I-37)
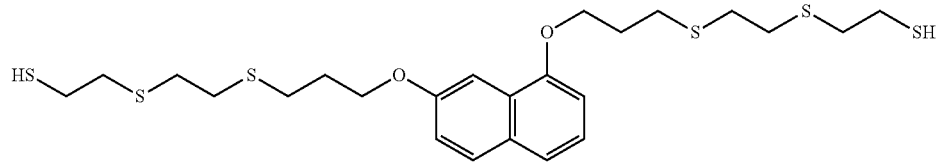
(I-38)
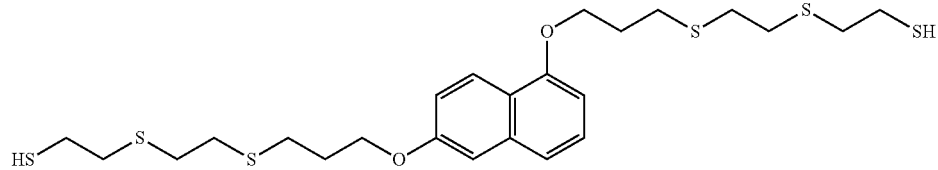

-continued
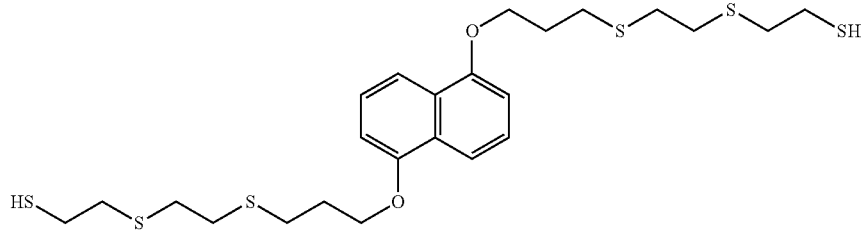
(I-39)
[Chem. 23]
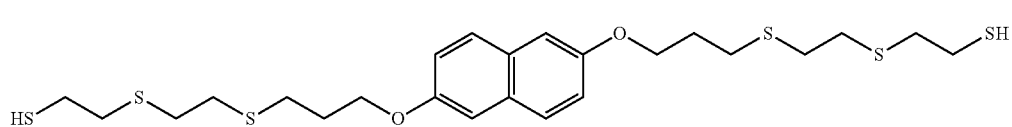
(I-40)
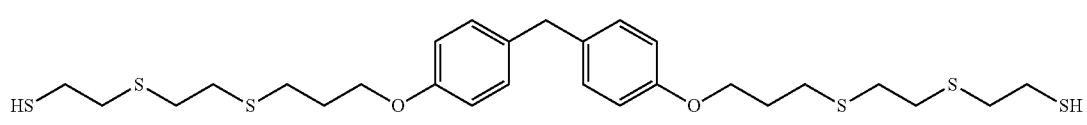
(I-41)
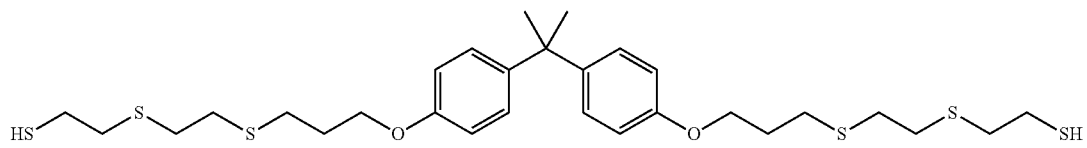
(I-42)
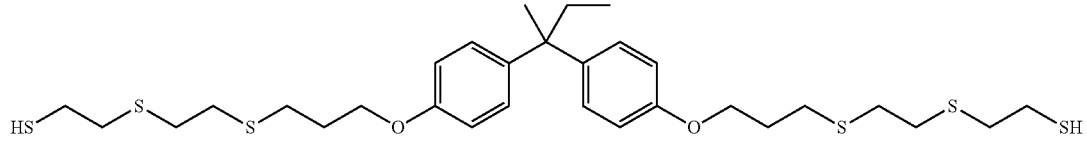
(I-43)
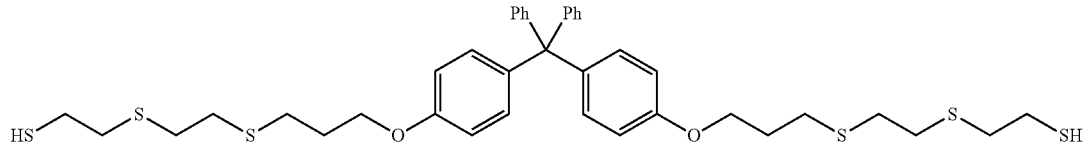
(I-44)
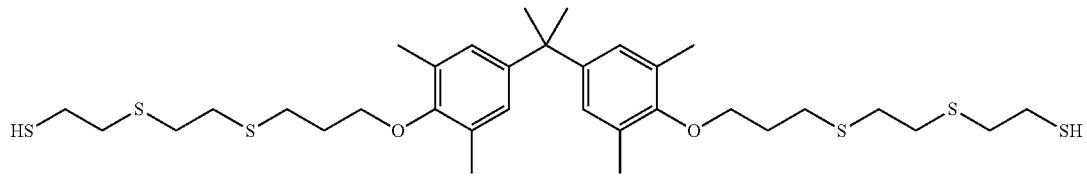
(I-45)
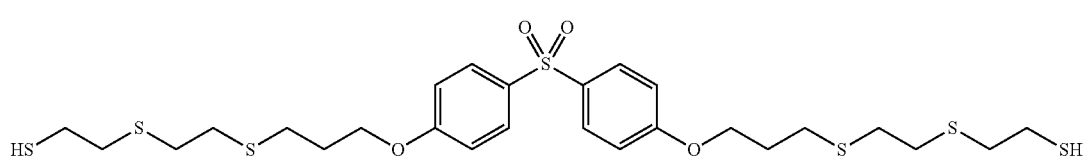
(I-46)
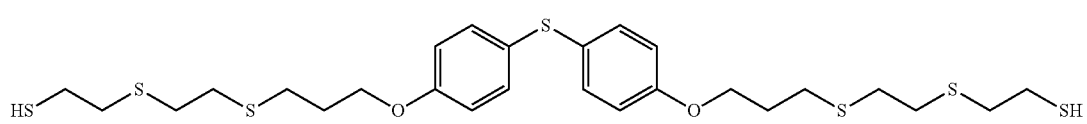
(I-47)
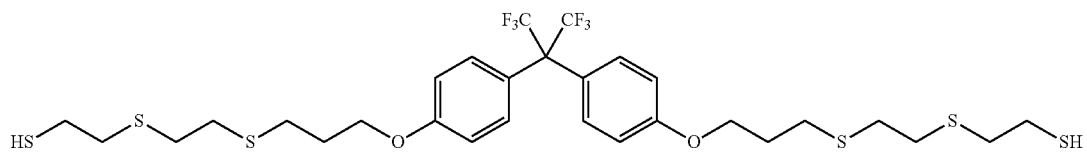
(I-48)

-continued
[Chem. 24]
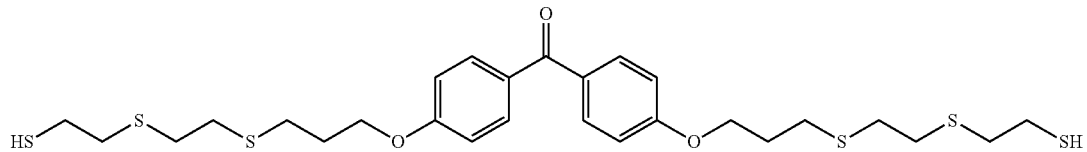
(I-49)
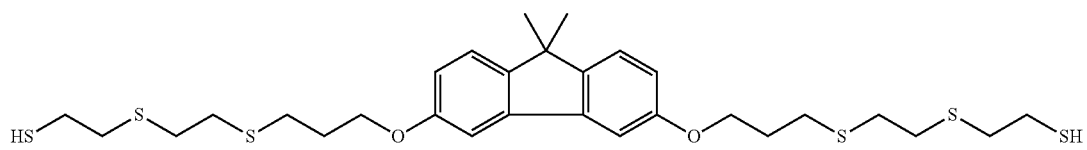
(I-50)
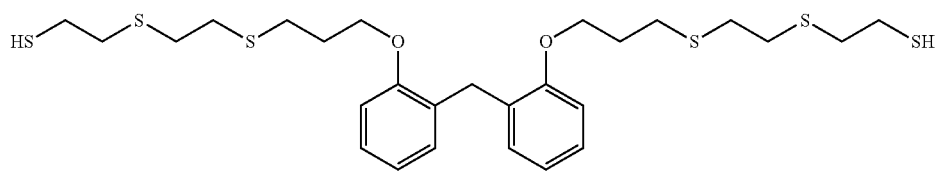
(I-51)
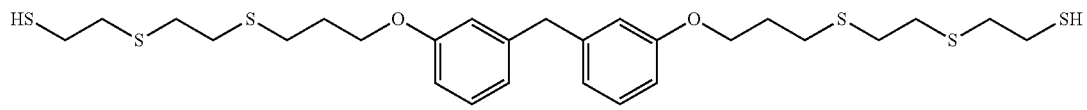
(I-52)
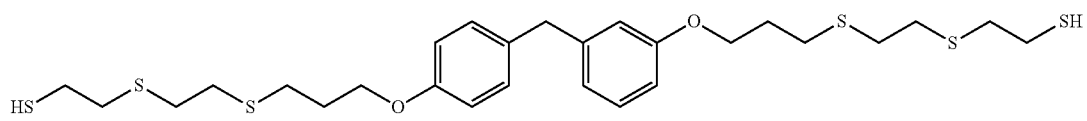
(I-53)
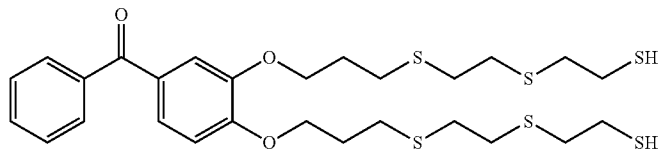
(I-54)
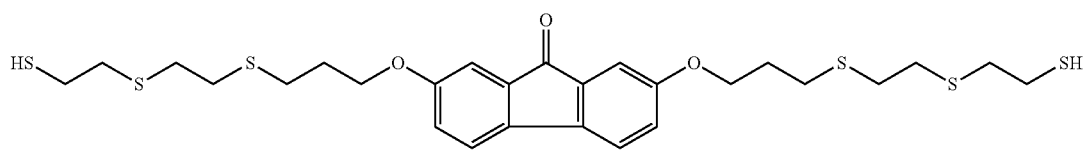
(I-55)
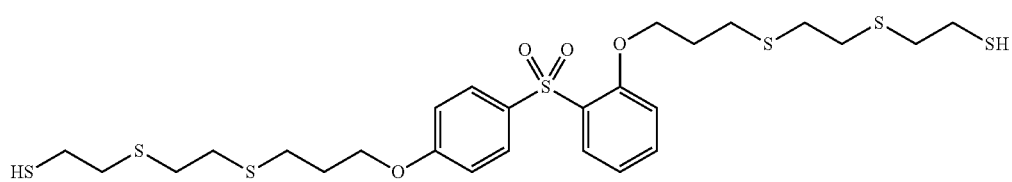
(I-56)
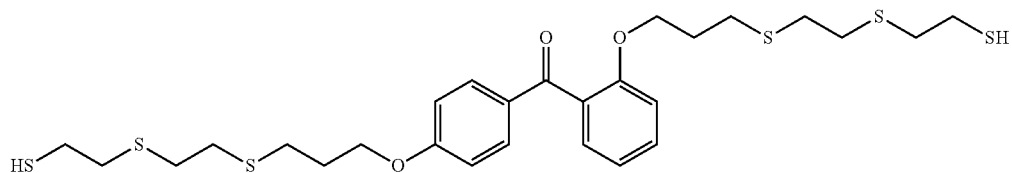
(I-57)

[Chem. 25]
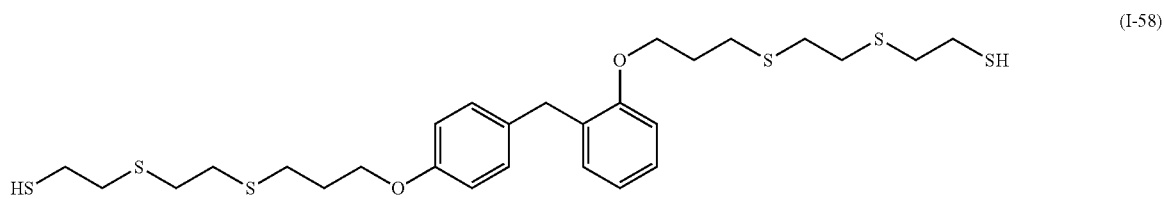
(I-58)
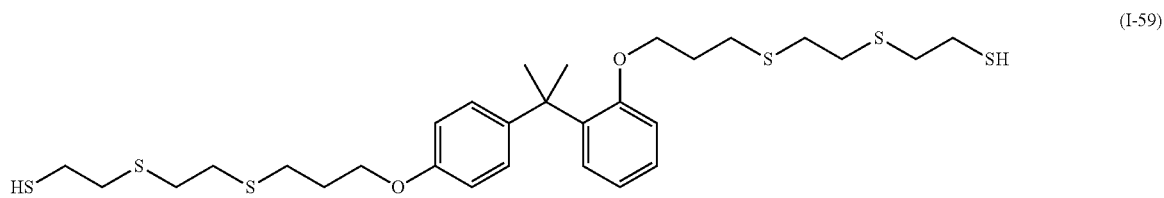
(I-59)
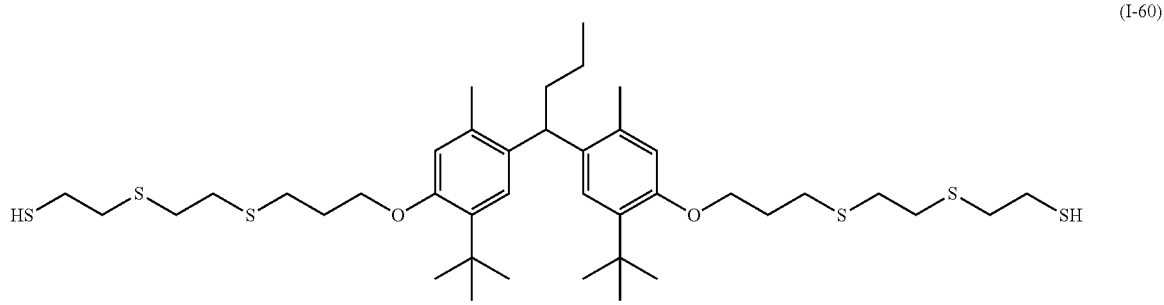
(I-60)
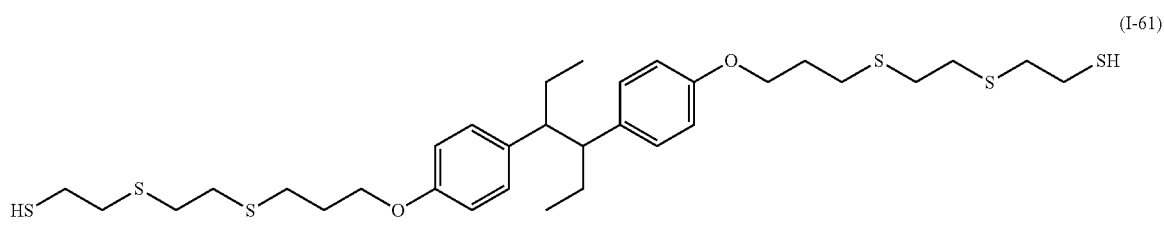
(I-61)
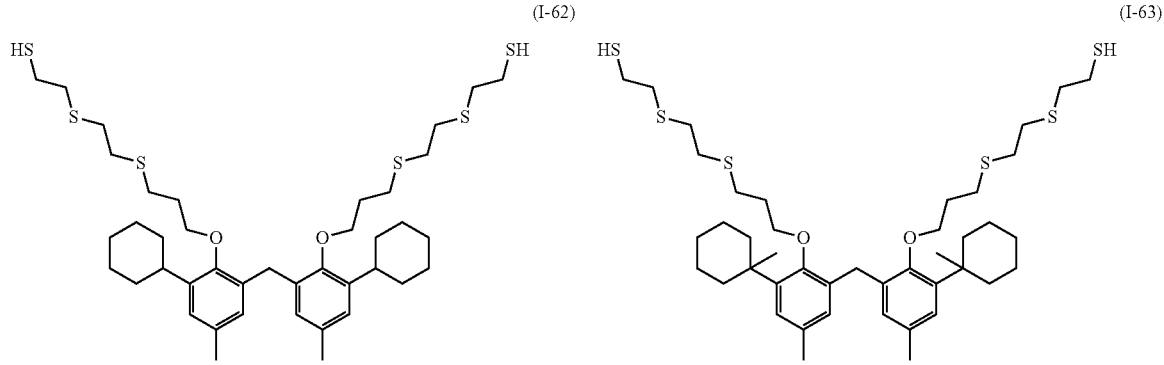
(I-62) (I-63)
[Chem. 26]
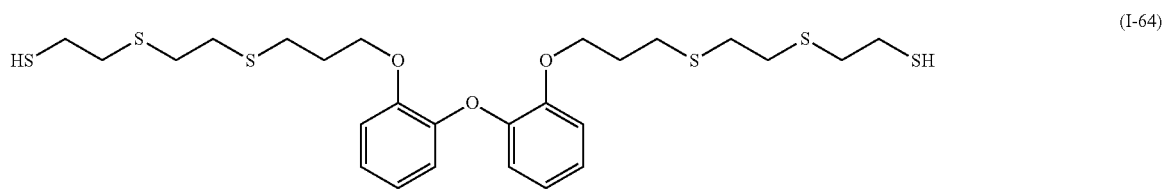
(I-64)
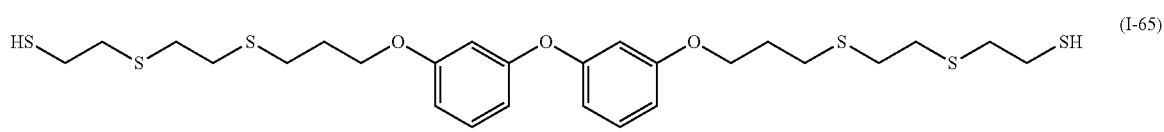
(I-65)

(I-66)
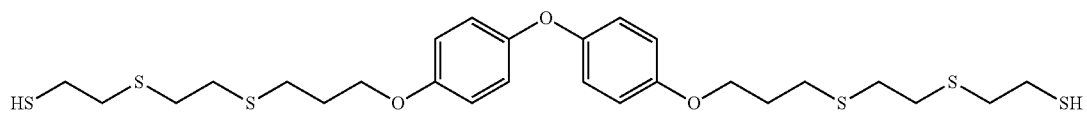
(I-67)
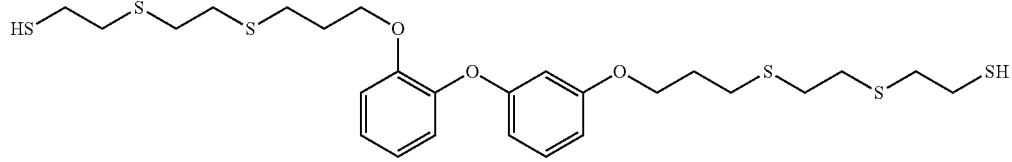
(I-68)
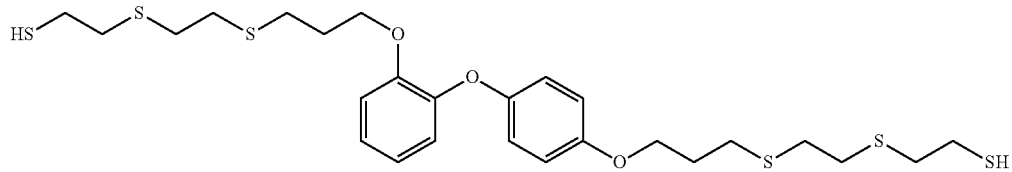
(I-69)
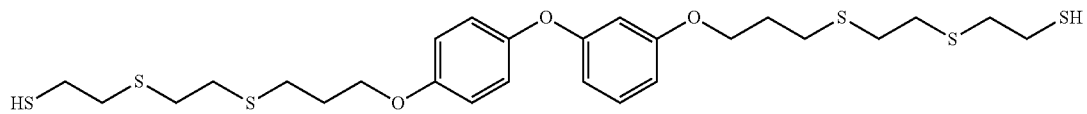
(I-70)
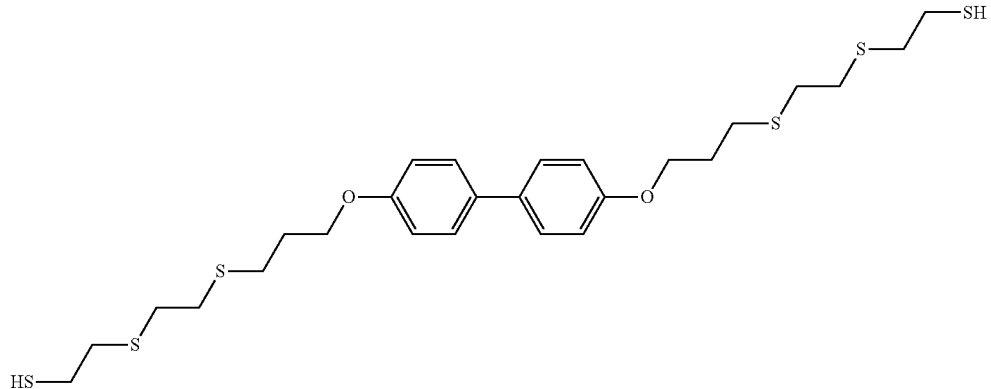
[Chem. 27]
(I-71)
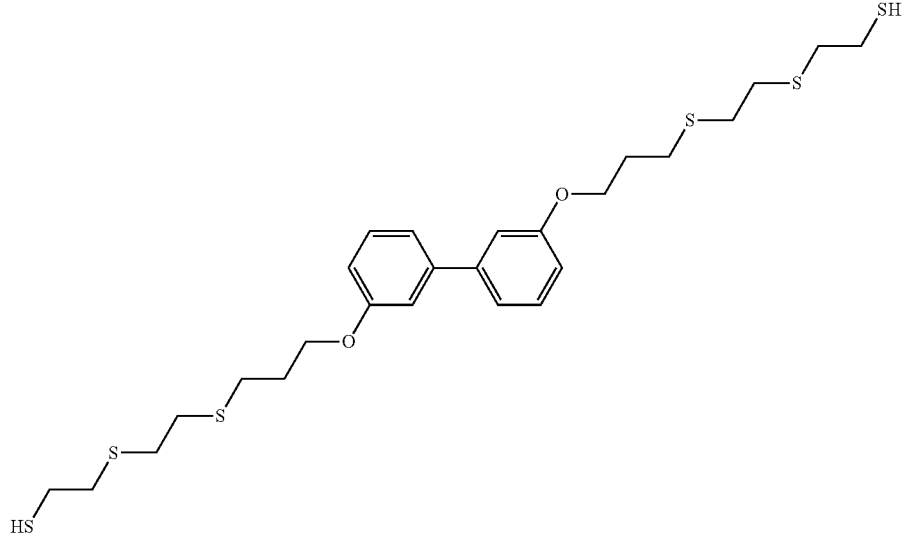

(I-72)
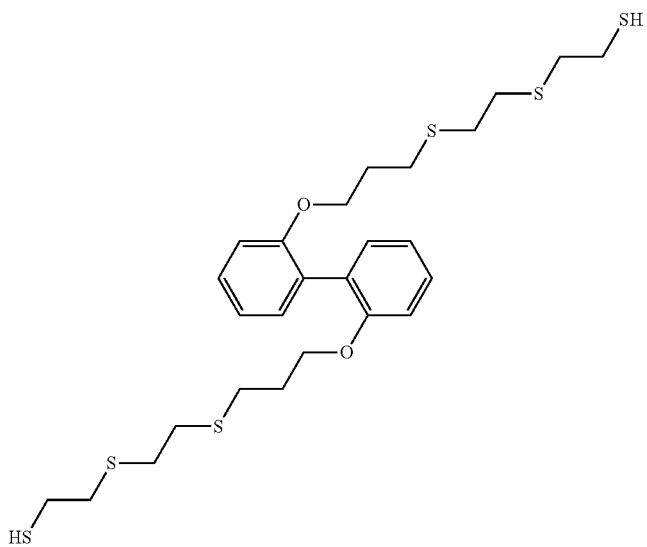
(I-73)
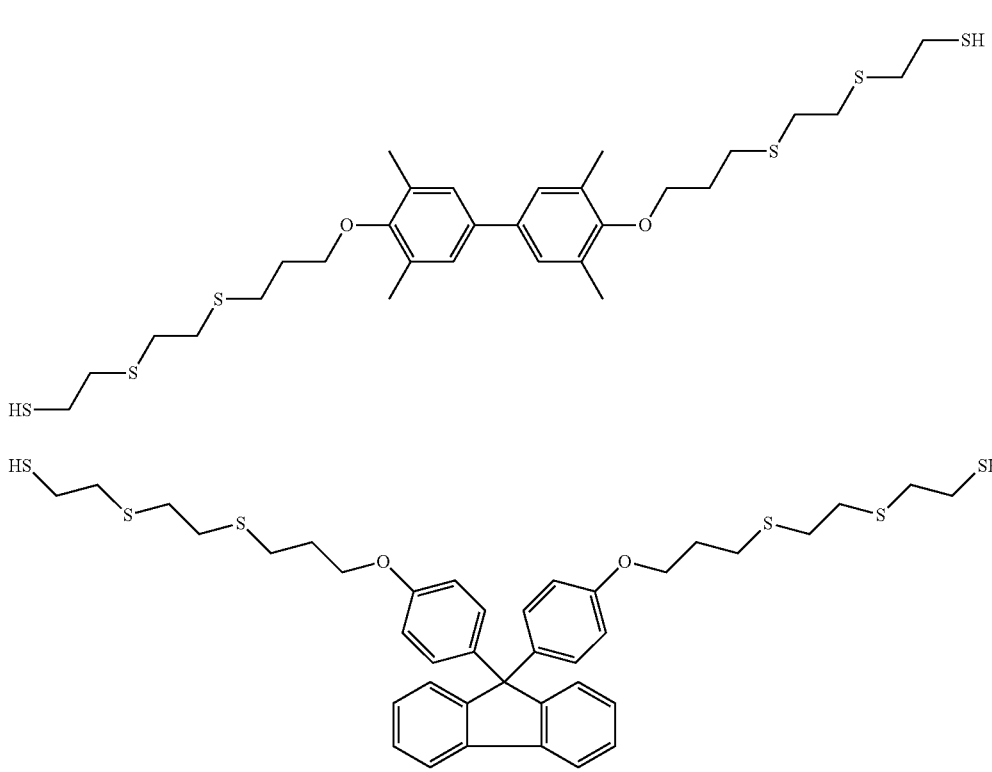
(I-74)
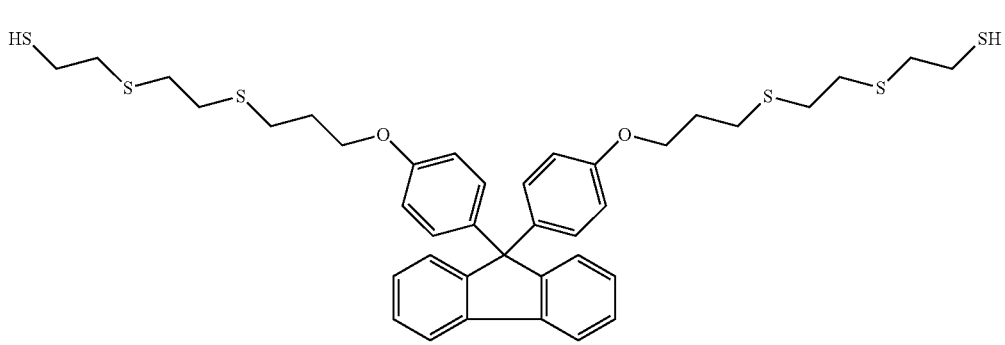
(I-75)
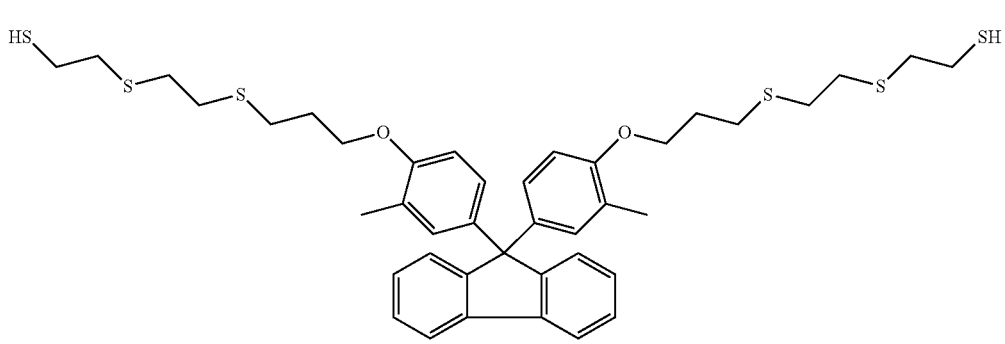

-continued
[Chem. 28]
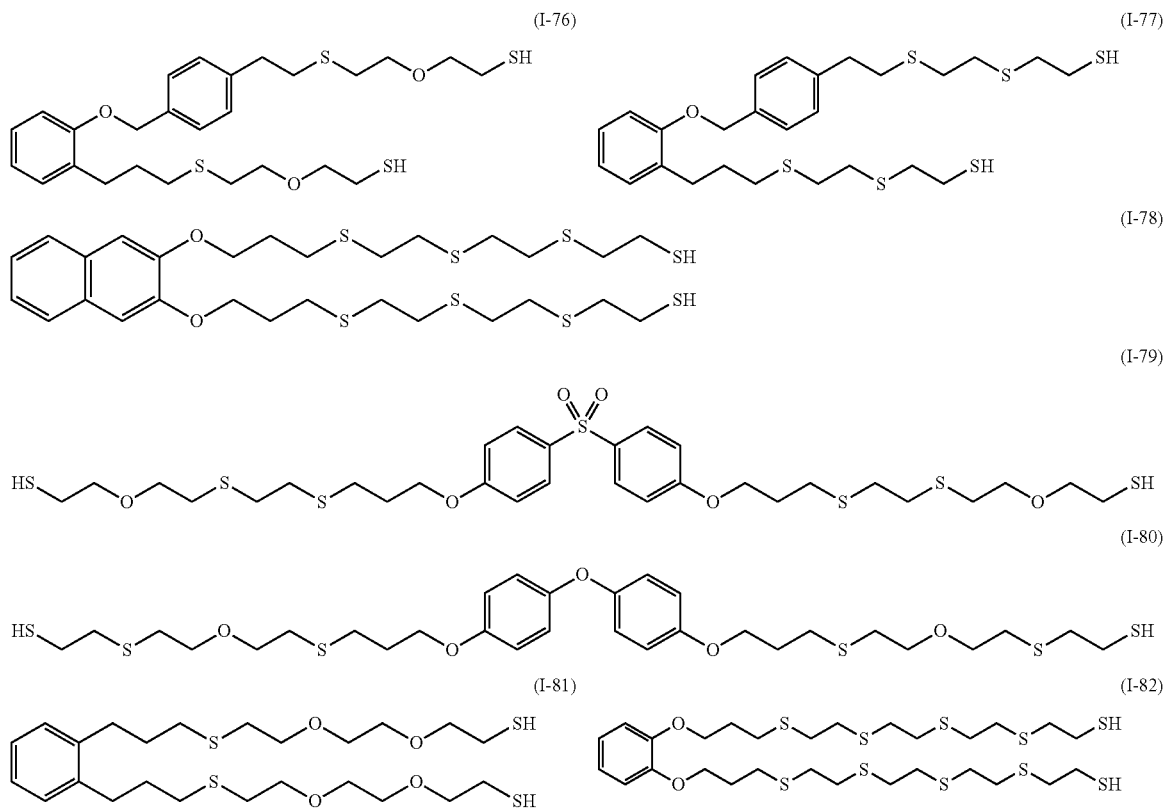
[Chem. 29]
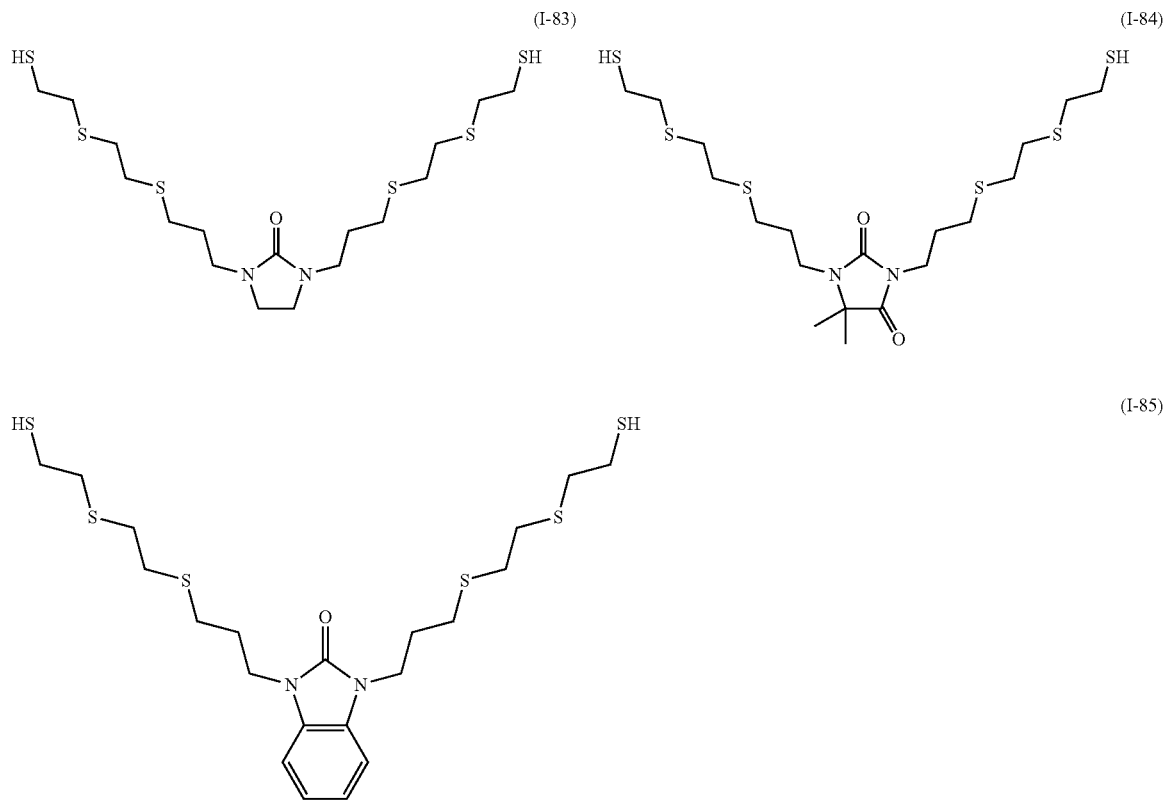

(I-86)
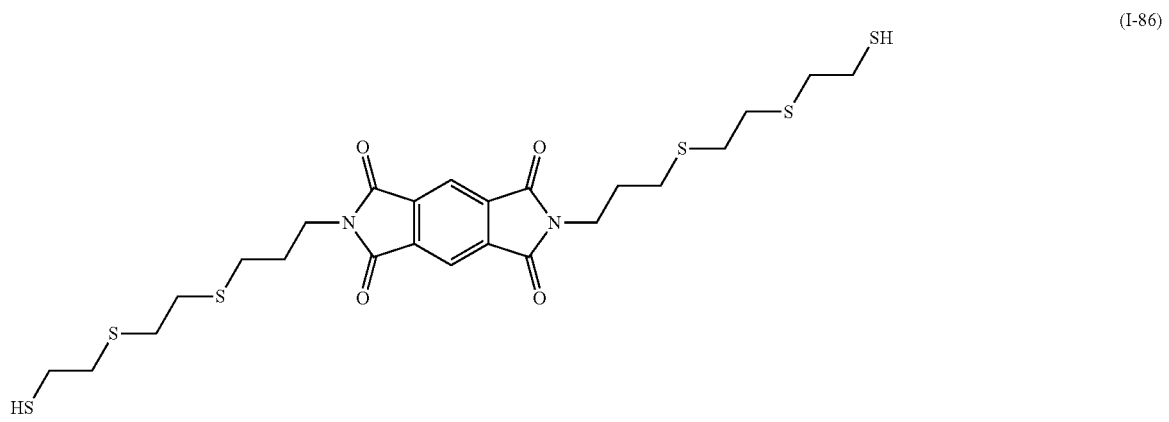
(I-87)
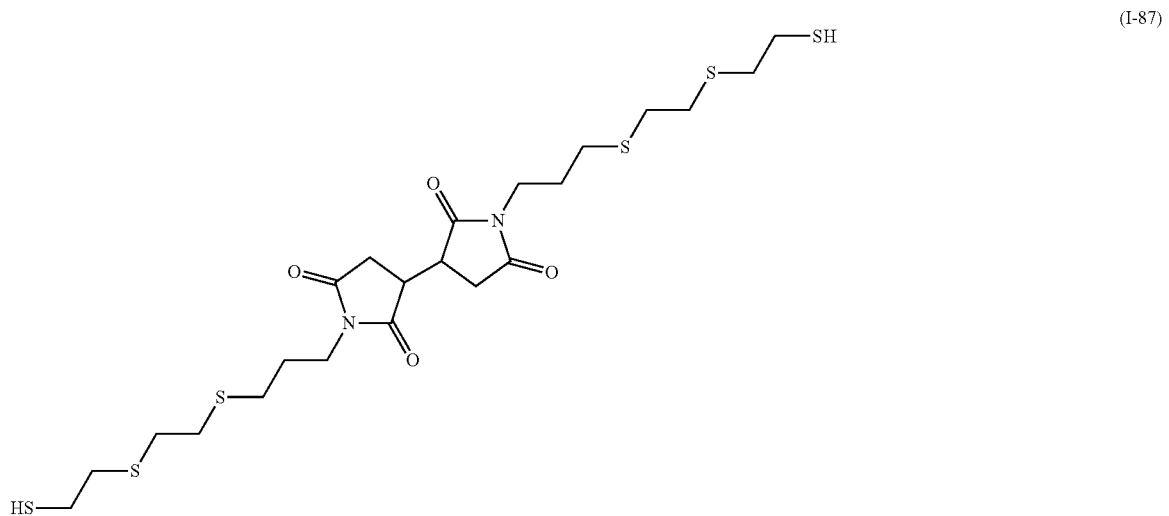
[Chem. 30]
(I-88) (I-89)
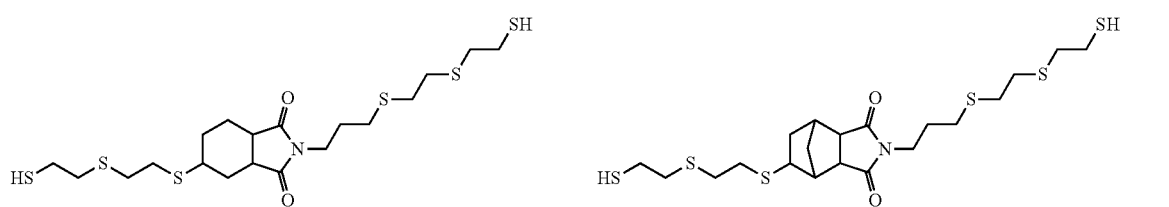
(I-90)
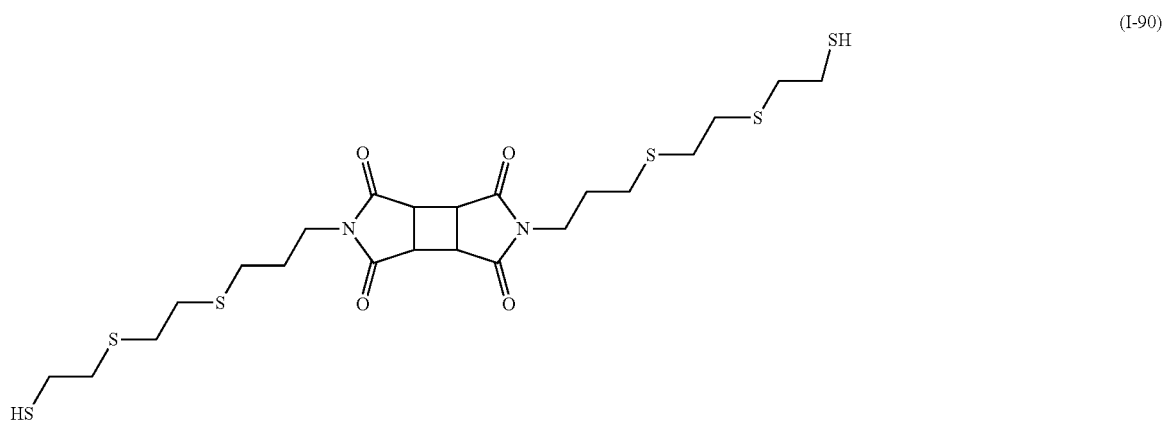

-continued
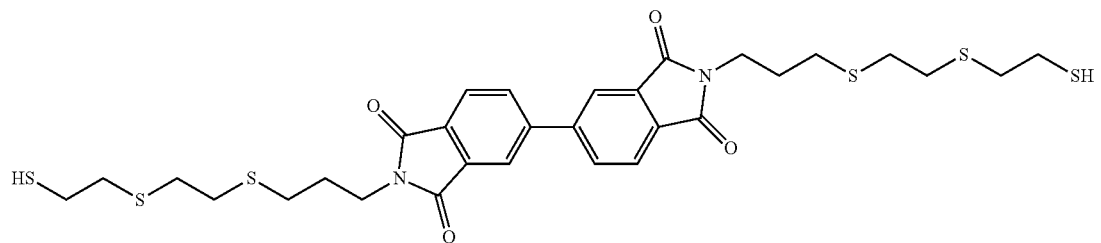
(I-91)
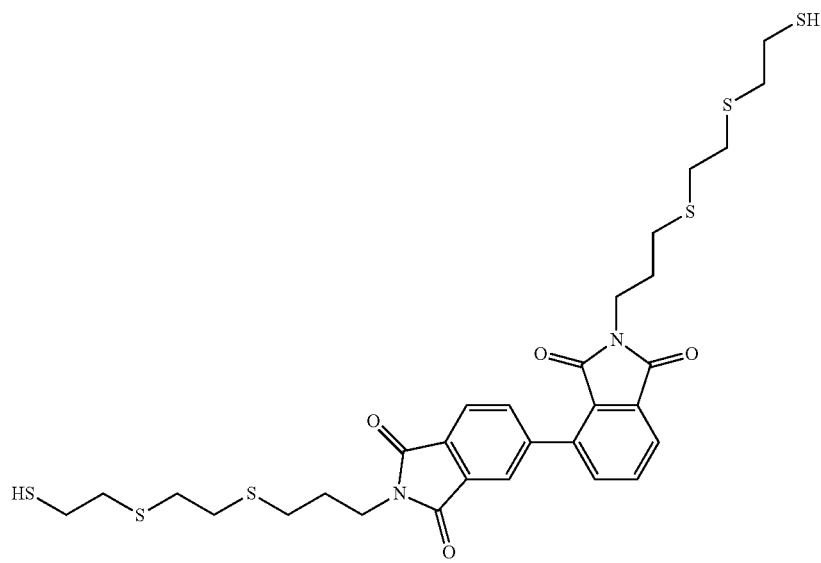
(I-92)
[Chem. 31]
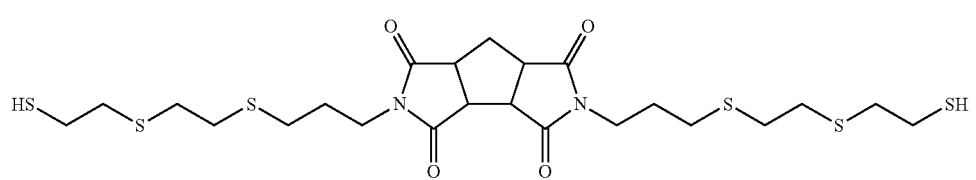
(I-93)
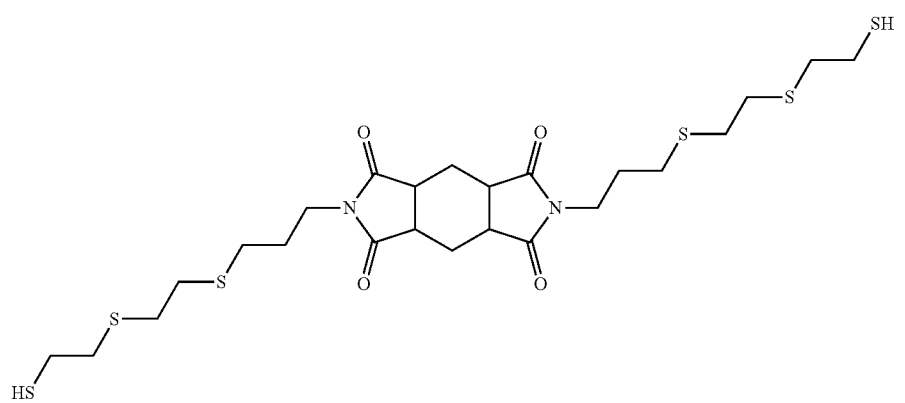
(I-94)

(I-95)
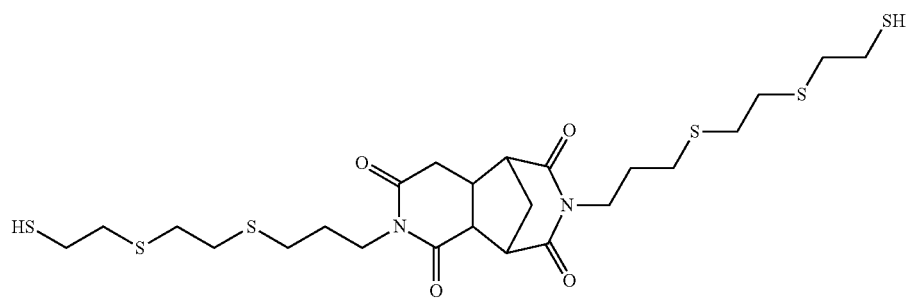
(I-96)
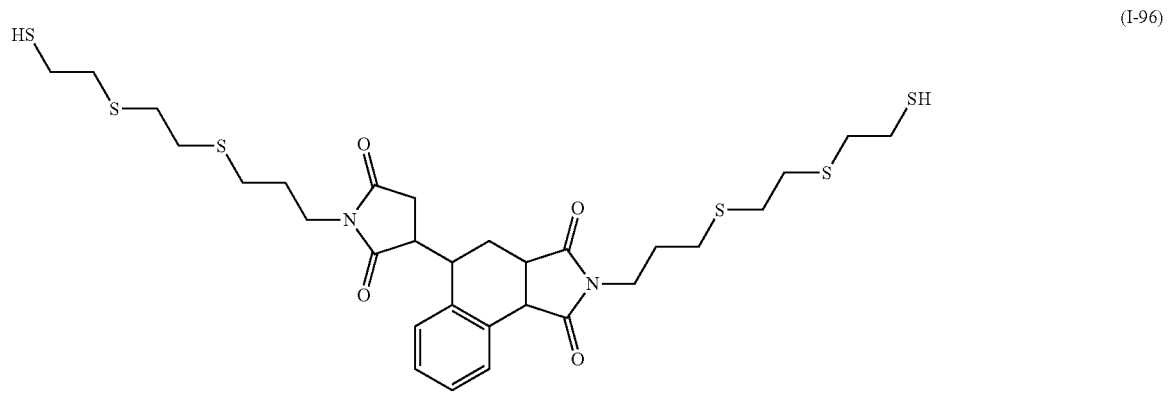
(I-97)
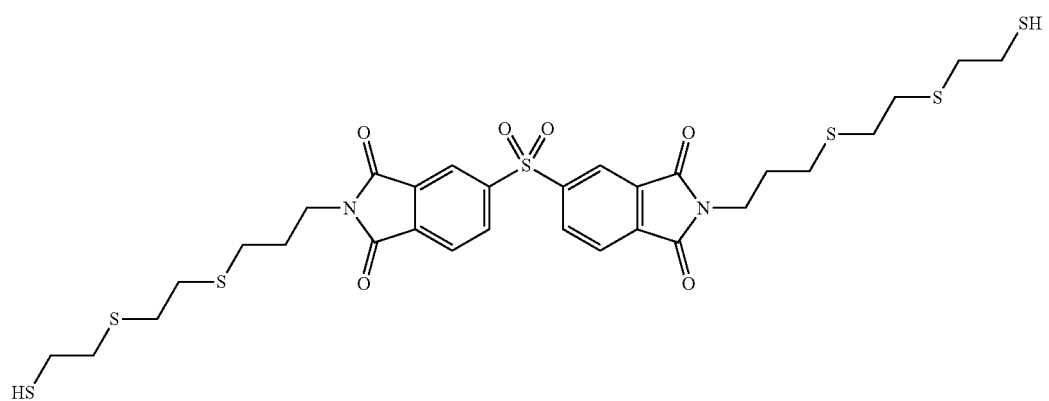
(I-98)

-continued
[Chem. 32]
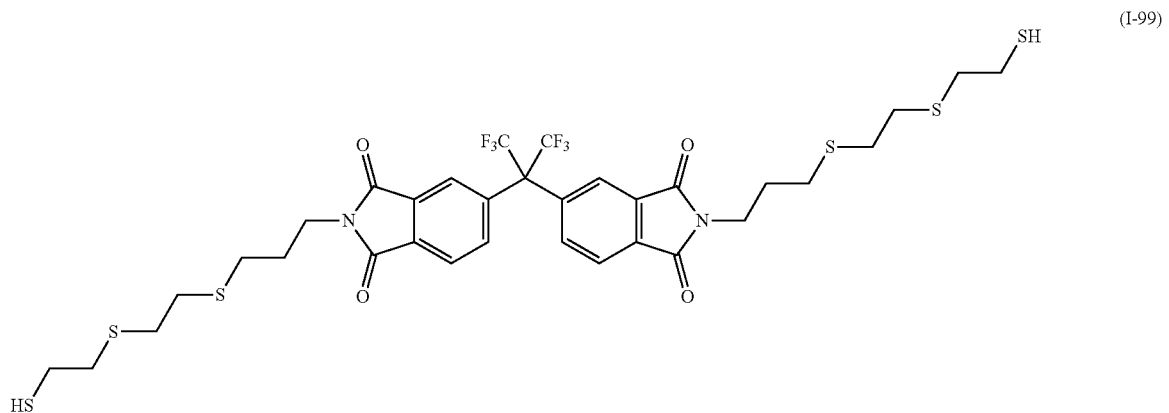
(I-99)
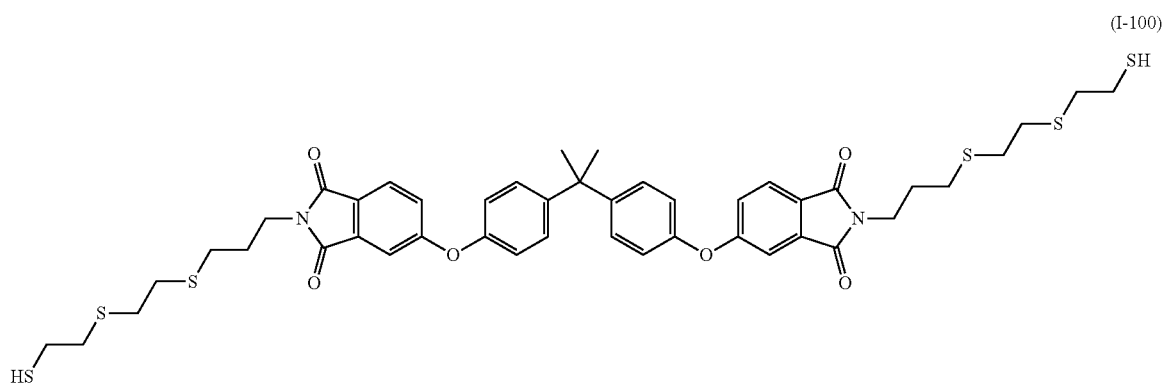
(I-100)
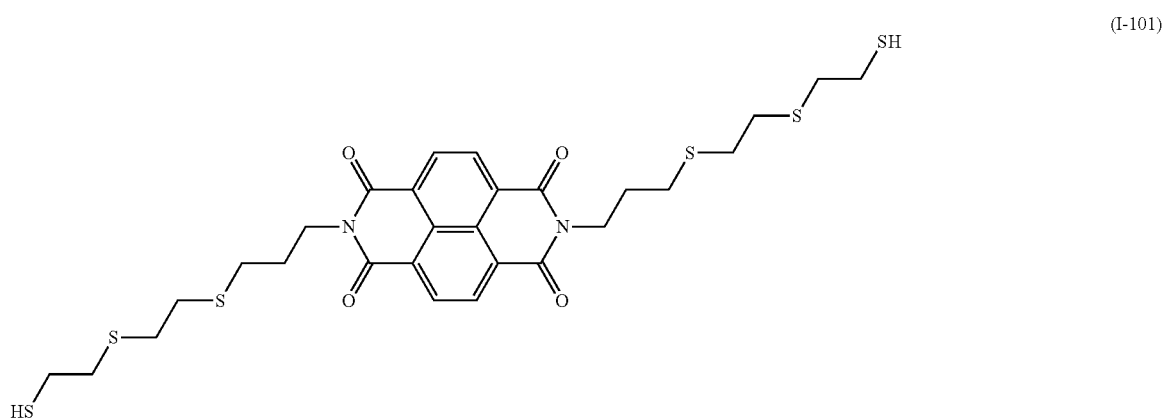
(I-101)
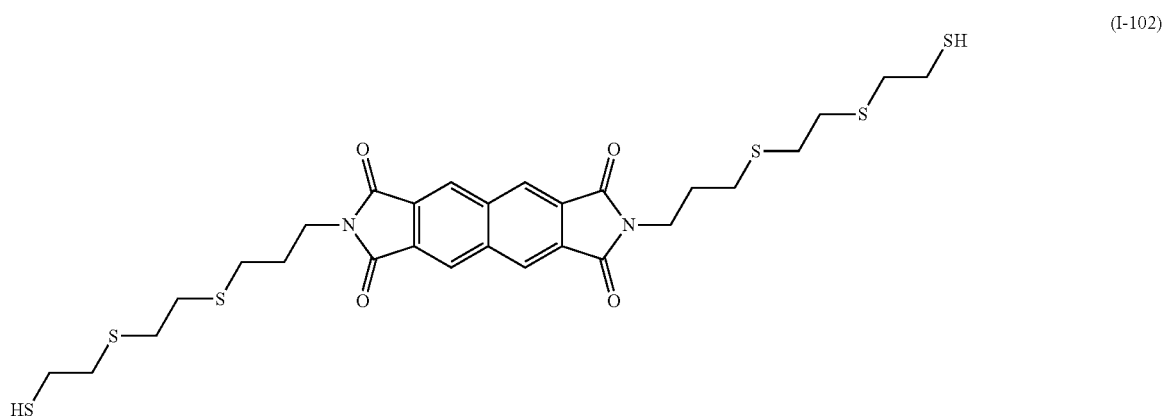
(I-102)

(I-103)
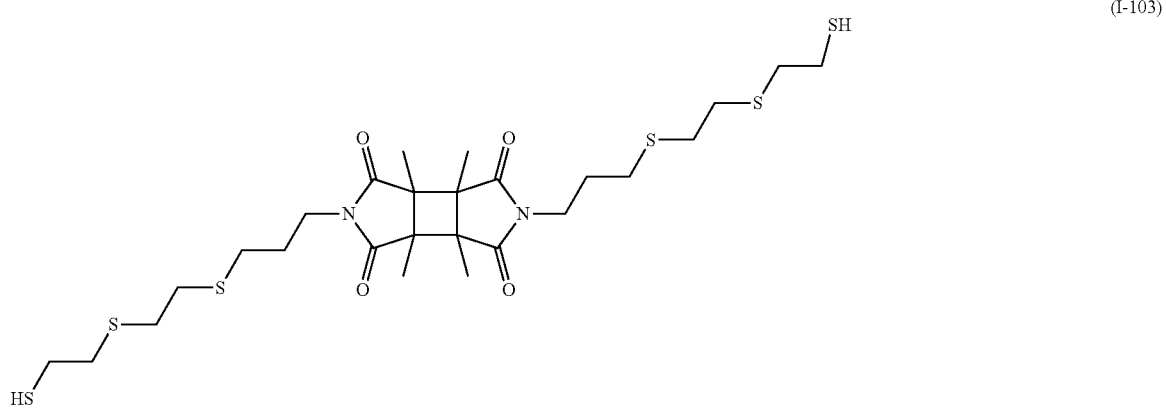
(I-104)
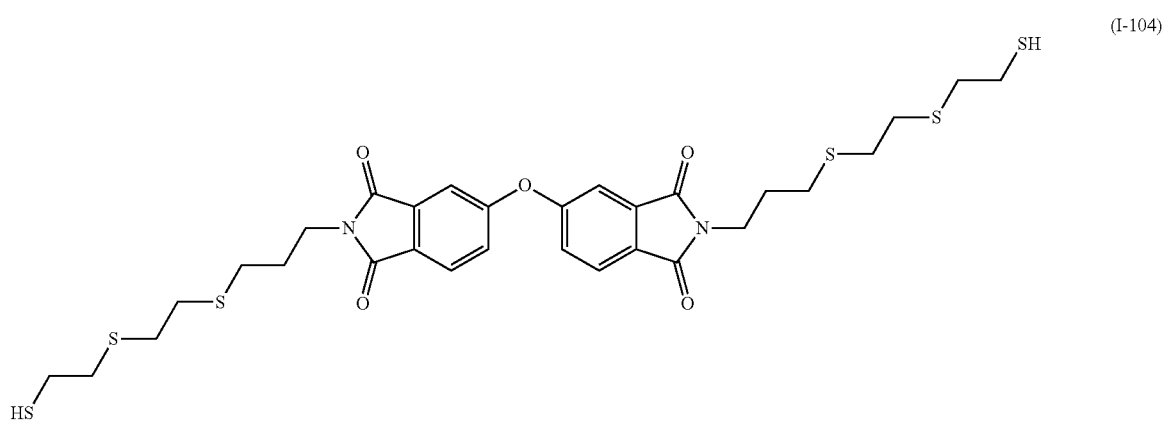
[Chem. 33]
(I-105)
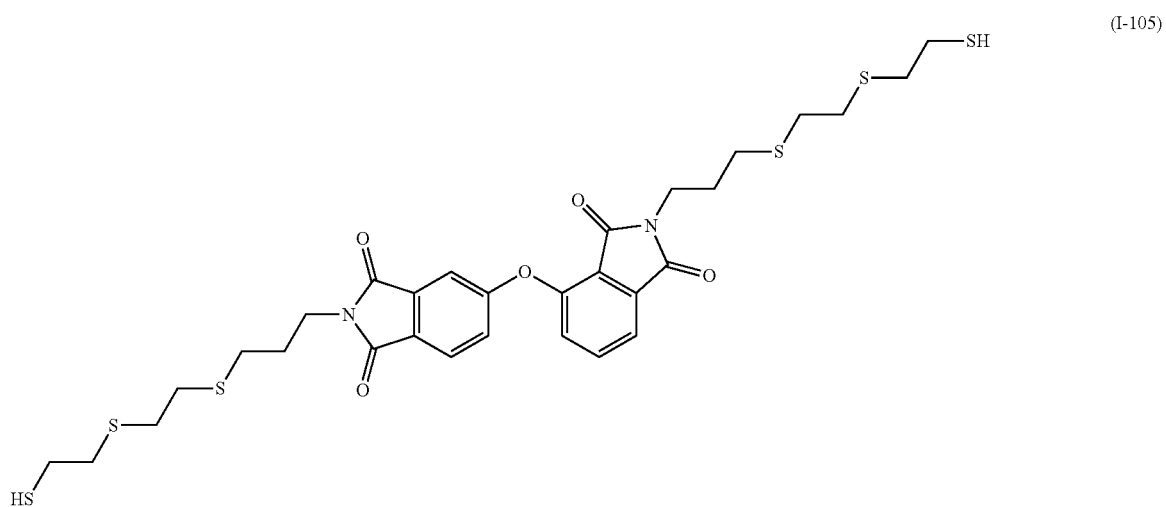

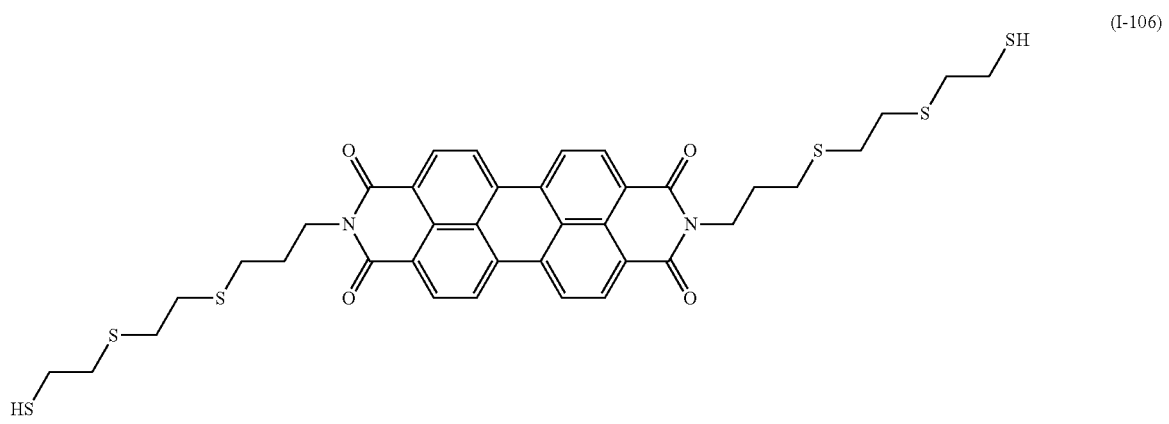
(I-106)
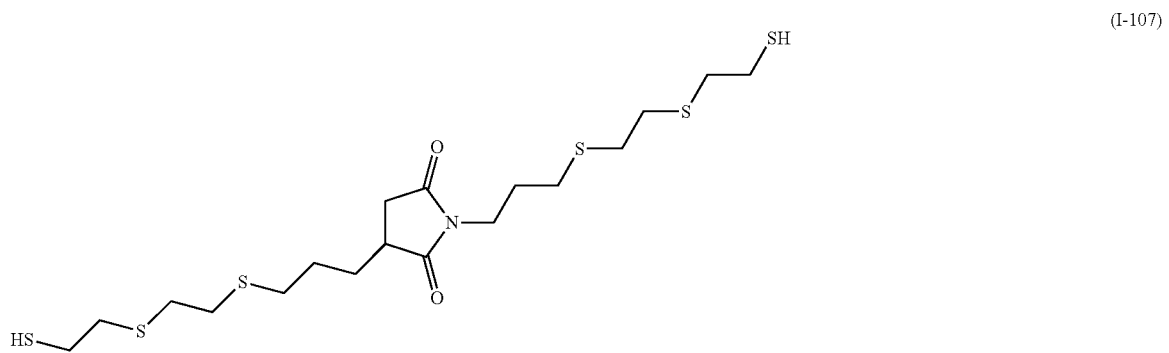
(I-107)
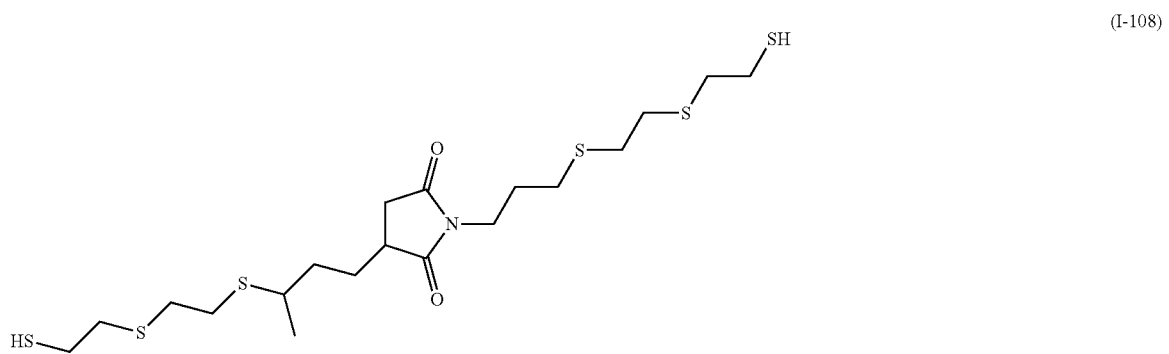
(I-108)
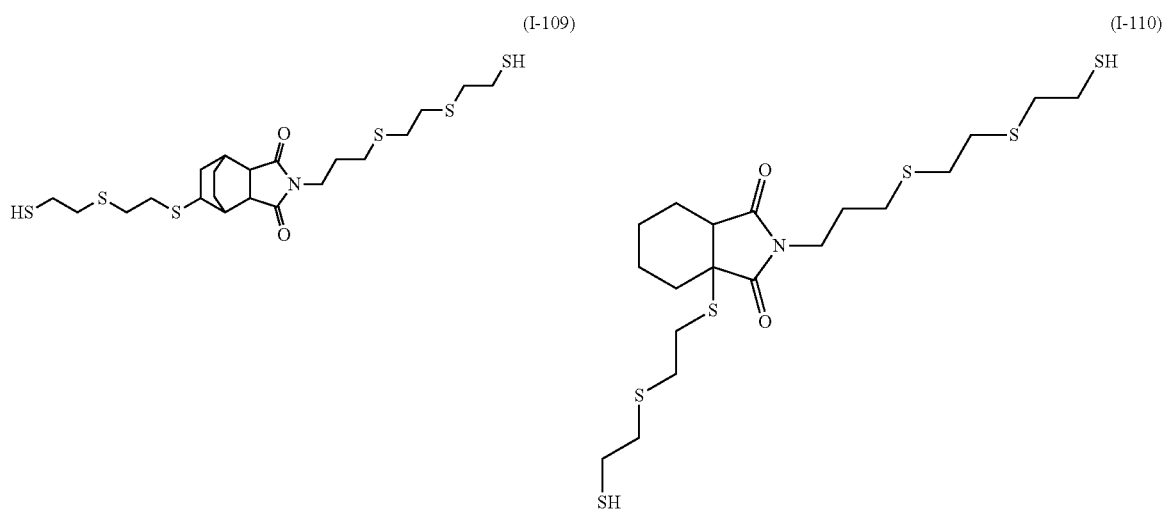
(I-109)                                                                 (I-110)

[Chem. 34]
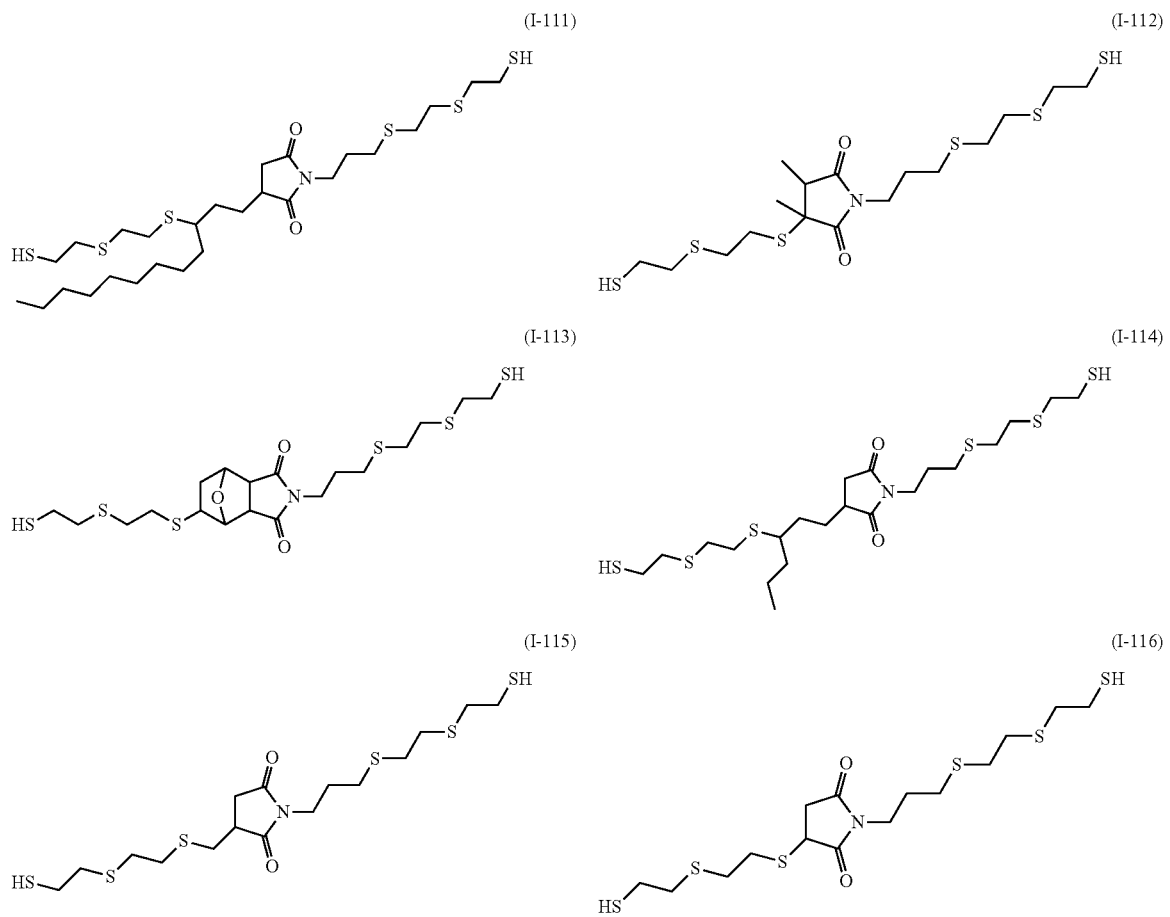
[Chem. 35]
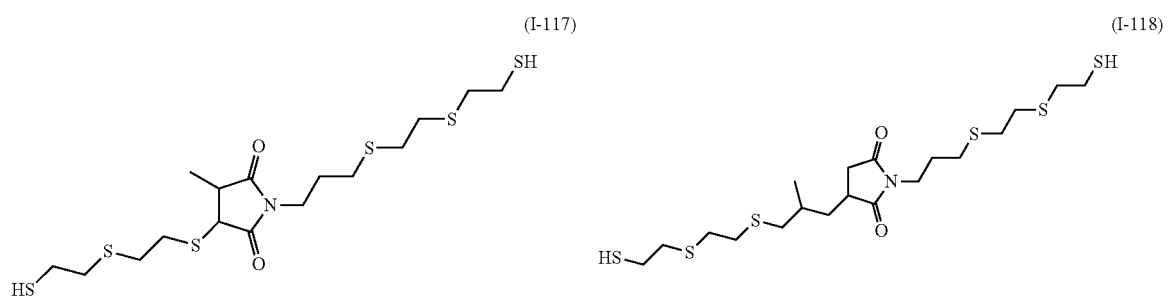
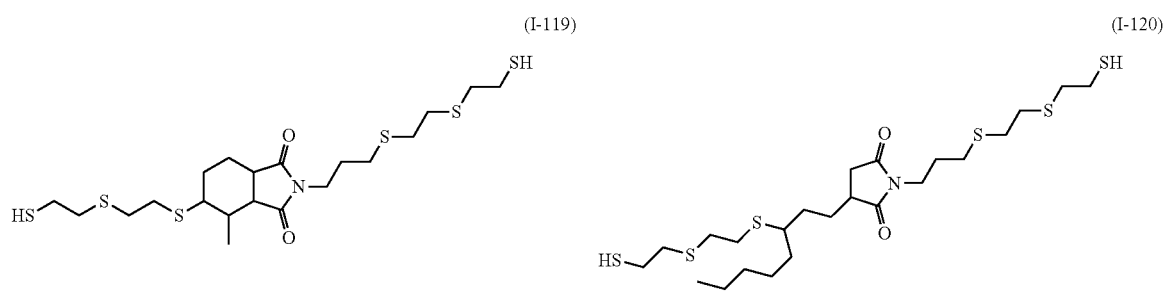

(I-121)
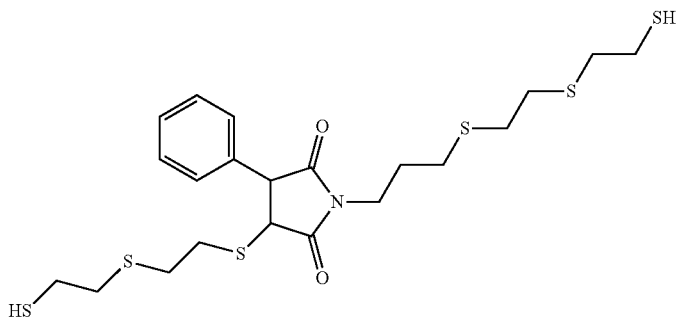
[Chem. 36]
(I-122)
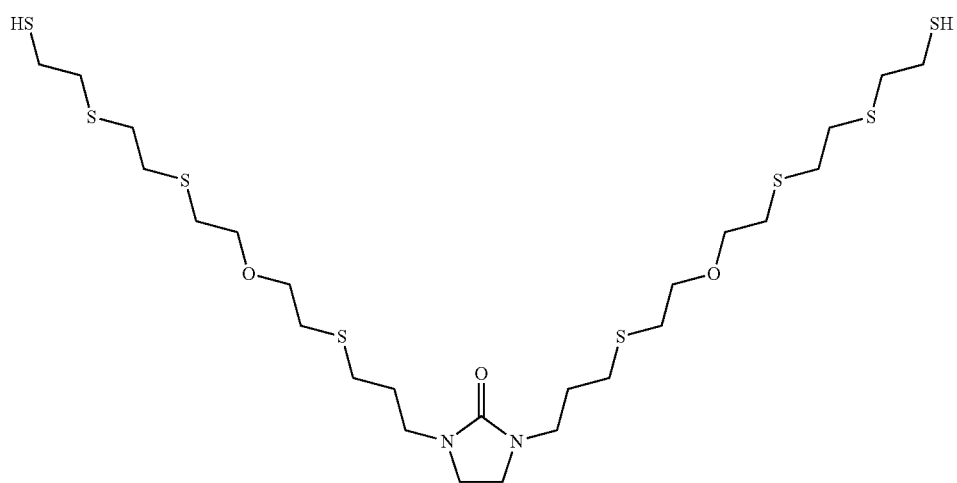
(I-123)
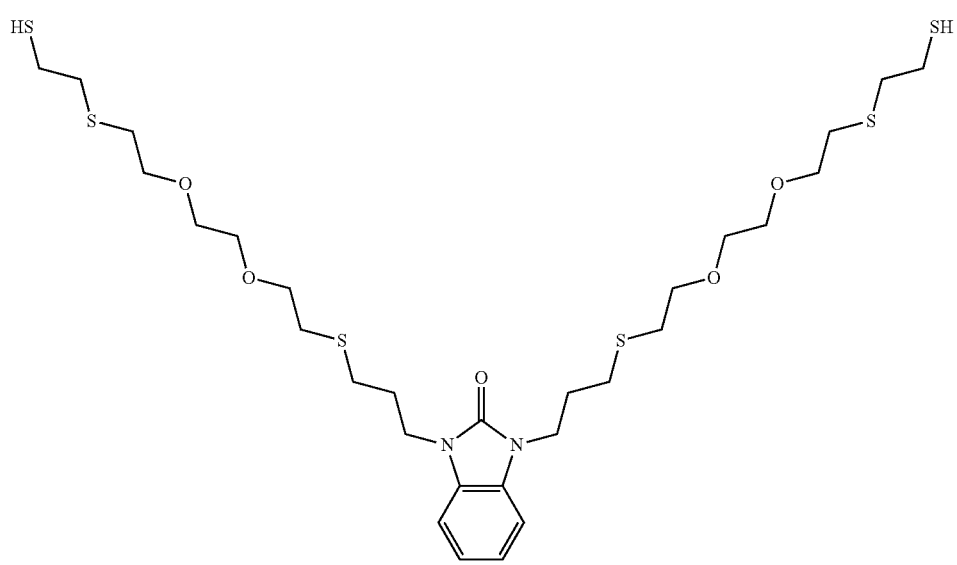

(I-124)
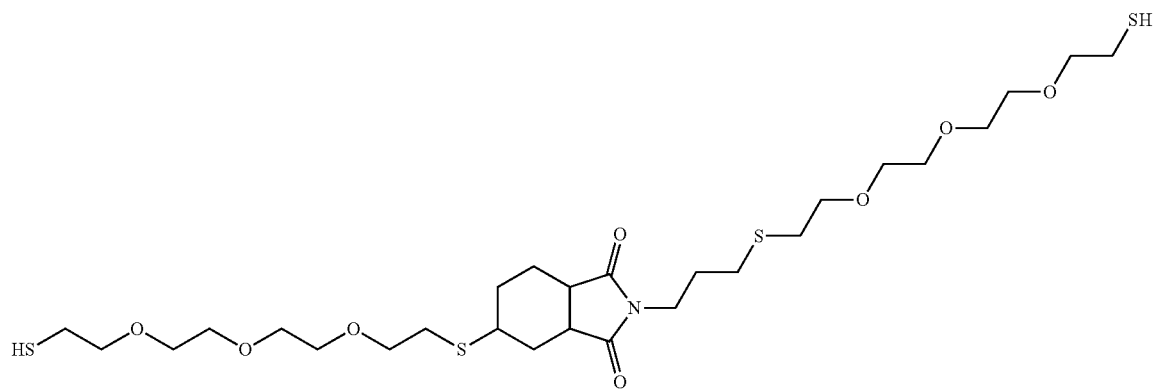
[Chem. 37]
(I-125)
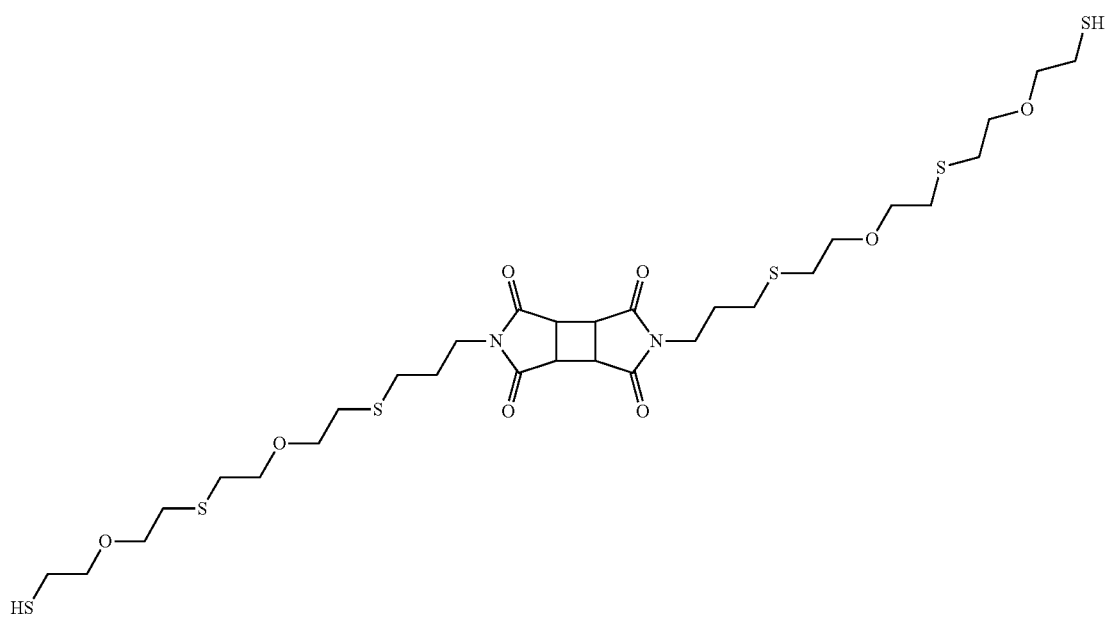
(I-126)
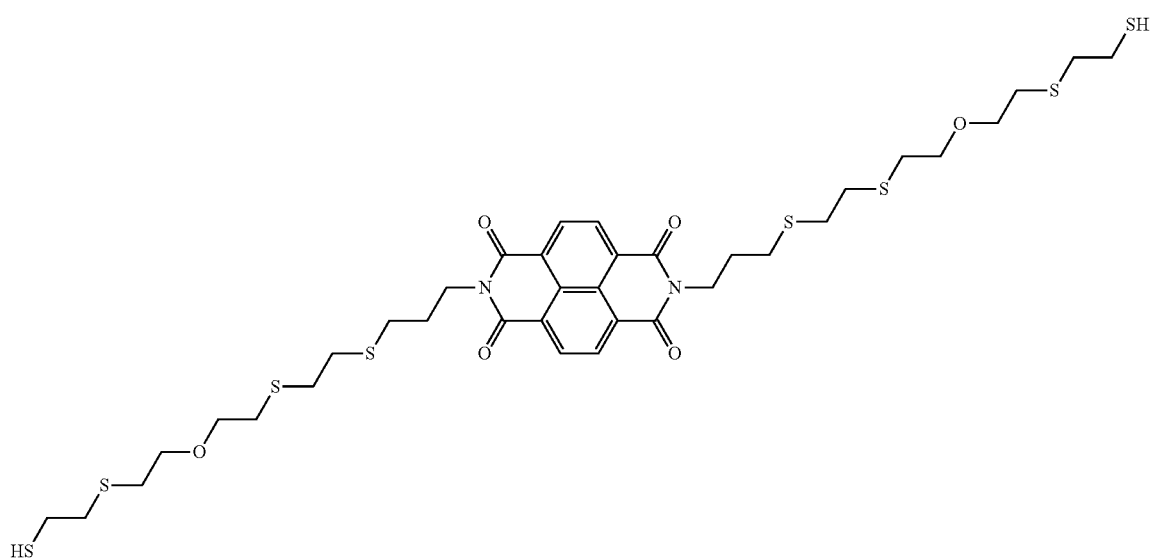

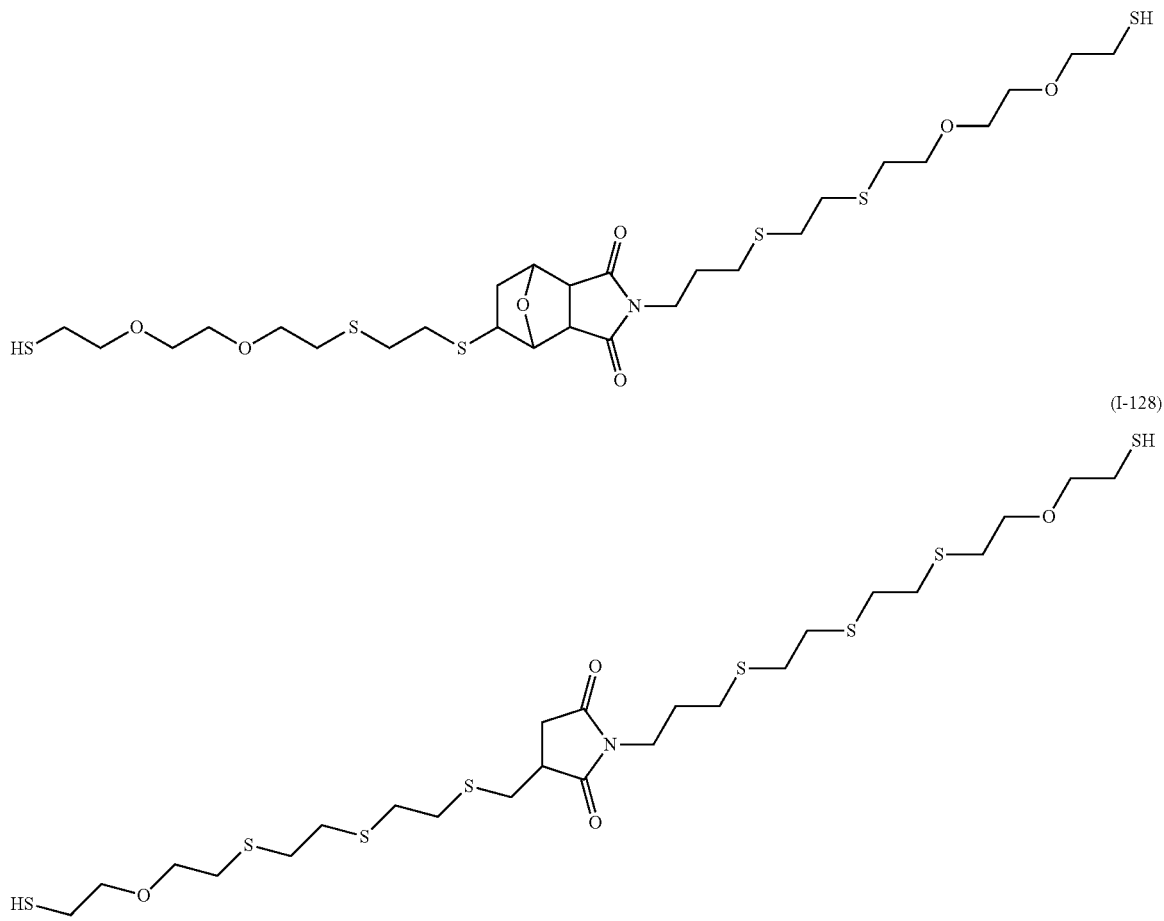

<Synthesis Method of Thiol Compound of the Present Invention>

The thiol compound represented by the chemical formula (I) in the present invention can be synthesized by reacting a dialkene compound represented by the above-mentioned chemical formula (B-1) to the chemical formula (B-23) (note: including the chemical formula (B-15a), the chemical formula (B-15b) and the chemical formula (B-15c)), that is, at least one dialkene compound selected from these dialkene compounds, with a thiol compound represented by the chemical formula (C-1) to the chemical formula (C-11), that is, at least one thiol compound selected from these thiol compounds.

Examples of the dialkene compound represented by the chemical formula (B-1) to the chemical formula (B-23) include dialkene compounds represented by the chemical formula (b-1) to the chemical formula (b-117).

[Chem. 38]

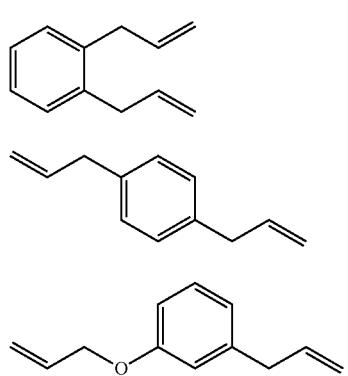

-continued
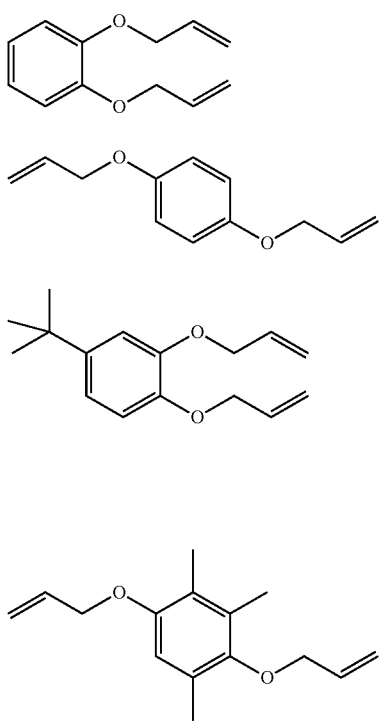
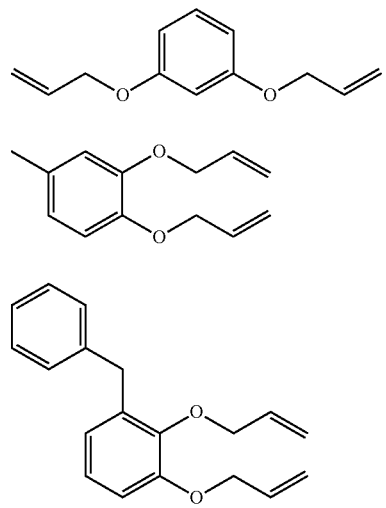
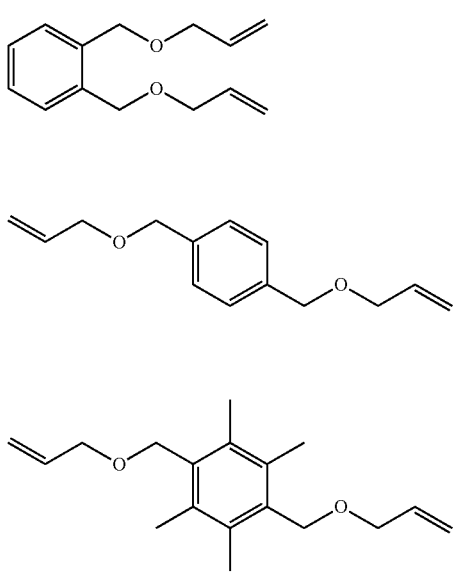
[Chem. 39]
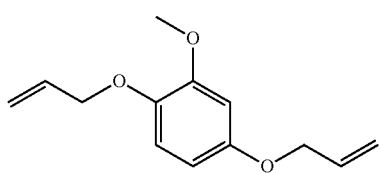

(b-22)
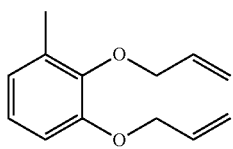
(b-23)
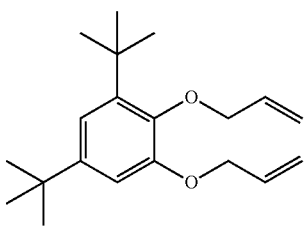
(b-24)
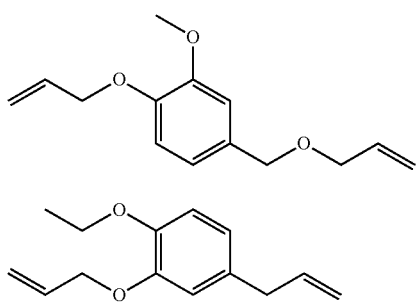
(b-25)
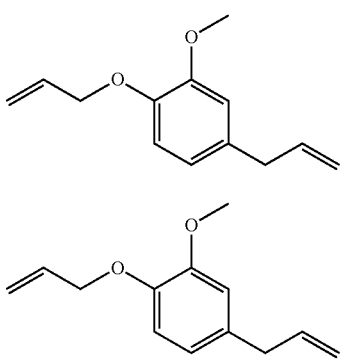
(b-26)
(b-27)
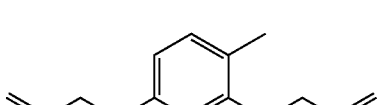
(b-28)
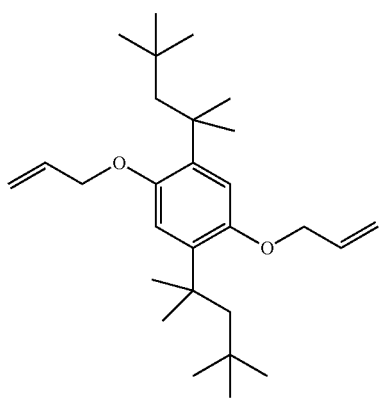
(b-29)
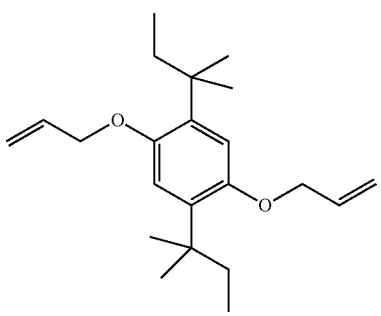
(b-30)
(b-31)
(b-32)
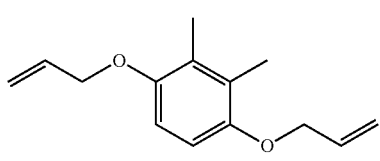
(b-33)
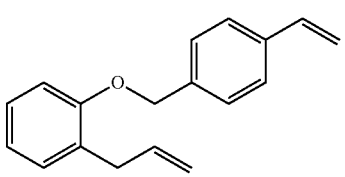
[Chem. 40]
(b-34)
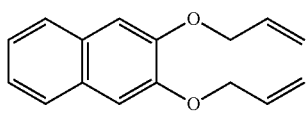
(b-35)
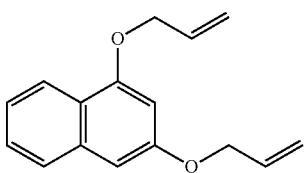

-continued
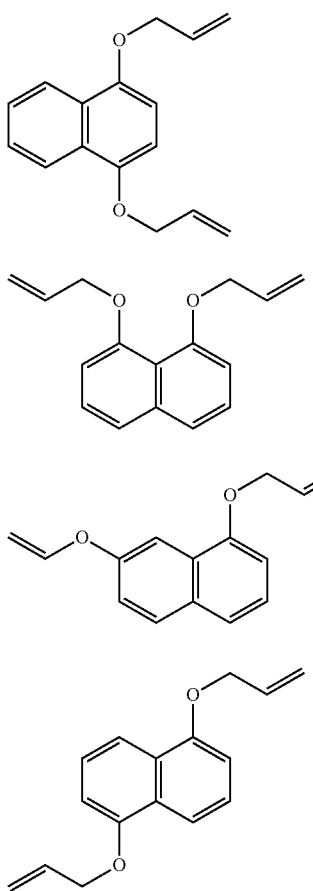
(b-36)
(b-38)
(b-40)
(b-42)
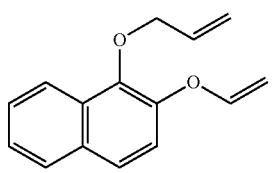
(b-37)
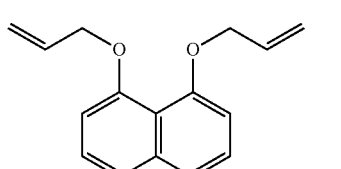
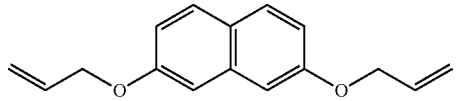
(b-39)
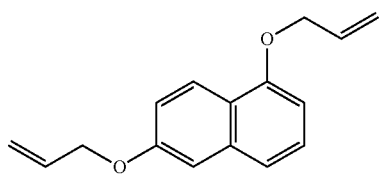
(b-41)
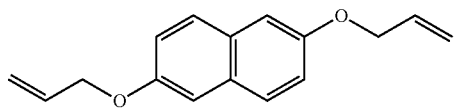
(b-43)
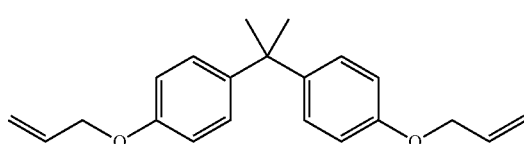
(b-44)
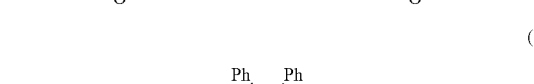
(b-45)
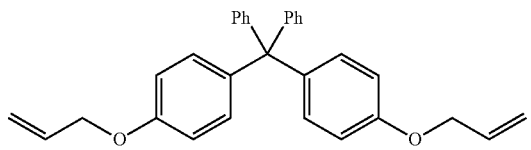
(b-46)
(b-47)
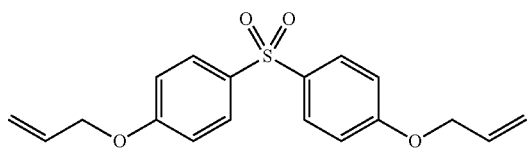
(b-48)
(b-49)
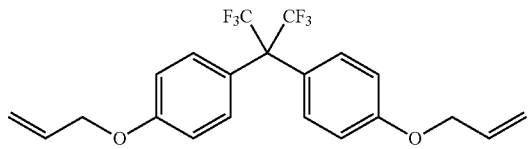
(b-50)
(b-51)

-continued
(b-52) 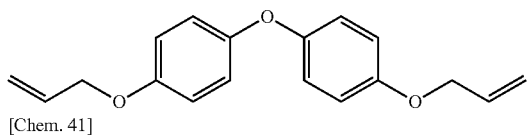
(b-53) 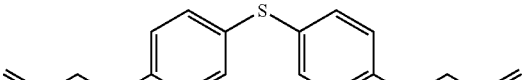
[Chem. 41]
(b-54) 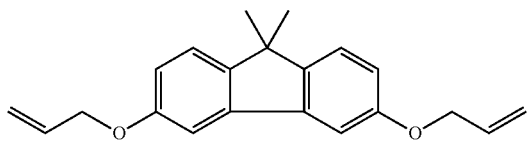
(b-55) 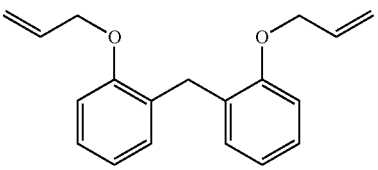
(b-56) 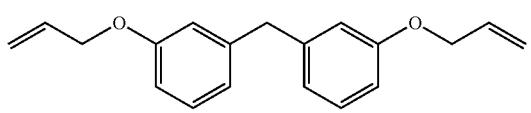
(b-57) 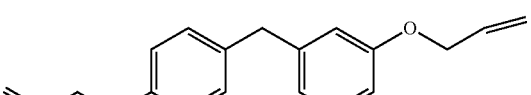
(b-58) 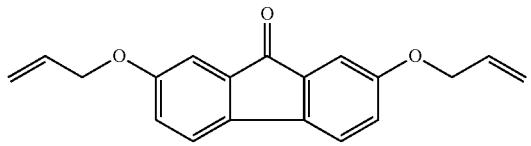
(b-59) 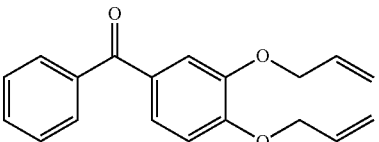
(b-60) 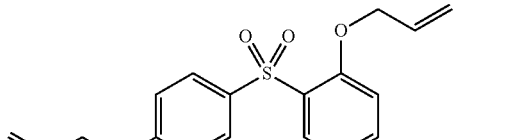
(b-61) 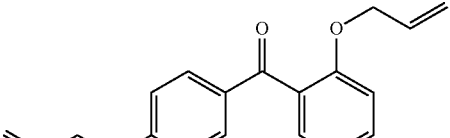
(b-62) 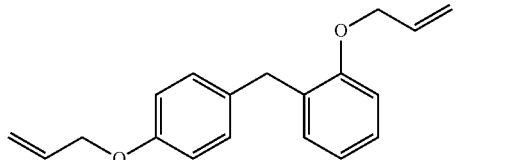
(b-63) 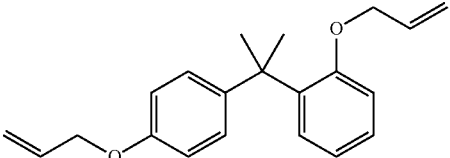
(b-64) 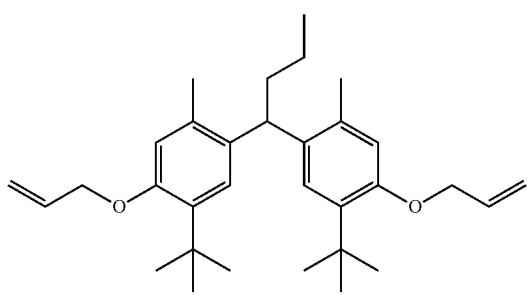
(b-65) 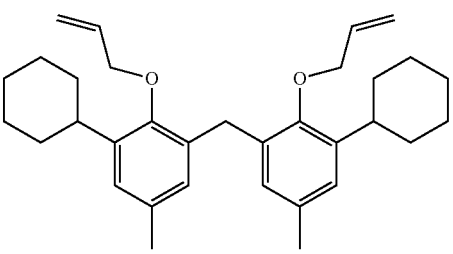
(b-66) 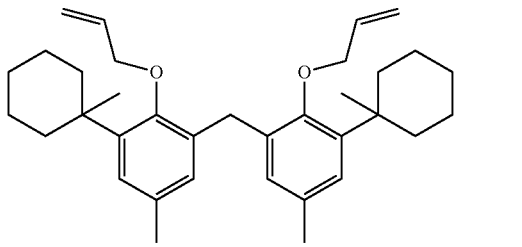
(b-67) 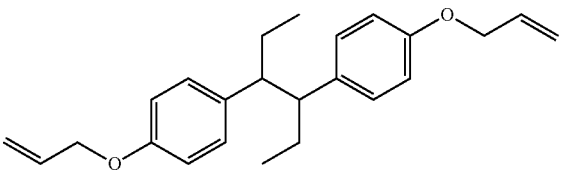

-continued
(b-68)
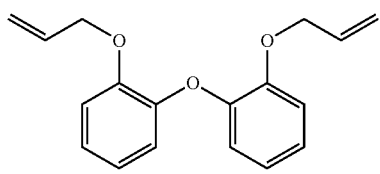
(b-69)
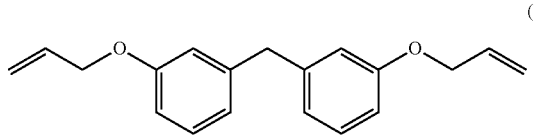
[Chem. 42]
(b-70)
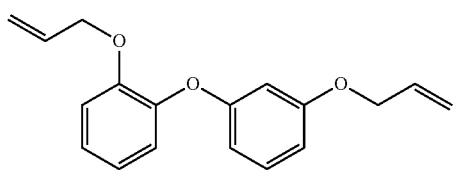
(b-71)
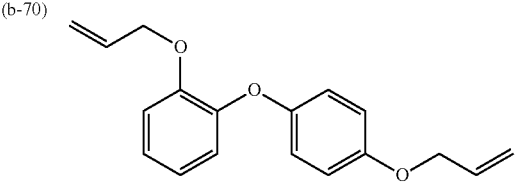
(b-72)
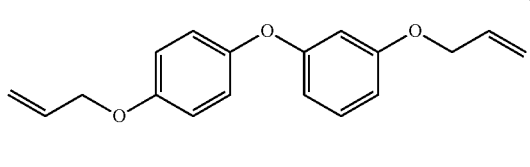
(b-73)
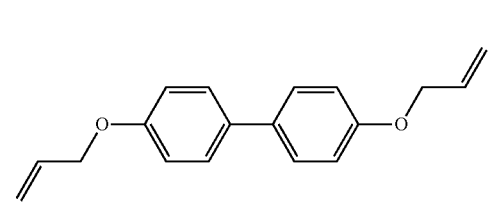
(b-74)
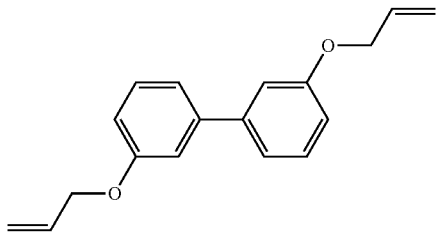
(b-75)
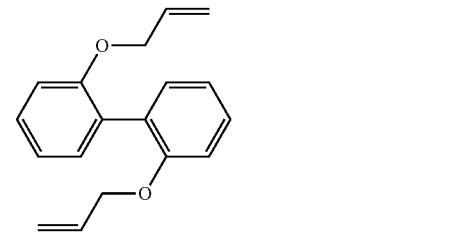
(b-76)
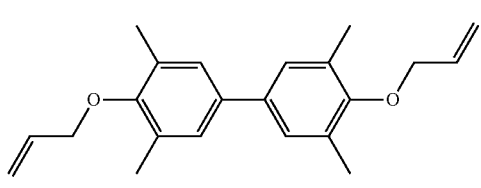
(b-77)
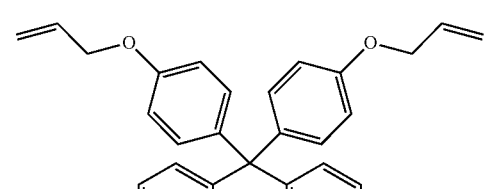
(b-78)
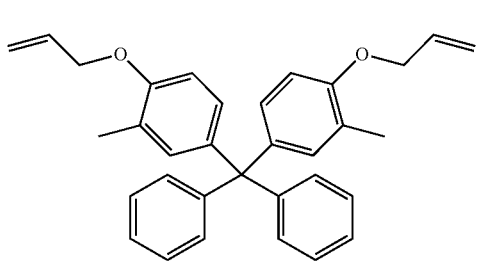
[Chem. 43]
(b-79)
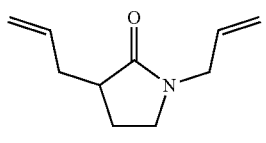
(b-80)
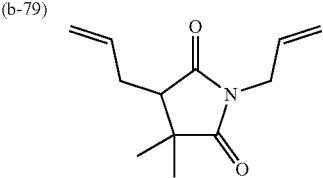

(b-81)
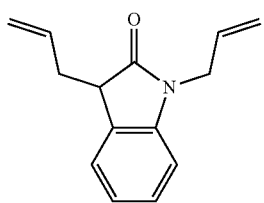
(b-82)
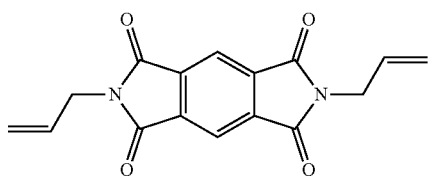
(b-83)
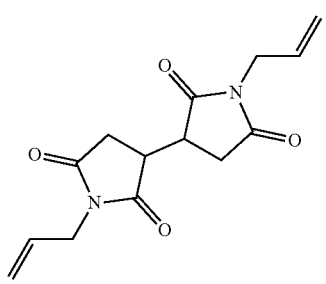
(b-84)
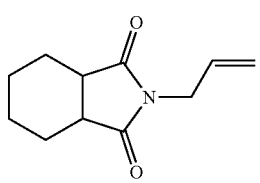
(b-85)
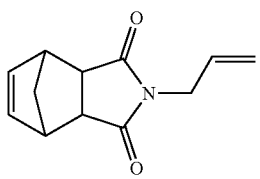
(b-86)
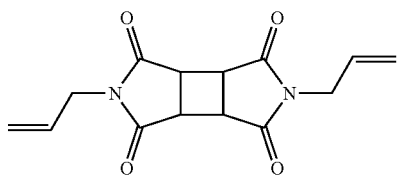
(b-87)
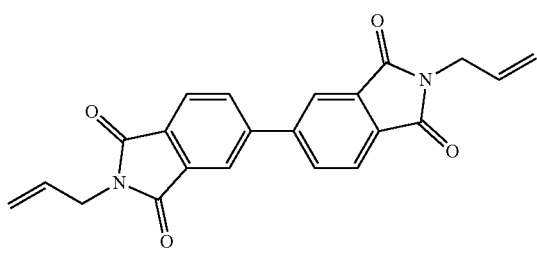
(b-88)
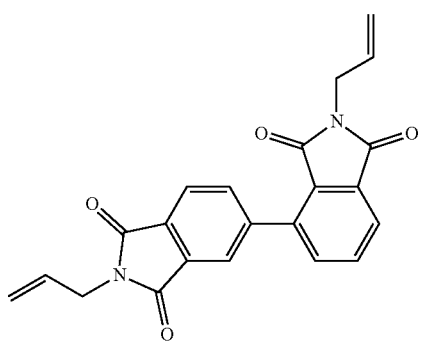
(b-89)
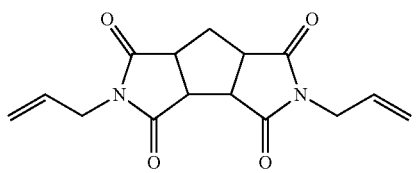
(b-90)
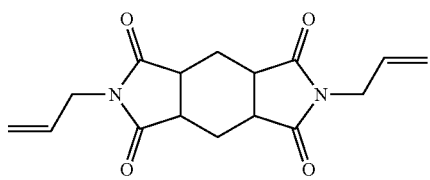
(b-91)
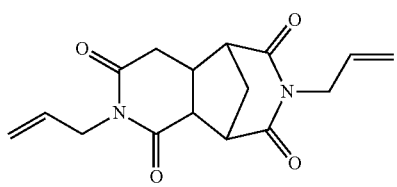
(b-92)
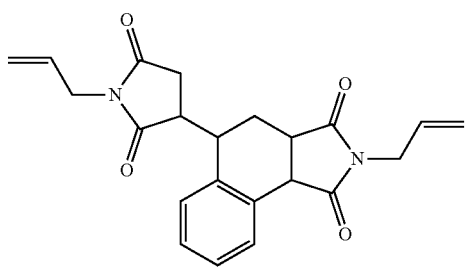

-continued
(b-93)
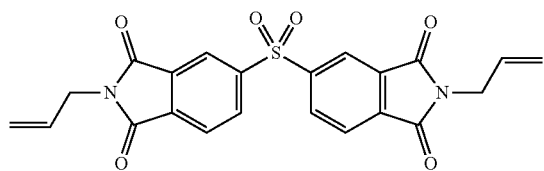
(b-94)
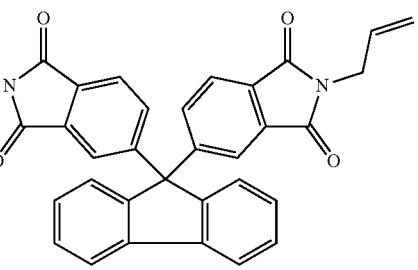
(b-95)
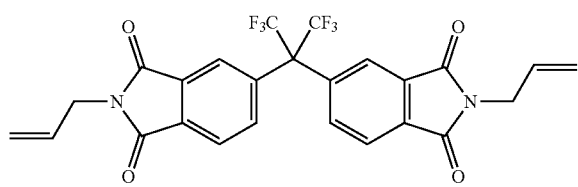
(b-96)
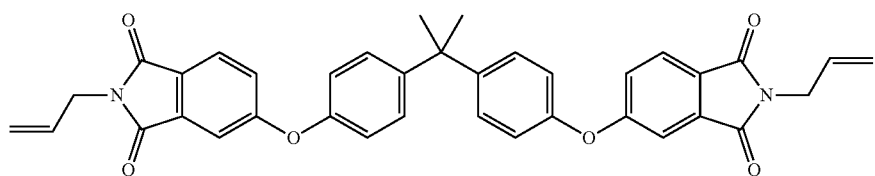
[Chem. 44]
(b-97)
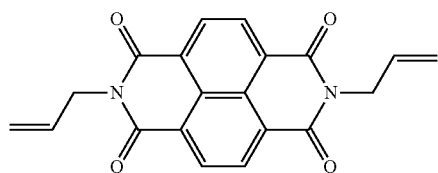
(b-98)
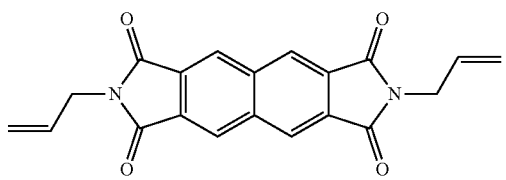
(b-99)
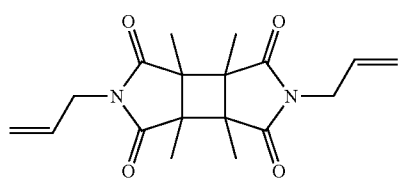
(b-100)
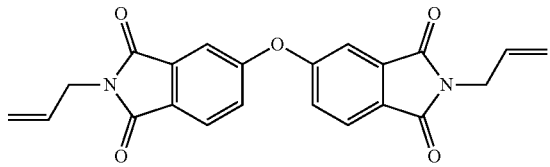
(b-101)
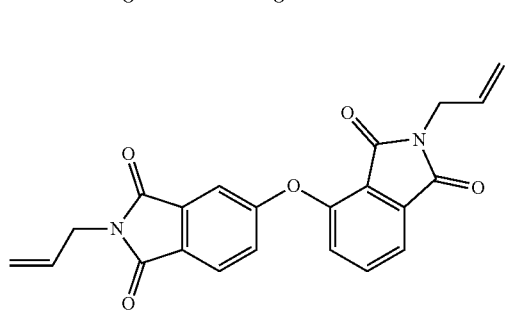
(b-102)
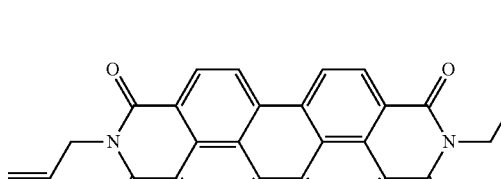
(b-103)
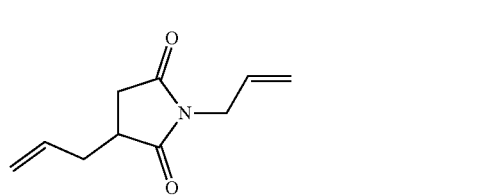
(b-104)
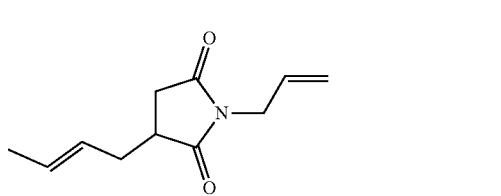

-continued
(b-105)
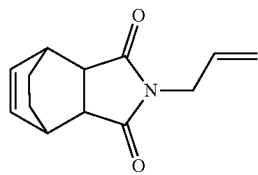
(b-106)
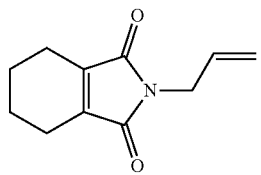
(b-107)
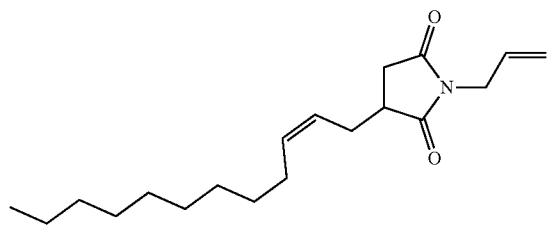
(b-108)
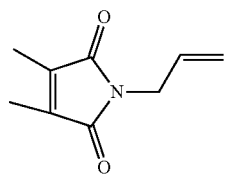
(b-109)
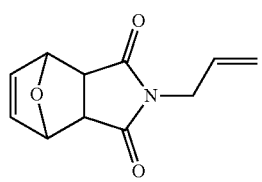
(b-110)
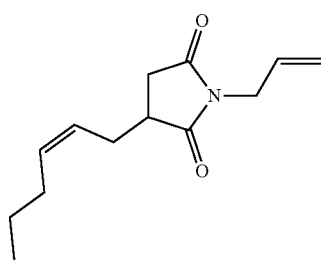
(b-111)
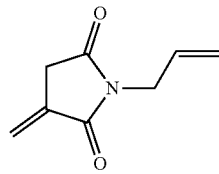
(b-112)
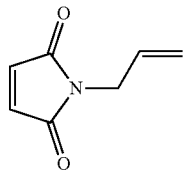
(b-113)
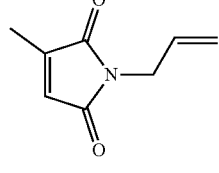
(b-114)
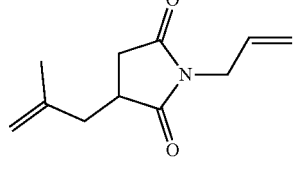
(b-115)
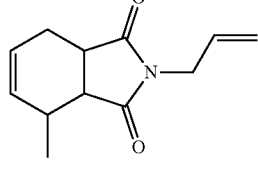
(b-116)
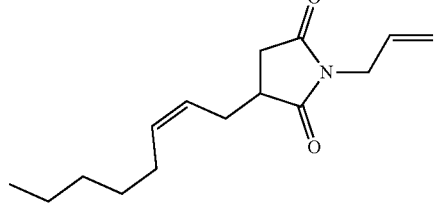
(b-117)
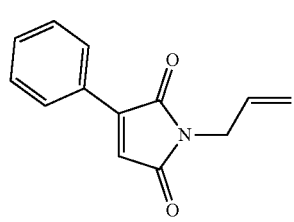

Among the thiol compounds of the present invention, a synthesis example in Example 1 described later is shown in the reaction scheme (A).

In this reaction scheme, the dialkene compound represented by the chemical formula (b-4) reacts with the thiol compound represented by the chemical formula (C-1) in double molar to produce the thiol compound represented by the chemical formula (I-17).

Reaction Scheme (A)

[Chem. 45]

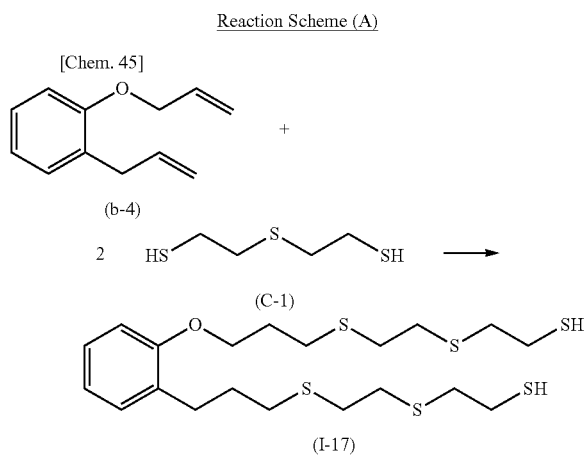

In carrying out the present invention, as the dialkene compound to be reacted with the thiol compound, different types of dialkene compounds may be used in combination, and similarly, as the thiol compound to be reacted with the dialkene compound, different types of thiol compounds may be used in combination. From the viewpoint of reducing the load in a product separation step or purification step, it is preferable to react one type of dialkene compound with one type of thiol compound.

The dialkene compound used in carrying out the present invention can be synthesized according to, for example, the methods described in J. Am. Chem. Soc., Vol. 81, pp. 2705-2715 (1959), Organic Letter, Vol. 19, pp. 6570-6573 (2017), International Publication No. 2002/036662, and the like.

As the thiol compounds represented by the chemical formula (C-1) to the chemical formula (C-3), the chemical formula (C-5), the chemical formula (C-6) and the chemical formula (C-9) among the thiol compounds used in carrying out the present invention, commercially available products can be used.

The thiol compounds represented by the chemical formula (C-4), the chemical formula (C-7), the chemical formula (C-8), the chemical formula (C-10), and the chemical formula (C-11) can be synthesized according to, for example, the methods described in Synthesis and Reactivity in Inorganic and Metal-Organic Chemistry, No. 29, Vol. 3, pp. 473-485 (1999).

The amount used (amount charged) of the above-mentioned thiol compound is preferably an appropriate ratio in a range of 2 to 100 molar times the amount used (amount charged) of the dialkene compound.

In the synthetic reaction of the thiol compound of the present invention, a radical initiator (A) may be used to accelerate the reaction. Furthermore, a reaction solvent (B) may be used in order to allow the reaction to proceed smoothly.

Examples of the radical initiator (A) include azobisisobutyronitrile, t-hexyl peroxyisopropyl monocarbonate, t-hexyl peroxy2-ethylhexanoate, 1,1,3,3-tetramethylbutyl peroxy2-ethylhexanoate, t-butylperoxypivalate, t-hexylperoxypivalate, t-butylperoxyneodecanoate, t-hexyl peroxyneodecanoate, 1,1,3,3-tetramethylbutylperoxyneodecanoate, 1,1-bis(t-hexylperoxy)cyclohexane, benzoyl peroxide, 3,5,5-trimethylhexanoyl peroxide, lauroyl peroxide, 2,2'-azobis(2-methylbutyronitrile), dimethyl 2,2'-azobis(2-methylpropionate), and the like.

The amount used (amount charged) of the radical initiator (A) is preferably an appropriate ratio in a range of 0.0001 to 10 molar times the amount used (amount charged) of the dialkene compound.

Examples of the reaction solvent (B) include solvents such as water, methanol, ethanol, propanol, 2-propanol, butanol, ethyl acetate, propyl acetate, butyl acetate, tetrahydrofuran, dioxane, acetonitrile, benzene, toluene, xylene, dichloromethane, chloroform, carbon tetrachloride, dimethylformamide, dimethylacetamide, dimethyl sulfoxide, and hexamethylphosphoric triamide. The reaction solvent (B) may be used alone or in combination of two or more thereof.

The reaction temperature in this synthetic reaction is preferably set to be in a range of 0° C. to 200° C. The reaction time is appropriately set according to the set reaction temperature, and is preferably set to be in a range of 1 hour to 120 hours.

After completion of the synthetic reaction, the target thiol compound of the present invention can be extracted from the obtained reaction liquid (reaction mixture) by, for example, the means such as concentration of the reaction liquid by distillation of the reaction solvent or a solvent extraction method.

As necessary, purification can be performed by utilizing the means such as cleaning with water or the like, treatment with activated carbon or silica gel chromatography.

The thiol compound of the present invention is preferably used as a curing agent for resins. That is, the curing agent of the present invention contains the thiol compound of the present invention.

In addition, the thiol compound of the present invention is also expected to be used as an intermediate raw material for various sulfur-containing compounds.

(First Resin Composition)

The first resin composition of the present invention is one obtained by adding the thiol compound of the present invention as a curing agent into an epoxy compound (note: refers to an epoxy resin before curing).

The epoxy compound can be used without particular limitation as long as it has an epoxy group (glycidyl group) in the molecule. Examples thereof include: polyglycidyl ethers (e.g., bisphenol A epoxy resins) obtained by reacting a polyhydric phenol such as bisphenol A, bisphenol F, bisphenol AD, catechol or resorcinol or a polyhydric alcohol such as glycerin or polyethylene glycol with epichlorohydrin;

glycidyl ether esters obtained by reacting a hydroxycarboxylic acid such as p-hydroxybenzoic acid or β-hydroxynaphthoic acid with epichlorohydrin;

polyglycidyl esters obtained by reacting a polycarboxylic acid such as phthalic acid or terephthalic acid with epichlorohydrin;

glycidyl glycoluril compounds having two or more epoxy groups in the molecule, such as 1,3,4,6-tetraglycidyl glycoluril;

cyclic alicyclic epoxy resins such as 3',4'-epoxycyclohexylmethyl-3,4-epoxycyclohexane carboxylate;

nitrogen-containing cyclic epoxy resins such as triglycidyl isocyanurate and a hydantoin epoxy resin; as well as epoxidized phenol novolac resins (phenol novolac epoxy resins), epoxidized cresol novolac resins, epoxidized polyolefins, cycloaliphatic epoxy resins, and urethane-modified epoxy resins;

additionally, epoxy-modified organopolysiloxane compounds obtained by a hydrosilylation addition reaction between an organic compound having a carbon-carbon double bond and a glycidyl group and a silicon compound having a SiH group (e.g., epoxy-modified organopolysiloxane compounds disclosed in JP-A-2004-99751 and JP-A-2006-282988); and the like. Those compounds may be used in combination.

The content of the thiol compound of the present invention in the first resin composition of the present invention is preferably set such that the ratio (equivalent ratio) of the number of the thiol group in the resin composition to the number of the epoxy group therein is 0.1 to 10.0.

In the first resin composition of the present invention, another thiol compound may be used together with the thiol compound of the present invention to form a curing agent. Examples of another thiol compound include:

aliphatic thiol compounds such as ethane dithiol, propane dithiol, hexamethylene dithiol, decamethylene dithiol, trilen-2,4-dithiol, 2,2-bis(mercaptomethyl)-1,3-propanedithiol, 2-(mercaptomethyl)-2-methyl-1,3-propanedithiol, and 2-ethyl-2-(mercaptomethyl)-1,3-propanedithiol;

aromatic thiol compounds such as benzenedithiol, toluenedithiol and xylenedithiol (p-xylenedithiol);

cyclic sulfide compounds such as a 1,4-dithiane ring-containing polythiol compound represented by the chemical formula (IV);

mercaptoalkyl sulfide compounds such as 3-thiapentane-1,5-dithiol and 4-mercaptomethyl-3,6-dithia-1,8-octanedithiol;

mercaptopropionic acid esters such as pentaerythritoltetrakis(3-mercaptopropionate);

epoxy resin-terminated mercapto compounds;

mercaptoalkyl ether compounds such as 3,6-dioxa-1,8-octanedithiol, a mercaptoalkyl ether disulfide compound represented by the chemical formula (V), 2,2'-[[2,2-bis[(2-mercaptoethoxy)methyl]-1,3-propanediyl]bis(oxy)]bisethanethiol, 3,3'-[[2,2-bis[(3-mercaptopropoxy)methyl]-1,3-propanediyl]bis(oxy)]bis-1-propanethiol, 3-[2,2-bis[(3-mercaptopropoxy)methyl]butoxy]-1-propanethiol, 3-(3-mercaptopropoxy)-2,2-bis[(3-mercaptopropoxy)methyl]-1-propanol, and 2,2-bis[(3-mercaptopropoxy)methyl]-1-butanol;

1,3,4,6-tetrakis(2-mercaptoethyl)glycoluril; and 1,3,4,6-tetrakis(3-mercaptopropyl)glycoluril. Those may be used in combination.

[Chem. 46]

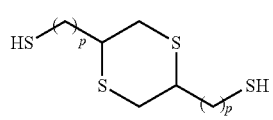

(IV)

(In the formula (IV), p represents an integer from 1 to 5.)

[Chem. 47]

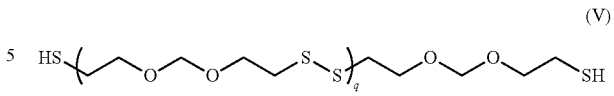

(V)

(In the formula (V), q represents an integer from 1 to 20.)

The content of another thiol compound in the first resin composition of the present invention is preferably set such that the ratio (equivalent ratio) of the number of the thiol group derived from another thiol compound in the composition to the number of the thiol group derived from the thiol compound of the present invention is 0 to 100.

The first resin composition of present invention may contain a conventionally-known curing agent together with the thiol compound of the present invention. Examples of the conventionally-known curing agent include:

compounds having a phenolic hydroxy group and acid anhydrides, as well as organic phosphine compounds such as triphenylphosphine, diphenylnaphthylphosphine and diphenylethylphosphine;

aromatic phosphonium salts;

aromatic diazonium salts;

aromatic iodonium salts;

aromatic selenium salts; and the like.

Examples of the compound having a phenolic hydroxy group include bisphenol A, bisphenol F, bisphenol S, tetramethylbisphenol A, tetramethylbisphenol F, tetramethylbisphenol S, tetrachlorobisphenol A, tetrabromobisphenol A, dihydroxynaphthalene, phenol novolac, cresol novolac, bisphenol A novoalc, brominated phenol novolac, resorcinol, and the like.

Examples of the acid anhydride include methyltetrahydrophthalic anhydride, methylhexahydrophthalic anhydride, hexahydrophthalic anhydride, 5-norbornene-2,3-dicarboxylic anhydride, trimellitic anhydride, nadic anhydride, hymic anhydride, methylnadic anhydride, methylbicyclo[2.2.1]heptane-2,3-dicarboxylic anhydride, bicyclo[2.2.1]heptane-2,3-dicarboxylic anhydride, methylnorbornane-2,3-dicarboxylic acid, and the like.

The first resin composition of the present invention may contain a conventionally-known curing accelerator. Examples of the curing accelerator include (i) amines (hereinafter, may be referred to as a component (i)), (ii) reaction products between an epoxy compound and an amine (hereinafter, may be referred to as a component (ii)), (iii) reaction products between a compound having one or more isocyanate group in the molecule and a compound having at least any of a primary amino group and a secondary amino group in the molecule (hereinafter, may be referred to as a component (iii)), and the like. Those may be used in combination.

Any amine suffices as the component (i) as long as it has at least one amino group selected from a primary amino group, a secondary amino group and a tertiary amino group in the molecule, as conventionally known.

Examples of the amine include:

aliphatic amines such as diethylenetriamine, triethylenetetramine, n-propylamine, 2-hydroxyethylaminopropylamine, cyclohexylamine, 4,4'-diaminodicyclohexylmethane, and dimethylbenzylamine;

aromatic amines such as 4,4'-di aminodiphenylmethane and o-methylaniline;

nitrogen-containing heterocyclic compounds such as 2-ethyl-4-methylimidazole, 2-methylimidazole, 2-ethyl-4-methylimidazoline, 2,4-dimethylimidazoline, piperidine, and piperazine; and the like.

The content of the component (i) in the first resin composition of the present invention is preferably 0.1 to 100 parts by weight per 100 parts by weight of the epoxy compound (epoxy resin).

The component (ii) is a solid hardly soluble in an epoxy resin at room temperature, solubilizes (easily solubilizes) by heating and functions as a curing accelerator. Therefore, it is also called a latent curing accelerator (the component (ii) is hereinafter sometimes referred as a "latent curing accelerator").

Examples of the epoxy compound used as a raw material of the latent curing accelerator include:

the epoxy compounds described above; as well as glycidylamine compounds obtained by reacting 4,4'-diaminodiphenylmethane, m-aminophenol or the like with epichlorohydrin;

monofunctional epoxy compounds such as butylglycidyl ether, phenylglycidyl ether, and glycidyl methacrylate; and the like.

Examples of the amine used as a raw material of the latent curing accelerator include the amines described above. Among those amines, amines having a tertiary amino group in the molecule are raw materials capable of giving a latent curing accelerator having excellent curing accelerating properties. Examples of such amines include:

amines such as dimethylaminopropylamine, diethylaminopropylamine, di-n-propylaminopropylamine, dibutylaminopropylamine, dimethylaminoethylamine, diethylaminoethylamine, and N-methylpiperazine;

amines having a tertiary amino group in the molecule, such as imidazole compounds such as 2-methylimidazole, 2-ethylimidazole, 2-ethyl-4-methylimidazole, and 2-phenylimidazole;

alcohols, phenols, thiols, carboxylic acids, and hydrazides, having a tertiary amino group in the molecule, such as 2-dimethylaminoethanol, 1-methyl-2-dimethylaminoethanol, 1-phenoxymethyl-2-dimethylaminoethanol, 2-diethylaminoethanol, 1-butoxymethyl-2-dimethylaminoethanol, 1-(2-hydroxy-3-phenoxypropyl)-2-methylimidazole, 1-(2-hydroxy-3-phenoxypropyl)-2-ethyl-4-methylimidazole, 1-(2-hydroxy-3-butoxypropyl)-2-methylimidazole, 1-(2-hydroxy-3-butoxypropyl)-2-ethyl-4-methylimidazole, 1-(2-hydroxy-3-phenoxypropyl)-2-phenylimidazoline, 1-(2-hydroxy-3-butoxypropyl)-2-methylimidazoline, 2-(dimethylaminomethyl)phenol, 2,4,6-tris(dimethylaminomethyl)phenol, N-β-hydroxyethyl morpholine, 2-dimethylaminoethanethiol, 2-mercaptopyridine, 2-mercaptobenzimidazole, 2-mercaptobenzothiazole, 4-mercaptopyridine, N,N-dimethylaminobenzoic acid, N,N-dimethylglycine, nicotinic acid, isonicotinic acid, picolinic acid, N,N-dimethylglycine hydrazide, N,N-dimethylpropionic acid hydrazide, nicotinic acid hydrazide, and isonicotinic acid hydrazide; and the like.

In addition to the epoxy compound and the amines, an active hydrogen compound having two or more active hydrogens in the molecule can be used as a third component as the raw material of the latent curing accelerator in order to further improve storage stability of the first resin composition of the present invention.

Examples of the active hydrogen compound include:

polyhydric phenols such as bisphenol A, bisphenol F, bisphenol S, hydroquinone, catechol, resorcinol, pyrogallol, and a phenol novolac resin;

polyhydric alcohols such as trimethylolpropane;

polyhydric carboxylic acids such as adipic acid and phthalic acid; or 1,2-dimercaptoethane, 2-mercaptoethanol, 1-mercapto-3-phenoxy-2-propanol, mercaptoacetic acid, anthranilic acid, lactic acid, and the like.

The latent curing accelerator may be surface-treated with an isocyanate compound or an acidic compound. Examples of the isocyanate compound include:

monofunctional isocyanate compounds such as n-butyl isocyanate, isopropyl isocyanate, phenyl isocyanate, and benzyl isocyanate; and polyfunctional isocyanate compounds such as hexamethylene diisocyanate, toluylene diisocyanate, 1,5-naphthalene diisocyanate, diphenylmethane-4,4'-diisocyanate, isophorone diisocyanate, xylene diisocyanate, paraphenylene diisocyanate, 1,3,6-hexamethylene triisocyanate, and bicycloheptane triisocyanate.

In place of the polyfunctional isocyanate compound, a terminal isocyanate group-containing compound obtained by a reaction between a polyfunctional isocyanate compound and an active hydrogen compound can also be used. Specific examples thereof include an addition reaction product having a terminal isocyanate group, obtained by a reaction between toluylene diisocyanate and trimethylolpropane, an addition reaction product having a terminal isocyanate group, obtained by a reaction between toluylene diisocyanate and pentaerythritol, and the like.

The acidic substance used in the surface treatment of the latent curing accelerator may be any of gas, liquid and solid, and may be any of an inorganic acid and an organic acid. Examples of the acidic substance include carbon dioxide gas, sulfurous acid gas, sulfuric acid, hydrochloric acid, oxalic acid, phosphoric acid, acetic acid, formic acid, propionic acid, adipic acid, caproic acid, lactic acid, succinic acid, tartaric acid, sebacic acid, p-toluenesulfonic acid, salicylic acid, boric acid, tannic acid, alginic acid, polyacrylic aid, polymethacrylic acid, phenol, pyrogallol, phenol resins, resorcin resins, and the like.

The latent curing accelerator can be easily obtained by mixing an epoxy compound, an amine and as necessary, an active hydrogen compound, and reacting the resulting mixture at a temperature of room temperature to 200° C. and then, solidifying and pulverizing, or reacting those compounds in a solvent such as methyl ethyl ketone, dioxane or tetrahydrofuran, removing the solvent and pulverizing the solid component.

A commercially available latent curing accelerator can be used. Examples of the commercially available product include "AMICURE PN-23 (trade name)", "AMICURE PN-H (trade name)" and "AMICURE MY-24 (trade name)", manufactured by Ajinomoto Fine-Techno Co., Inc., and "NOVACURE HX-3721 (trade name)" and "NOVACURE HX-3742 (trade name)", manufactured by Asahi Kasei Corporation.

The content of the latent curing accelerator (component (ii)) in the first resin composition of the present invention is preferably 0.1 to 1,000 parts by weight per 100 parts by weight of the epoxy compound (epoxy resin).

The component (iii) can be obtained by reacting the compound having one or more isocyanate groups in the molecule with the compound having at least any of a primary amino group and a secondary amino group in the molecule in an organic solvent such as dichloromethane.

Examples of the compound having one or more isocyanate groups in the molecule include n-butyl isocyanate, isopropyl isocyanate, 2-chloroethyl isocyanate, phenyl isocyanate, p-bromophenyl isocyanate, m-chlorophenyl isocyanate, o-chlorophenyl isocyanate, p-chlorophenyl isocyanate, 2,5-dichlorophenyl isocyanate, 3,4-dichlorophenyl isocyanate, 2,6-dimethylphenyl isocyanate, o-fluorophenyl isocyanate, p-fluorophenyl isocyanate, m-tolyl isocyanate, p-tolyl isocyanate, o-trifluoromethylphenyl isocyanate, m-trifluoromethylphenyl isocyanate, benzyl isocyanate, hexamethylene diisocyanate, 2,4-toluylene diisocyanate, 2,6-toluylene diisocyanate, 1,5-naphthalene diisocyanate, diphenylmethane-4,4'-diisocyanate, 2,2-dimethyldiphenylmethane-4,4'-diisocyanate, tolidine diisocyanate, isophorone diisocyanate, xylylene diisocyanate, 1,3-bis(isocyanatemethyl)-cyclohexane, p-phenylene diisocyanate, 1,3,6-hexamethylene triisocyanate, bicycloheptane triisocyanate, tris-(3-isocyanato-4-methylphenyl)isocyanurate, and tris-(6-isocyanatohexyl)isocyanurate.

Examples of the compound having at least any of a primary amino group and a secondary amino group in the molecule include dimethylamine, diethylamine, di-n-propylamine, di-n-butylamine, di-n-hexylamine, di-n-octylamine, di-n-ethanolamine, dimethylaminopropylamine, di ethyl aminopropylamine, morpholine, piperidine, 2,6-dimethylpiperidine, 2,2,6,6-tetramethylpiperidine, piperazine, pyrrolidine, benzylamine, N-methylbenzylamine, cyclohexylamine, m-xylylenediamine, 1,3-bis(aminomethyl)cyclohexane, isophorone diamine, N-aminoethylpiperazine, 2-methylimidazole, 2-ethyl-4-methylimidazole, 2-undecylimidazole, 2-phenylimidazole, 1,1-dimethylhydrazine, and the like.

The content of the component (iii) in the first resin composition of the present invention is preferably 1 to 10 parts by weight per 100 parts by weight of the epoxy compound (epoxy resin).

As necessary, the first resin composition of the present invention may contain the following materials in a proportion of 0.01 wt % to 50 wt % based on the entire first resin composition (total amount) so long as the effect of the present invention is not impaired:

a pigment (titanium white, cyanine blue, watching red, red iron oxide, carbon black, aniline black, manganese blue, iron black, ultramarine blue, Hansa red, chrome yellow, chrome green, etc.);

an inorganic filler (calcium carbonate, kaolin, clay, talc, mica, barium sulfate, lithopone, gypsum, zinc stearate, perlite, quartz, quartz glass, fused silica, silica powder such as spherical silica, oxides such as spherical alumina, pulverized alumina, magnesium oxide, beryllium oxide, and titanium oxide, nitrides such as boron nitride, silicon nitride and aluminum nitride, carbides such as silicon carbide, hydroxides such as aluminum hydroxide and magnesium hydroxide, metals such as copper, silver, iron, aluminum, nickel, and titanium, and alloys thereof, carbonaceous materials such as diamond and carbon, etc.);

a thermoplastic resin and/or thermosetting resin (various polyethylenes having high density, medium density and low density, homopolymers such as polypropylene, polybutene and polypentene, ethylene-propylene copolymers, polyamide resins such as nylon-6 and nylon-6,6, vinyl chloride resins, nitrocellulose resins, vinylidene chloride resins, acrylic resins, acrylamide resins, styrene resins, vinyl ester resins, polyester resins, phenol resins (phenol compounds), silicone resins, fluorine resins, various elastomer resins such as acryl rubber and urethane rubber, graft copolymers such as a methyl methacrylate-butadiene-styrene graft copolymer and a acrylonitrile-butadiene-styrene graft copolymer, etc.);

a reinforcing agent (glass fiber, carbon fiber, etc.);

an anti-sagging agent (hydrogenated castor oil, silicic anhydride fine particles, etc.);

a matting agent (silica fine powder, paraffin wax, etc.);

an abrasive (zinc stearate, etc.);

an internal mold release agent (fatty acids such as stearic acid, fatty acid metal salts such as calcium stearate, fatty acid amides such as stearic acid amide, fatty acid esters, polyolefin wax, paraffin wax, etc.); and an additive (modifier) such as a surfactant, a leveling agent, a defoaming agent, a diluent for viscosity adjustment (organic solvent), a flexibilizer, a coupling agent, perfume, a flame retardant, and an anti-oxidant.

In the first resin composition of the present invention, in the case where an isocyanate group-containing compound is contained as an additive (modifier), adhesive force can be enhanced while preventing the deterioration of the curability of the resin composition.

Examples of the isocyanate group-containing compound include n-butyl isocyanate, isopropyl isocyanate, 2-chloroethyl isocyanate, phenyl isocyanate, p-chlorophenyl isocyanate, benzyl isocyanate, hexamethylene diisocyanate, 2-ethylphenyl isocyanate, 2,6-dimethylphenyl isocyanate, 2,4-toluene diisocyanate, 2,6-toluene diisocyanate, 1,5-naphthalene diisocyanate, diphenylmethane-4,4'-diisocyanate, tolidine diisocyanate, isophorone diisocyanate, xylylene diisocyanate, p-phenylene diisocyanate, 1,3,6-hexamethylene triisocyanate, bicycloheptane triisocyanate, and the like.

The content of the isocyanate group-containing compound in the first resin composition of the present invention is preferably 0.1 to 20 parts by weight per 100 parts by weight of the epoxy compound (epoxy resin).

A method for preparing (mixing) the first resin composition of the present invention is not particularly limited. Predetermined amounts of the respective components described above are weighed and those components can be mixed by using an appropriate stirring/mixing apparatus such as triple roll mill and planetary mixer while heating as necessary.

A method for curing the first resin composition of the present invention is not particularly limited and use can be made of a conventionally-known curing apparatus such as a closed curing furnace and a tunnel furnace capable of performing continuous curing. The heating source is also not particularly limited, and use can be made of a conventionally-known means such as hot air circulation, infrared heating and high frequency heating. The curing temperature and the curing time can be appropriately set.

(Second Resin Composition)

The second resin composition of the present invention contains the thiol compound of the present invention and an enic compound having a carbon-carbon double bond in the molecule (hereinafter simply referred to as an "enic compound").

The enic compound includes both a polymerizable monomer and a polymerizable oligomer (semi-cured product) having a structure that a polymerizable monomer has been partially polymerized.

Examples of the polymerizable monomer include:
(1) a (meth)acrylic acid alkyl ester monomer;
(2) a hydroxy group-containing monomer;

(3) a carboxyl group-containing monomer;
(4) an amino group-containing monomer;
(5) an acetoacetyl group-containing monomer;
(6) an isocyanate group-containing monomer;
(7) a glycidyl group-containing monomer;
(8) a monomer having one aromatic ring;
(9) a monomer having an alkoxy group and an oxyalkylene group;
(10) an alkoxyalkyl (meth)acrylamide monomer;
(11) a (meta)acrylamide monomer;
(12) a monofunctional unsaturated compound;
(13) a polyfunctional unsaturated compound; and the like.

(1) Examples of the (meth)acrylic acid alkyl ester monomer include
methyl (meth)acrylate,
ethyl (meth)acrylate,
n-butyl (meth)acrylate,
iso-butyl (meth)acrylate,
tert-butyl (meth)acrylate,
n-propyl (meth)acrylate,
n-hexyl (meth)acrylate,
2-ethylhexyl (meth)acrylate,
n-octyl (meth)acrylate,
isodecyl (meth)acrylate,
lauryl (meth)acrylate,
cetyl (meth)acrylate,
stearyl (meth)acrylate,
cyclohexyl (meth)acrylate,
isobornyl (meth)acrylate, and the like.

(2) Examples of the hydroxy group-containing monomer include:
(meth)acrylic acid hydroxyalkyl esters such as:
2-hydroxyethyl (meth)acrylate,
4-hydroxybutyl (meth)acrylate,
5-hydroxypentyl (meth)acrylate,
6-hydroxyhexyl (meth)acrylate, and
8-hydroxyoctyl (meth)acrylate;
caprolactone-modified monomers such as caprolactone-modified 2-hydroxyethyl (meth)acrylate;
oxyalkylene-modified monomers such as
diethylene glycol (meth)acrylate, and
polyethylene glycol (meth)acrylate; as well as
primary hydroxy group-containing monomers such as
2-acryloyloxyethyl 2-hydroxyethyl phthalic acid,
N-methylol (meth)acrylamide, and
hydroxyethyl acryl amide;
secondary hydroxy group-containing monomers such as
2-hydroxypropyl (meth)acrylate,
2-hydroxybutyl (meth)acrylate,
3-chloro-2-hydroxypropyl (meth)acrylate,
propyleneglycol diglycidyl ether-epoxydi(meth)acrylate,
phenol glycidyl ether-epoxy(meth)acrylate, and
bisphenol A diglycidyl ether-epoxydi(meth)acrylate;
tertiary hydroxy group-containing monomers such as 2,2-dimethyl 2-hydroxyethyl (meth)acrylate; and the like.

(3) Examples of the carboxyl group-containing monomer include
(meth)acrylic acid, acrylic acid dimer, crotonic acid, maleic acid, maleic anhydride, fumaric acid, citraconic acid, glutaconic acid, itaconic acid, acrylamide N-glycolic acid, cinnamic acid, and the like.

(4) Examples of the amino group-containing monomer include
tert-butylaminoethyl (meth)acrylate,
ethylaminoethyl (meth)acrylate,
dimethylaminoethyl (meth)acrylate,
diethylaminoethyl (meth)acrylate, and the like.

(5) Examples of the acetoacetyl group-containing monomer include
2-(acetoacetoxy)ethyl (meth)acrylate,
allyl acetoacetate, and the like.

(6) Examples of the isocyanate group-containing monomer include
2-acryloyloxyethyl isocyanate,
2-methacryloyloxyethyl isocyanate,
alkylene oxide adducts thereof, and the like.

(7) Examples of the glycidyl group-containing monomer include
glycidyl (meth)acrylate, as well as
ethylene glycol diglycidyl ether-epoxy(meth)acrylate,
resorcin diglycidyl ether-epoxy(meth)acrylate,
bis(4-hydroxyphenyl)sulfide diglycidyl ether-epoxy(meth)acrylate,
phenol novolac epoxy resin-(meth)acrylate,
cresol novolac epoxy resin-(meth)acrylate,
bisphenol (e.g., bisphenol A or bisphenol F) epoxy resin-(meth)acrylate,
biphenol (e.g., 3,3',5,5'-tetramethyl biphenol) epoxy resin-(meth)acrylate,
epoxy(meth)acrylates, which are reaction products between an epoxy compound such as tris(2,3-epoxypropyl) isocyanurate-(meth)acrylate and (meth)acrylic acid, and
glycidyl (meth)acrylates such as 4-hydroxybutyl(meth)acrylate glycidyl ether.

(8) Examples of the monomer having one aromatic ring include
phenyl (meth)acrylate,
benzyl (meth)acrylate,
phenoxyethyl (meth)acrylate,
phenoxydiethylene glycol (meth)acrylate,
2-hydroxy-3-phenoxypropyl (meth)acrylate,
styrene,
α-methylstyrene, and the like.

(9) Examples of the monomer having an alkoxy group and an oxyalkylene group include
2-methoxyethyl (meth)acrylate,
2-ethoxyethyl (meth)acrylate,
3-methoxybutyl (meth)acrylate,
2-butoxyethyl (meth)acrylate,
2-butoxydiethylene glycol (meth)acrylate,
methoxydiethylene glycol (meth)acrylate,
methoxytriethylene glycol (meth)acrylate,
ethoxydiethylene glycol (meth)acrylate,
methoxydipropylene glycol (meth)acrylate,
methoxypolyethylene glycol (meth)acrylate,
octoxypolyethylene glycol-polypropylene glycol-mono (meth)acrylate,
lauroxypolyethylene glycol mono(meth)acrylate,
stearoxypolyethylene glycol mono(meth)acrylate, and the like.

(10) Examples of the alkoxyalkyl (meth)acrylamide monomer include
methoxymethyl (meth)acrylamide,
ethoxymethyl (meth)acrylamide,
propoxymethyl (meth)acrylamide,
isopropoxymethyl (meth)acrylamide,
n-butoxymethyl (meth)acrylamide,
isobutoxymethyl (meth)acrylamide, and the like.

(11) Examples of the (meth)acrylamide monomer include
(meth)acryloyl morpholine,
dimethyl (meth)acrylamide,
diethyl (meth)acrylamide,
(meth)acrylamide N-methylol (meth)acrylamide, and the like.

(12) Examples of the monofunctional unsaturated compound include biphenyl structure-containing (meth)acrylate compounds. Specific examples thereof include:
 biphenyl (meth)acrylates such as
 o-biphenyl (meth)acrylate,
 m-biphenyl (meth)acrylate, and
 p-biphenyl (meth)acrylate;
 biphenyloxyalkyl (meth)acrylates such as
 o-biphenyloxymethyl (meth)acrylate,
 m-biphenyloxymethyl (meth)acrylate,
 p-biphenyloxymethyl (meth)acrylate,
 o-biphenyloxyethyl (meth)acrylate,
 m-biphenyloxyethyl (meth)acrylate,
 p-biphenyloxyethyl (meth)acrylate,
 o-biphenyloxypropyl (meth)acrylate,
 m-biphenyloxypropyl (meth)acrylate, and
 p-biphenyloxypropyl (meth)acrylate; and
 biphenyloxypolyalkylene glycol (meth)acrylates such as
 (o-biphenyloxy)diethylene glycol (meth)acrylate,
 (m-biphenyloxy)diethylene glycol (meth)acrylate,
 (p-biphenyloxy)diethylene glycol (meth)acrylate,
 (o-biphenyloxy)dipropylene glycol (meth)acrylate,
 (m-biphenyloxy)dipropylene glycol (meth)acrylate,
 (p-biphenyloxy)dipropylene glycol (meth)acrylate,
 (o-biphenyloxy)polyethylene glycol (meth)acrylate,
 (m-biphenyloxy)polyethylene glycol (meth)acrylate,
 (p-biphenyloxy)polyethylene glycol (meth)acrylate,
 (o-biphenyloxy)polypropylene glycol (meth)acrylate,
 (m-biphenyloxy)polypropylene glycol (meth)acrylate, and
 (p-biphenyloxy)polypropylene glycol (meth)acrylate.

(13) Examples of the polyfunctional unsaturated compound include bifunctional monomers, tri- or more functional monomers, urethane (meth)acrylates, the above-described epoxy(meth)acrylates, polyester (meth)acrylates, polyether (meth)acrylates, and the like.

Specific examples of the bifunctional monomer include
 ethylene glycol di(meth)acrylate,
 diethylene glycol di(meth)acrylate,
 triethylene glycol di(meth)acrylate,
 tetraethylene glycol di(meth)acrylate,
 polyethylene glycol di(meth)acrylate,
 propylene glycol di(meth)acrylate,
 dipropylene glycol di(meth)acrylate,
 polypropylene glycol di(meth)acrylate,
 butylene glycol di(meth)acrylate,
 neopentyl glycol di(meth)acrylate,
 ethylene oxide-modified bisphenol A di(meth)acrylate,
 propylene oxide-modified bisphenol A di(meth)acrylate,
 1,6-hexanediol di(meth)acrylate,
 1,6-hexanediol ethylene oxide-modified di(meth)acrylate,
 glycerin di(meth)acrylate,
 pentaerythritol di(meth)acrylate,
 ethylene glycol diglycidyl ether di(meth)acrylate,
 diethylene glycol diglycidyl ether di(meth)acrylate,
 phthalic acid diglycidyl ester di(meth)acrylate,
 hydroxypivalic acid-modified neopentyl glycol di(meth)acrylate,
 isocyanuric acid ethylene oxide-modified diacrylate,
 2-(meth)acryloyloxyethyl acid phosphate diester, and the like.

Specific examples of the tri- or more functional monomer include
 trimethylolpropane tri(meth)acrylate,
 pentaerythritol tri(meth)acrylate,
 pentaerythritol tetra(meth)acrylate,
 dipentaerythritol tri(meth)acrylate,
 dipentaerythritol tetra(meth)acrylate,
 dipentaerythritol penta(meth)acrylate,
 dipentaerythritol hexa(meth)acrylate,
 tri(meth)acryloyloxyethoxytrimethylolpropane,
 glycerin polyglycidyl ether poly(meth)acrylate,
 tris(2-(meth)acryloyloxyethyl)isocyanurate,
 isocyanuric acid ethylene oxide-modified tri(meth)acrylate,
 ethylene oxide-modified dipentaerythritol penta(meth)acrylate,
 ethylene oxide-modified dipentaerythritol hexa(meth)acrylate,
 ethylene oxide-modified pentaerythritol tri(meth)acrylate,
 ethylene oxide-modified pentaerythritol tetra(meth)acrylate,
 succinic acid-modified pentaerythritol tri(meth)acrylate, and the like.

Other than the above-described polymerizable monomers, examples further include:
 divinylbenzene, piperylene, isoprene, pentadiene, vinylcyclohexene, chloroprene, butadiene, methylbutadiene, cyclopentadiene, methylpentadiene, acrylonitrile, methacrylonitrile, vinyl acetate, vinyl propionate, vinyl stearate, vinyl chloride, vinylidene chloride, alkyl vinyl ether, vinyltoluene, vinylpyridine, vinylpyrrolidone, itaconic acid dialkyl ester, fumaric acid dialkyl ester, allyl alcohol, acryloyl chloride, methyl vinyl ketone, N-acrylamide methyl trimethylammonium chloride, allyl trimethylammonium chloride, dimethylallyl vinylketone, 2-chloroethyl vinyl ether, triallyl isocyanurate, tetraallyl glycoluril,
 N-vinylpyrrolidone, N-vinyl caprolactam, ethylene glycol diallyl carbonate, trimellitic acid triallyl ester,
 trifluoroethyl (meth)acrylate,
 tribromobenzyl (meth)acrylate,
 perfluorooctylethyl (meth)acrylate,
 sulfur-containing (meth)acrylate,
 (meth)acryloyloxypropyl tris(methoxy)silane, and the like.

In the second resin composition of the present invention, the above-described polymerizable monomer and polymerizable oligomer may be used in combination as an enic compound, the polymerizable monomers exemplified above may be used in combination as the polymerizable monomer (different types of polymerizable monomers may be used in combination), and different types of polymerizable oligomers may be used in combination as the polymerizable oligomer.

The ratio (proportion) of the contents between the thiol compound of the present invention and the enic compound in the second resin composition of the present invention is set such that the content of the enic compound is preferably an appropriate ratio in a range of 0.01 to 1,000 times (weight ratio) and more preferably an appropriate ratio in a range of 0.1 to 100 times (weight ratio), to the content of the thiol compound of the present invention.

In the second resin composition of the present invention, another thiol compound described above may be used together with the thiol compound of the present invention.

The ratio (proportion) of the contents between the thiol compound of the present invention and another thiol compound in the second resin composition of the present invention is set such that the content of another thiol compound is preferably an appropriate ratio in a range of 0 to 100 times (weight ratio) and more preferably an appropriate ratio in a range of 0.1 to 10 times (weight ratio), to the content of the thiol compound of the present invention.

Examples of a method for polymerizing (curing) the second resin composition of the present invention include methods of photo-curing and heat-curing.

Examples of the method of photo-curing include a method of irradiating active energy ray, preferably a method of concurrently using a photopolymerization initiator. Examples of the active energy ray include light, radiation, electromagnetic wave, electron beams, and the like. The electron beam or light in the ultraviolet to infrared wavelength range is preferred. As a light source, use can be made of, for example, an ultrahigh pressure mercury light source or a metal halide light source in the case of irradiation of ultraviolet rays, a metal halide light source or a halogen light source in the case of irradiation of visible light, and a halogen light source in the case of irradiation of infrared rays. Furthermore, light sources such as laser or LED corresponding to light emission of various wavelengths, the use of which is recently spreading, may be used.

The irradiation dose of the active energy rays can be appropriately set according to the type of the light source, and the like.

The photopolymerization initiator can be selected from a photo-radical polymerization initiator and a photo-anionic polymerization initiator, and the initiator may be added in the second resin composition. In the photo-curing, the means of heat polymerization (heat-curing) may be concurrently used in order to enhance production efficiency and properties of a cured product.

Any photo-radical polymerization initiator generally used can be used without particular limitation. Examples thereof include:

acetophenones such as 2-hydroxy-2-methyl-1-phenylpropan-1-one, 1-hydroxycyclohexylphenyl ketone, and 2-methyl-1-[4-(methylthio)phenyl]-2-morpholinopropan-1-one;

benzoins such as benzyldimethyl ketal;

benzophenones such as benzophenone, 4-phenylbenzophenone, and hydroxybenzophenone;

thioxanthones such as isopropylthioxanthone and 2,4-diethylthioxanthone;

methylphenyl glyoxylate; and the like.

Those may be used in combination.

As necessary, the photo-radical polymerization initiator can be used together with a conventional photopolymerization accelerator such as a benzoic acid such as 4-dimethylaminobenzoic acid, and a tertiary amine.

Any photo-anionic polymerization initiator generally used can be used without particular limitation. Examples thereof include an onium salt and a carbamate.

Examples of the onium salt include 1,2-diisopropyl-3-(bis(dimethylamino)methylene)guanidium 2-(3-benzoylphenyl) propionate, 1,2-dicyclohexyl-4,4,5,5-tetramethyl biguanidium n-butyltriphenyl borate, and the like.

Examples of the carbamate include 2-nitrophenylmethylpiperidine-1-carboxylate, 1-(anthraquinon-2-yl)ethylimidazole carboxylate, 1-(3-(2-hydroxyphenyl)-2-propenoyl) piperidine, 9-anthranylmethyldiethyl carbamate, and the like.

When the second resin composition of the present invention is photo cured, a sensitizer such as pyrene, perylene, acridine orange, thioxanthone, 2-chlorothioxanthone, and benzoflavine can be used for example.

The content of the photopolymerization initiator in the second resin composition of the present invention is preferably a proportion of 0.001 to 20 wt % and more preferably a proportion of 0.01 to 10 wt %, based on the entire second resin composition (total amount).

On the other hand, examples of a method for heat-curing the second resin composition of the present invention include a method of concurrently using a thermal polymerization initiator. The thermal polymerization initiator can be selected from a heat-radical polymerization initiator and a heat-anionic polymerization initiator, and those may be added in the resin composition.

Regarding the conditions in the heat-curing, the heating temperature and the heating time can be appropriately set, preferably set in a range of 60 to 130° C. for 30 to 240 min, and more preferably set in a range of 70 to 125° C. for 30 to 120 min.

Any heat-radical polymerization initiator generally used can be used without particular limitation. Examples thereof include: peroxides such as diisopropyl peroxydicarbonate, benzoyl peroxide, t-butyl peroxyisobutyrate, t-hexyl peroxyisopropyl monocarbonate, t-hexyl peroxy 2-ethylhexanoate, 1,1,3,3-tetramethylbutyl peroxy 2-ethylhexanoate, t-butyl peroxypivalate, t-hexyl peroxypivalate, t-butyl peroxyneodecanoate, t-hexyl peroxyneodecanoate, 1,1,3,3-tetramethylbutyl peroxyneodecanoate, 1,1-bis(t-hexylperoxy)cyclohexane, 3,5,5-trimethylhexanoyl peroxide, and lauroyl peroxide; and azo compounds such as azobisisobutyronitrile, 2,2'-azobis(2-methylbutyronitrile) and dimethyl 2,2'-azobis(2-methylpropionate). Those may be used in combination.

Any heat-anionic polymerization initiator generally used can be used without particular limitation. Examples thereof include an amine an imidazole, and the like. Those may be used in combination.

Examples of the amine include diethylenetriamine, triethylenetetramine, isophorone diamine, xylylene diamine, diaminodiphenylmethane, 1,3,4,6-tetrakis(3-aminopropyl) glycoluril, and the like.

Examples of the imidazole include 2-methylimidazole, 2-ethyl-4-methylimidazole, 2-phenylimdazole, and the like.

The content of the thermal polymerization initiator in the second resin composition of the present invention is preferably a proportion of 0.001 to 20 wt % and more preferably a proportion of 0.01 to 10 wt %, based on the entire second resin composition (total amount).

In the second resin composition of the present invention, in the case where an epoxy resin (epoxy compound) is contained as an additive (modifier), a photo-cationic polymerization initiator or a heat-cationic polymerization initiator may be used.

Any photo-cationic polymerization initiator generally used can be used without particular limitation. Examples thereof include an onium salt, an organometallic complex and the like.

Examples of the onium salt include diazonium salts, sulfonium salts, and iodonium salts.

Examples of the organometallic complex include iron-arene complexes, titanocene complexes, aryl silanol-aluminum complexes, and the like.

Examples of a commercially available photo-cationic polymerization initiator include "ADEKA OPTOMER SP-150 (trade name)" and "ADEKA OPTOMER SP-170 (trade name)", manufactured by ADEKA Corporation, "UVE-1014 (trade name)" manufactured by General Electronics, "CD-1012 (trade name)" manufactured by Sartomer Company, "CPI-100P (trade name)" manufactured by San-Apro Ltd., and the like.

Examples of a counter anion of the photo-cationic polymerization initiator include $SbF_6^-$, $AsF_6^-$, $B(C_6F_5)_4^-$, $PF_6^-$, and the like.

Any heat-cationic polymerization initiator generally used can be used without particular limitation. Examples thereof include various onium salts such as a quaternary ammonium salt, a phosphonium salt and a sulfonium salt, an organometallic complex, and the like. Those may be used in combination.

Examples of a commercially available onium salt include "ADEKA OPTON CP-66 (trade name)" and "ADEKA OPTON CP-77 (trade name)", manufactured by ADEKA Corporation, "SAN-AID SI-60L (trade name)", "SAN-AID SI-80L (trade name)" and "SAN-AID SI-100L (trade name)", manufactured by Sanshin Chemical Industry Co., Ltd., "CI Series (trade name)" manufactured by Nippon Soda Co., Ltd., and the like.

Examples of the organometallic complex include alkoxysilane-aluminum complexes and the like.

As necessary, the second resin composition of the present invention may further contain the above-described additive (modifier) (see paragraph [0110]) in a proportion of 0.01 to 50 wt % based on the entire second resin composition (total amount) so long as the effect of the present invention is not impaired.

A method for preparing (mixing) the second resin composition of the present invention is not particularly limited. The second resin composition can be prepared by, for example, mixing the thiol compound of the present invention, an enic compound, another thiol compound, a photopolymerization initiator and/or a thermal polymerization initiator, and an additive. As the mixing means, a conventional method (e.g., the method described in paragraph [0113]) can be used. The thiol compound of the present invention (as necessary, together with another thiol compound) may be previously dissolved or dispersed in a diluent for viscosity adjustment (organic solvent).

The first resin composition and the second resin composition of the present invention containing the thiol compound of the present invention (those resin compositions are sometimes collectively called "the resin composition of the present invention") are expected to give a cured product having excellent hydrolysis resistance (moisture resistance).

That is, the resin composition of the present invention gives a cured product having excellent moisture resistance as compared with a resin composition containing a conventional thiol compound, and therefore can be suitably used as an adhesive and a sealant. Specifically, the adhesive and the sealant of the present invention contain the resin composition of the present invention as a component.

The adhesive and the sealant of the present invention may contain an additive. Examples of the additive include flow behavior modifiers such as silicic acid, magnesium silicate and barium sulfate, thermal conductivity-imparting agents such as alumina, conductivity-imparting agents such as silver and carbon, coloring agents such as a pigment and a dye, and the like. These additives can be mixed with the resin composition of the present invention during preparation thereof. Furthermore, these additives may be mixed with the already prepared resin composition of the present invention. As the mixing means, a conventional method (e.g., the method described in paragraph [0113]) can be used.

The adhesive and the sealant of the present invention can be applied to various fields without particular limitation in the uses. Examples of the use of the adhesive include: adhesives for a flexible printed wiring board; interlayer adhesives of a multilayered substrate such as a build-up substrate; adhesives for bonding optical parts; adhesives for laminating optical discs; adhesives for mounting a printed wiring board; die-bonding adhesives; adhesives for a semiconductor, such as an underfill; adhesives for mounting, such as an underfill for BGA reinforcement, an anisotropic conductive film (ACF), and an anisotropic conductive paste (ACP); adhesives for light pick-up; adhesives for bonding light paths; adhesives used between an exterior material, a base material or a ceiling material and an interior material; adhesives for adhering a tile or stone to an exterior wall material or a base material; adhesives for adhering a wooden flooring material, a polymer material floor sheet or a floor tile to various floors; adhesives for a structural material, body or part of automobiles, aircrafts or the like; adhesives for automobile interior; adhesives for joint of steel plates, and the like.

Examples of the use of the sealant include: sealants for a joint of an exterior material such as various metal panels and siding boards; sealants used between an exterior material, a base material or a ceiling material and an interior material; sealants for a joint of various concrete products such as a road, a bridge, a tunnel or a breakwater; sealants of a structural material, body or part of automobiles, aircrafts or the like; sealants for joint of steel plates; medical equipment sealants, and the like.

The resin composition of the present invention can be applied to products (parts and members) of various fields in which the material may be a resin, other than the above-described adhesive and sealant, and can be used in electric/electronic, optical, building, civil engineering, automobile/aircraft, and medical fields and further as a raw material of daily miscellaneous goods or the like.

For example, examples of part/member and a material in electric/electronic fields include resin-attached copper foils, prepregs, copper-clad laminate plates, printed wiring boards, solder resist inks, conductive pastes, interlayer insulating materials, encapsulants, encapsulants for LED, insulating materials, thermal conductive materials, hot melt materials, paints, potting agents, and the like. More specific examples thereof include:

encapsulant materials and layer forming materials of a printed wiring board and an electronic part, such as an interlayer insulting film and a wiring coating film;

forming materials of a display device, such as a color filter, a film for flexible display, a resist material, and an oriented film;

forming materials of a semiconductor device, such as a resist material and a buffer coat film; and forming materials of an optical part, such as a hologram, an optical waveguide, an optical circuit, an optical circuit part, and an antireflection film.

The examples further include: forming materials of a rigid wiring board and a flexible printed wiring board, for mounting on a semiconductor; materials for mounting a semiconductor; encapsulants for a semiconductor; encapsulants for a solar cell; insulating films for a semiconductor; coverlay films for protecting a flexible printed circuit; coating agents for covering a wiring; and the like.

Examples of the material in the optical field include core materials for optical fiber, clad materials, lens, and wear-resistant coating agents of a lens (e.g., a hard coat forming liquid).

Examples of the material in the building field include: coating materials and primers of an exterior material such as various metal panels and siding boards; grouting materials, damping materials, soundproof materials, conductive materials for shielding electromagnetic waves, and putties, used between an exterior material, a base material or a ceiling material and an interior material; pressure-sensitive adhesives for adhering a wooden flooring material, a polymer material floor sheet or a floor tile to various floors; grouting materials for repairing cracks of various exterior materials and interior materials; and the like.

Examples of the material in the civil engineering field include: coating materials of various concrete products such as a road, a bridge, a tunnel or a breakwater; primers; paints; putties; grouting materials; spraying materials; molding materials; and the like.

Examples of the material in automobile and aircraft fields include: coating materials, cushioning materials, damping materials, soundproof materials and spraying materials of a structural material, body or part: pressure-sensitive adhesives, coating materials and foaming materials for interior decoration of automobiles; coating materials for a joint of steel plates; and the like.

Examples of the material in the medical field include artificial bones, dental impression materials, medical rubber materials, medical pressure-sensitive adhesives, and the like.

EXAMPLES

The present invention is described in more detail below by Examples (synthesis tests and evaluation tests) and Comparative Examples (evaluation tests), but it should be understood that the present invention is not construed as being limited to those.

The main raw materials used in the synthesis tests are as follows.

[Main Raw Materials]
1-allyl-2-allyloxybenzene (synthesized according to the method described in J. Am. Chem. Soc., Vol. 81, pp. 2705-2715 (1959), see chemical formula (b-4))
1,3-diallyl-2-imidazolidinone (synthesized according to the method described in International Publication No. 2002/036662, see chemical formula (b-79))
1,3-diallyl-2-benzimidazolone (synthesized according to the method described in J. Am. Chem. Soc., Vol. 80, pp. 1657-1662 (1958), see chemical formula (b-81))
Bisphenol A diallyl ether (synthesized according to the method described in JP-A-H05-155798, see chemical formula (b-45))
1,3-bis(allyloxy)benzene (synthesized according to the method described in Synthetic Communication, Vol. 30, pp. 3955-3961 (2000), see chemical formula (b-8))
1,4-bis[(allyloxy)methyl]benzene (synthesized according to the method described in International Publication No. 2011/078060, see chemical formula (b-17))
Bisphenol S diallyl ether (synthesized according to the method described in International Publication No. 2013/114987, see chemical formula (b-49))
N,N-diallyl pyromellitimide (synthesized according to the method described in JP-A-2007-332091, see chemical formula (b-82))
N-allyl-tetrahydrophthalimide (synthesized according to the method described in Organic Letter, Vol. 19, pp. 6570-6573 (2017), see chemical formula (b-84))
4-(4-vinylbenzyloxy)allylbenzene (synthesized according to the method described in J. Am. Chem. Soc., Vol. 81, pp. 2705-2715 (1959), see chemical formula (b-33))
3-thiapentane-1,5-dithiol (manufactured by MARUZEN CHEMICAL TRADING CO., LTD., see chemical formula (C-1))
Azobisisobutyronitrile (manufactured by Wako Pure Chemical Industries, Ltd.)
Benzoyl peroxide (manufactured by Wako Pure Chemical Industries, Ltd.)

The main raw materials (excluding the thiol compound of the present invention) of the epoxy resin composition used in the evaluation tests are as follows.

[Main Raw Materials]
(A) Curing Agent
1,3,4,6-tetrakis(2-mercaptoethyl)glycoluril (manufactured by Shikoku Chemicals Corporation, trade name "TS-G", see chemical formula (VI), thiol equivalent: 100.4)
Pentaerythritol tetrakis(3-mercaptopropionate) (manufactured by SC Organic Chemical Co., Ltd., trade name "PEMP", see chemical formula (VII), thiol equivalent: 122.2)

[Chem. 48]

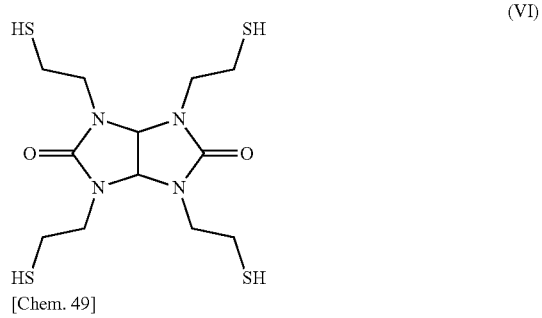

(VI)

[Chem. 49]

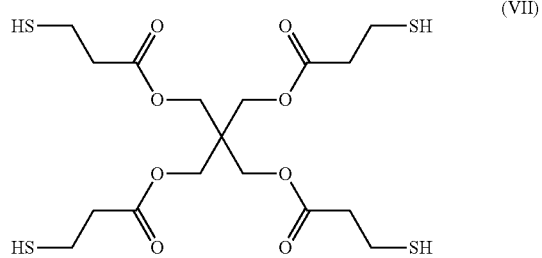

(VII)

(B) Curing Accelerator
Dimethylbenzylamine (manufactured by Wako Pure Chemical Industries Ltd.)
(C) Epoxy compound (epoxy resin)
Bisphenol A epoxy resin (manufactured by Mitsubishi Chemical Corporation, trade name "jER828", epoxy equivalent: 187.0)

The measurement method of storage modulus and the measurement method of adhesive strength, in the evaluation tests used in Examples and Comparative Examples are as follows.

[Measurement of Storage Modulus]

An epoxy resin composition was cured (80° C./1 hour). The storage modulus E (GPa) at 25° C. of the obtained cured product (test piece: length 20 mm×width 5 mm×thickness 1 mm) was measured (frequency: 1 Hz) by using a dynamic viscoelasticity measuring device ("Rheosol-G5000" manufactured by UBM).

It is determined that the impact resistance of the cured product is excellent as the storage modulus is small (low elasticity).

[Measurement of Adhesive Strength (Moisture Resistance Test)]

Two blast-treated aluminum plates (length 100 mm×width 25 mm×thickness 1.6 mm) were used. An epoxy resin composition (adhesive) was applied onto one surface of each aluminum plate on a region (length 12.5 mm×width 25 mm) in a range of 12.5 mm from either one edge (longitudinal direction).

Subsequently, the two aluminum plates were stuck such that those coated surfaces faced to each other, and then heated (the epoxy resin composition was cured under conditions of 80° C. for 1 hour) to prepare a test piece.

Tensile shear adhesive strength (MPa) of the test piece was measured in accordance with JIS K6850 before and after performing a high-temperature and high-pressure steam treatment (PCT treatment, 121° C./48 hours) by an autoclave.

The residual ratio of the tensile shear adhesive strength after the PCT treatment (hereinafter sometimes referred to as "strength residual ratio") was calculated from the measured values according to the following equation.

Strength residual ratio (%)=(tensile shear adhesive strength after PCT treatment)/(tensile shear adhesive strength before PCT treatment)×100

It is determined that the moisture resistance of a cured product is excellent as the strength residual ratio is larger, and it is recognized that the epoxy resin composition is suitable as an adhesive.

The case where an adhesive layer was eluted by the PCT treatment and the measurement of tensile shear adhesive strength was impossible was indicated as "N.D.".

Example 1

Synthesis of Adduct of 1-allyl-2-allyloxybenzene and 3-thiapentane-1,5-dithiol

In a four-necked eggplant flask having a volume of 500 ml were charged 26.14 g (150.0 mmol) of 1-allyl-2-allyloxybenzene, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 49.18 g of a yellow liquid (yield: 67.9%).

$^1$H-NMR spectral data of the yellow liquid was as follows.

$^1$H-NMR (d$_6$-DMSO) δ: 7.15 (t, 1H), 7.12 (d, 1H), 6.94 (d, 1H), 6.85 (t, 1H), 4.05 (t, 2H), 2.69 (m, 20H), 2.51 (t, 2H), 1.99 (quin, 2H), 1.77 (quin, 4H).

IR spectral data of the yellow liquid was as shown in the chart of FIG. 1.

It was identified from these spectral data that the yellow liquid obtained was the target thiol compound represented by the chemical formula (I-17) (thiol equivalent: 260.7).

[Chem. 50]

(I-17)

Example 2

Synthesis of Adduct of 1,3-diallyl-2-imidazolidinone and 3-thiapentane-1,5-dithiol In a four-necked eggplant flask having a volume of 500 ml were charged 24.93 g (150.0 mmol) of 1,3-diallyl-2-imidazolidinone, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 43.81 g of a light yellow liquid (yield: 61.5%).

$^1$H-NMR spectral data of the light yellow liquid was as follows.

$^1$H-NMR (d$_6$-DMSO) δ: 3.24 (s, 4H), 3.14 (t, 4H), 2.69 (m, 16H), 2.51 (t, 6H), 1.68 (quin, 4H).

Figure 2:
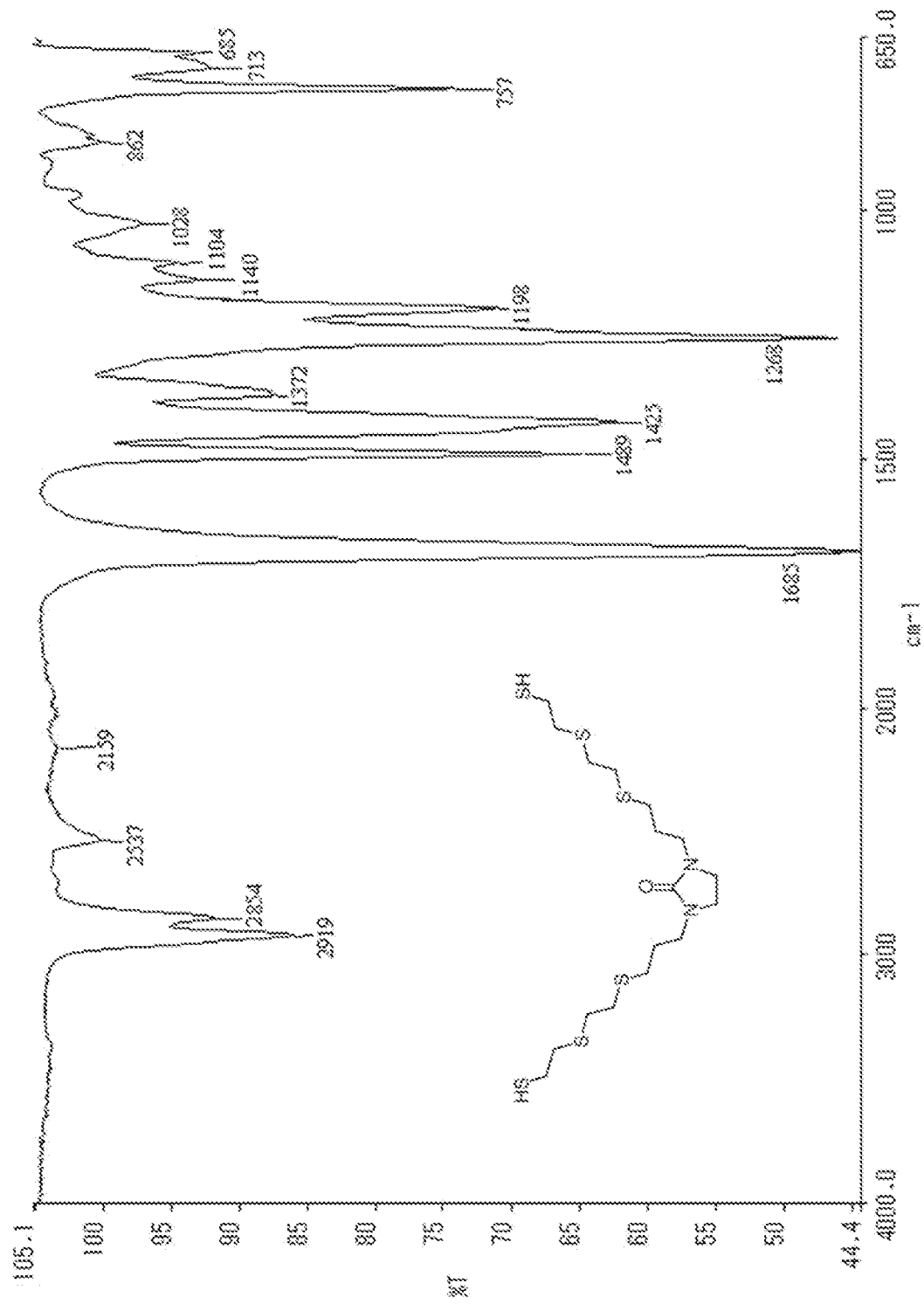
FIG. 2 is an IR spectral chart of a light yellow liquid obtained in Example 2.

IR spectral data of the light yellow liquid was as shown in the chart of FIG. 2.

It was identified from these spectral data that the light yellow liquid obtained was the target thiol compound represented by the chemical formula (I-83) (thiol equivalent: 248.4).

[Chem. 51]

(I-83)

Example 3

Synthesis of Adduct of 1,3-diallyl-2-benzimidazolone and 3-thiapentane-1,5-dithiol In a four-necked eggplant flask having a volume of 500 ml were charged 32.14 g (150.0 mmol) of 1,3-diallyl-2-benzimidazolone, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 53.49 g of a brown liquid (yield: 68.2%).

$^1$H-NMR spectral data of the brown liquid was as follows.

$^1$H-NMR (d$_6$-DMSO) δ: 7.19 (d, 2H), 7.06 (t, 2H), 3.91 (t, 4H), 2.69 (m, 20H), 2.54 (t, 2H), 1.91 (quin, 4H).

Figure 3:
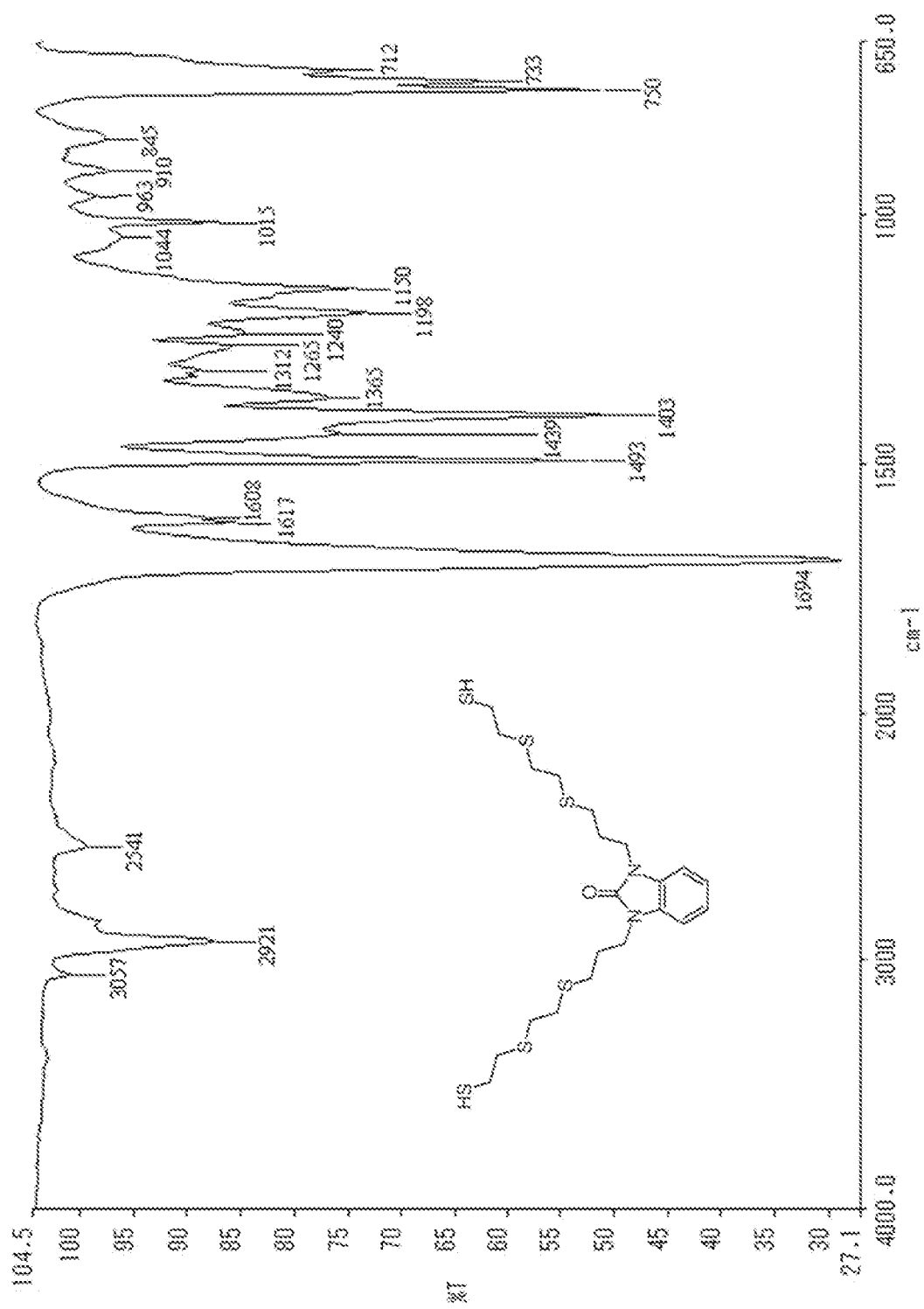
FIG. 3 is an IR spectral chart of a brown liquid obtained in Example 3.

IR spectral data of the brown liquid was as shown in the chart of FIG. 3.

It was identified from these spectral data that the brown liquid obtained was the target thiol compound represented by the chemical formula (I-85) (thiol equivalent: 286.6).

[Chem. 52]

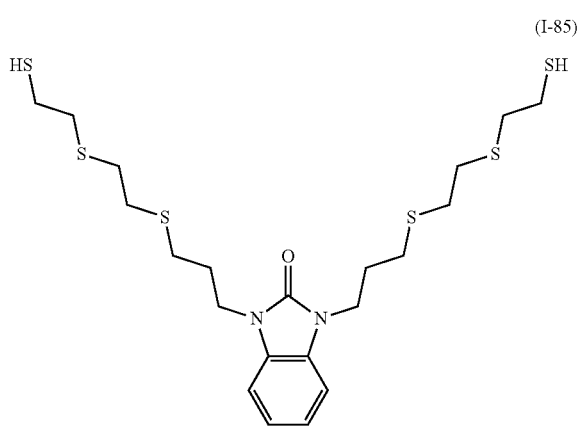

(I-85)

Example 4

Synthesis of Adduct of bisphenol A diallyl ether and 3-thiapentane-1,5-dithiol In a four-necked eggplant flask having a volume of 500 ml were charged 46.26 g (150.0 mmol) of bisphenol A diallyl ether, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 60.44 g of a yellow liquid (yield: 65.3%).

$^1$H-NMR spectral data of the yellow liquid was as follows.

$^1$H-NMR (d$_6$-DMSO) δ: 7.09 (d, 4H), 6.81 (d, 4H), 4.00 (t, 4H), 2.69 (m, 20H), 2.51 (t, 2H), 1.94 (quin, 4H), 1.57 (s, 6H).

Figure 4:
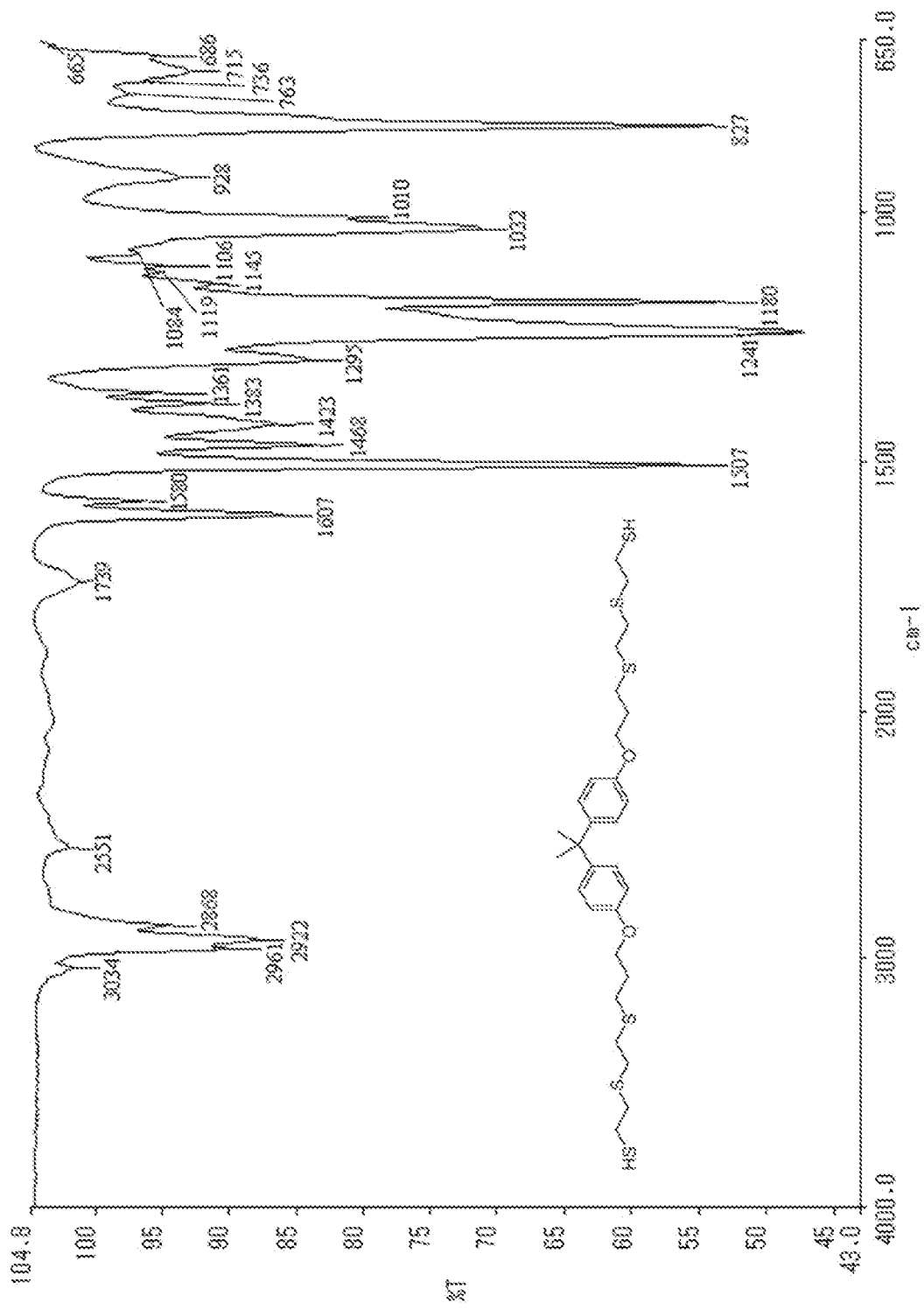
FIG. 4 is an IR spectral chart of a yellow liquid obtained in Example 4.

IR spectral data of the yellow liquid was as shown in the chart of FIG. 4.

It was identified from these spectral data that the yellow liquid obtained was the target thiol compound represented by the chemical formula (I-42) (thiol equivalent: 334.3).

[Chem. 53]

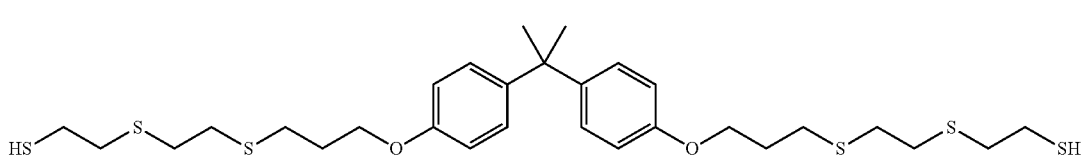

(I-42)

Example 5

Synthesis of Adduct of 1,3-bis(allyloxy)benzene and 3-thiapentane-1,5-dithiol In a four-necked eggplant flask having a volume of 500 ml were charged 28.54 g (150.0 mmol) of 1,3-bis(allyloxy)benzene, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 49.91 g of a white solid (yield: 66.7%).

$^1$H-NMR spectral data of the white solid was as follows.

$^1$H-NMR (d$_6$-DMSO) δ: 7.16 (t, 1H), 6.52 (d, 2H), 6.49 (s, 1H), 4.02 (t, 4H), 2.69 (m, 20H), 2.51 (t, 2H), 1.94 (quin, 4H).

Figure 5:
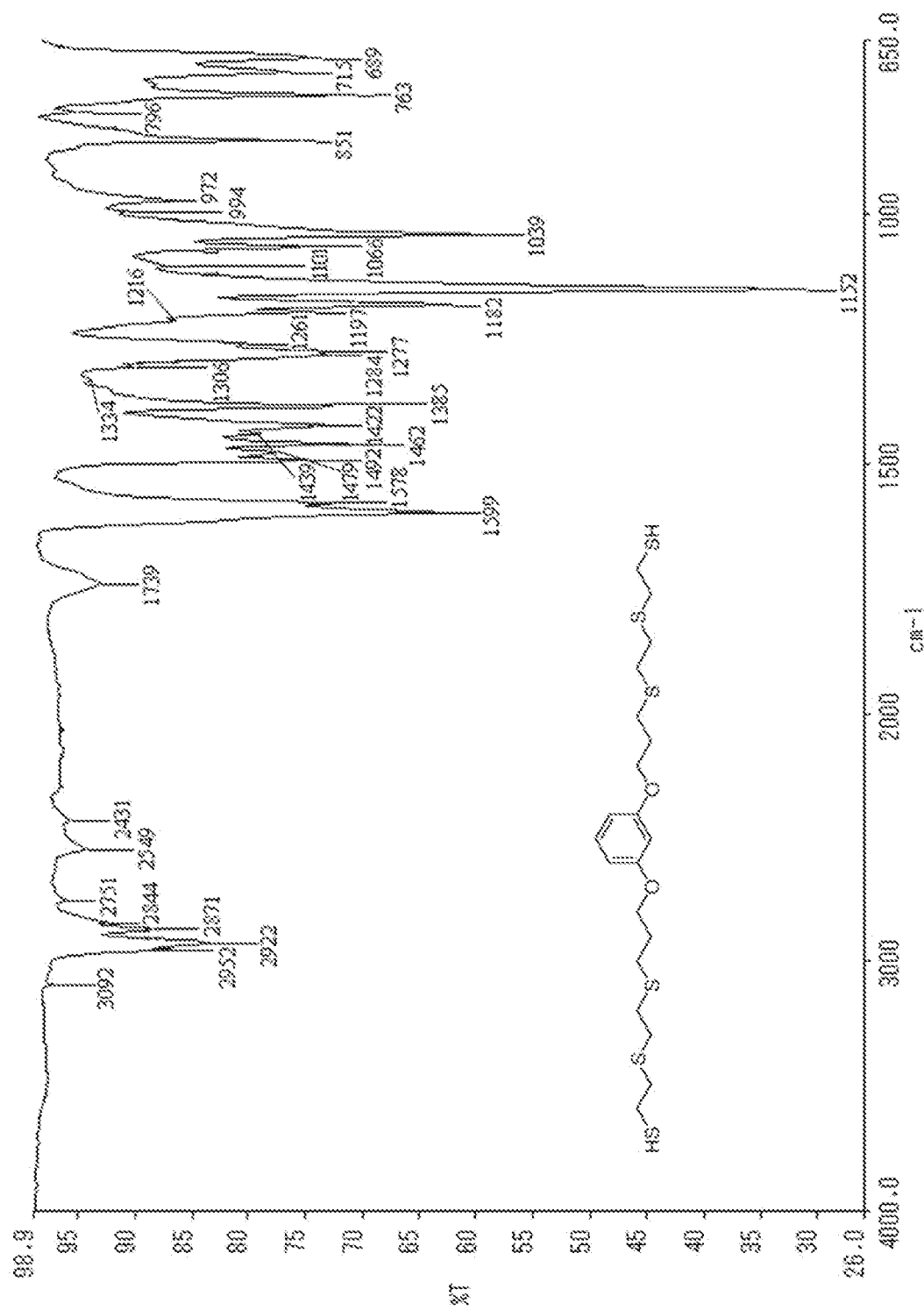
FIG. 5 is an IR spectral chart of a white solid obtained in Example 5.

IR spectral data of the white solid was as shown in the chart of FIG. 5.

It was identified from these spectral data that the white solid obtained was the target thiol compound represented by the chemical formula (I-5) (thiol equivalent: 229.8).

[Chem. 54]

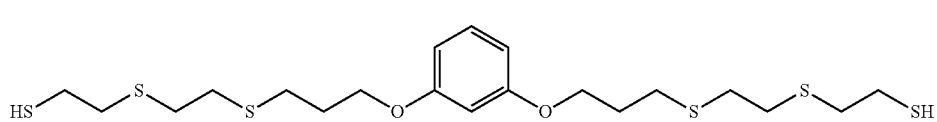

(I-5)

Example 6

Synthesis of Adduct of 1,4-bis[(allyloxy)methyl]benzene and 3-thiapentane-1,5-dithiol In a four-necked eggplant flask having a volume of 500 ml were charged 32.74 g (150.0 mmol) of 1,4-bis[(allyloxy)methyl]benzene, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=3/7 (v/v)), to thereby obtain 64.7 g of a colorless transparent liquid (yield: 81.9%).

$^1$H-NMR spectral data of the colorless transparent liquid was as follows.

$^1$H-NMR ($d_6$-DMSO) δ: 7.30 (s, 4H), 4.44 (s, 4H), 3.49 (t, 4H), 2.71 (m, 20H), 2.60 (t, 2H), 1.78 (quin, 4H).

Figure 6:
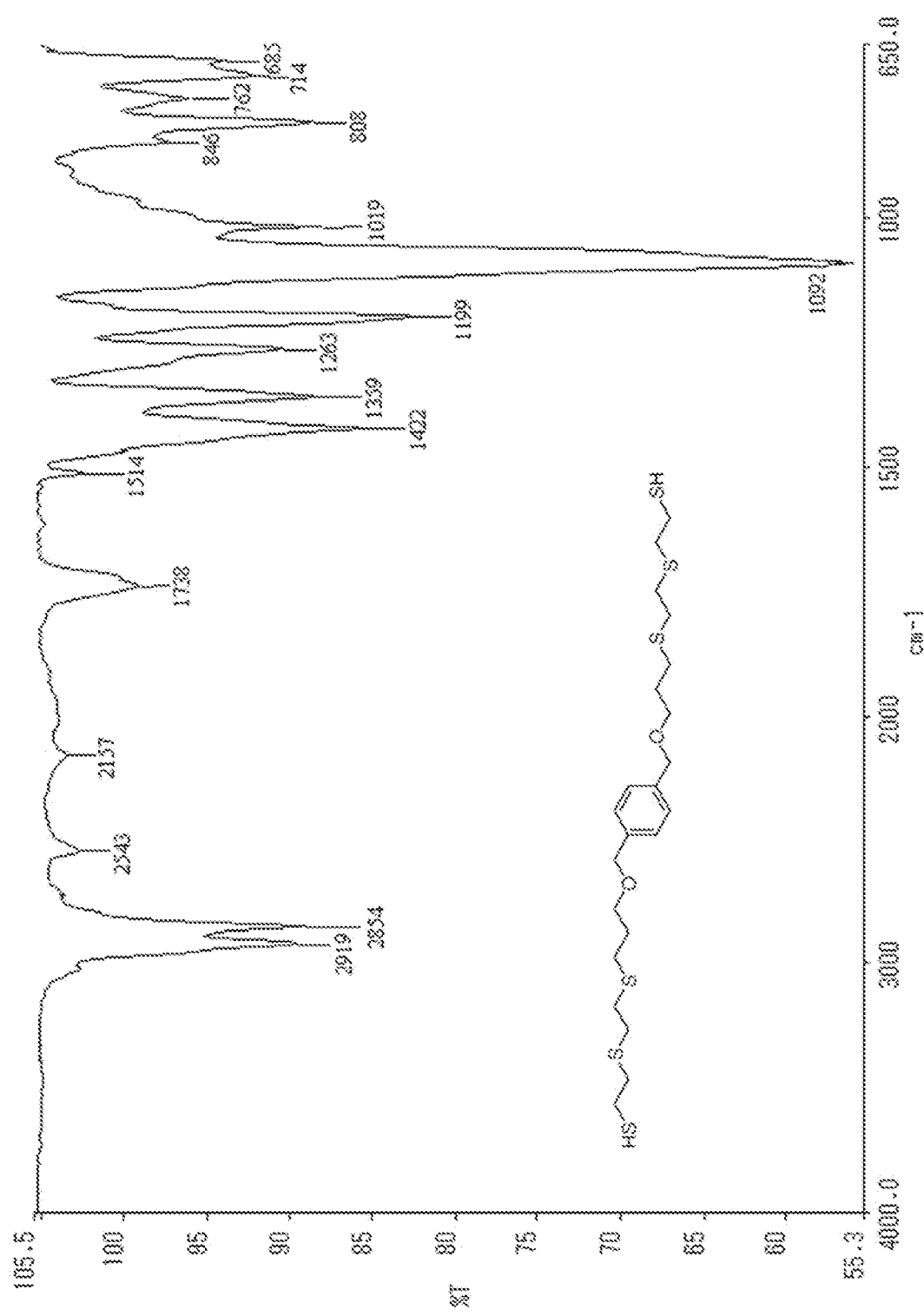
FIG. 6 is an IR spectral chart of a colorless transparent liquid obtained in Example 6.

IR spectral data of the colorless transparent liquid was as shown in the chart of FIG. 6.

It was identified from these spectral data that the colorless transparent liquid obtained was the target thiol compound represented by the chemical formula (I-14) (thiol equivalent: 272.4).

[Chem. 55]

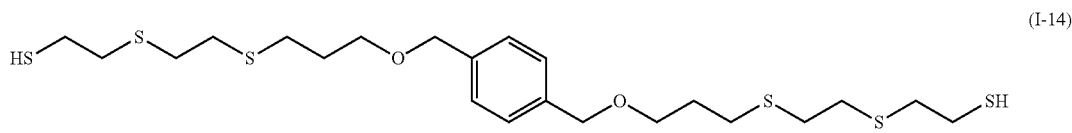

(I-14)

Example 7

Synthesis of Adduct of bisphenol S diallyl ether and 3-thiapentane-1,5-dithiol In a four-necked eggplant flask having a volume of 500 ml were charged 49.56 g (150.0 mmol) of bisphenol S diallyl ether, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=1/9 (v/v)), to thereby obtain 158.9 g of a white solid (yield: 68.9%).

$^1$H-NMR spectral data of the white solid was as follows.

$^1$H-NMR ($d_6$-DMSO) δ: 7.83 (d, 4H), 7.11 (d, 4H), 4.13 (t, 4H), 2.73-2.69 (m, 20H), 2.51 (t, 2H), 1.96 (quin, 4H).

Figure 7:
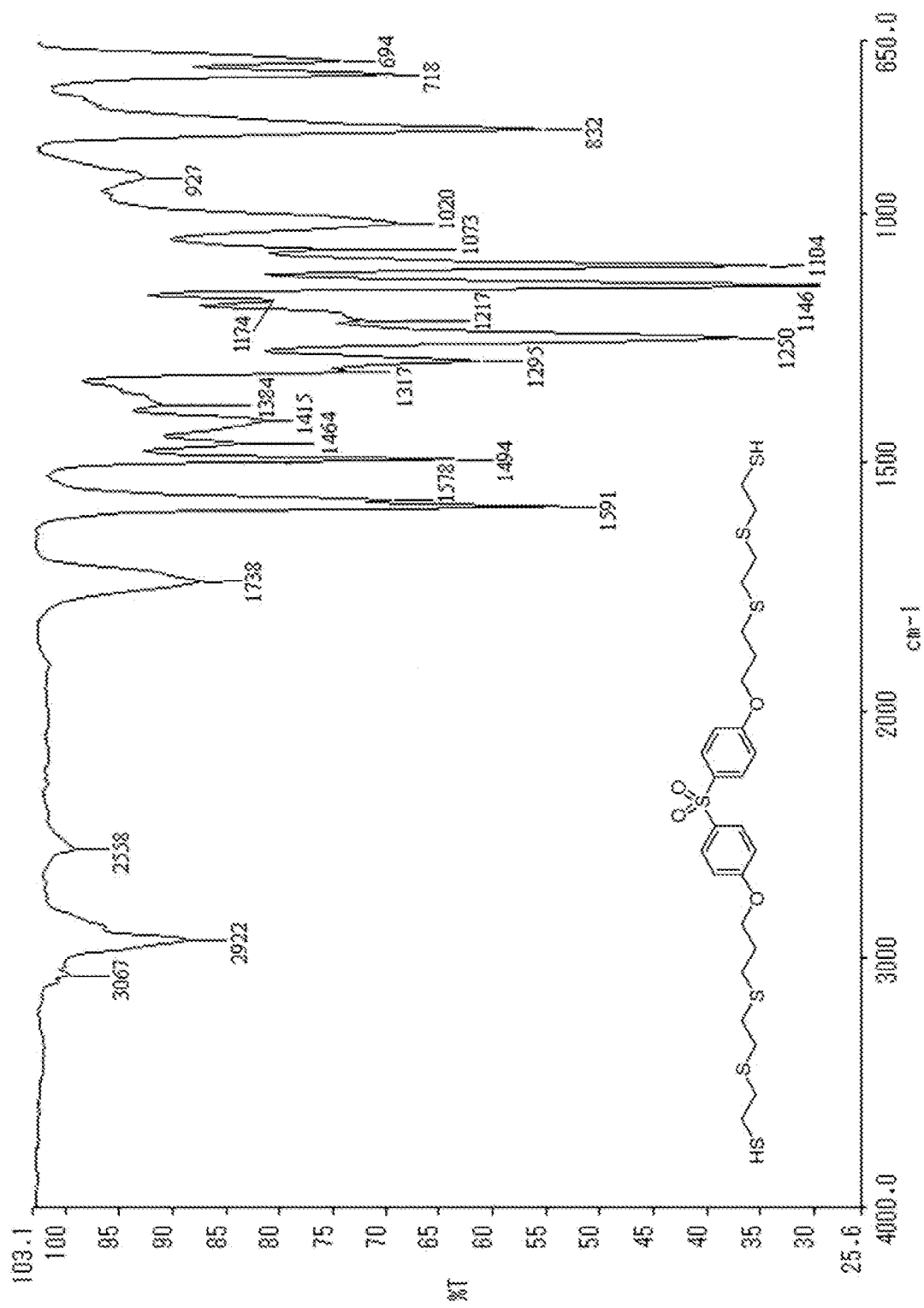
FIG. 7 is an IR spectral chart of a white solid obtained in Example 7.

IR spectral data of the white solid was as shown in the chart of FIG. 7.

It was identified from these spectral data that the white solid obtained was the target thiol compound represented by the chemical formula (I-46) (thiol equivalent: 317.9).

[Chem. 56]

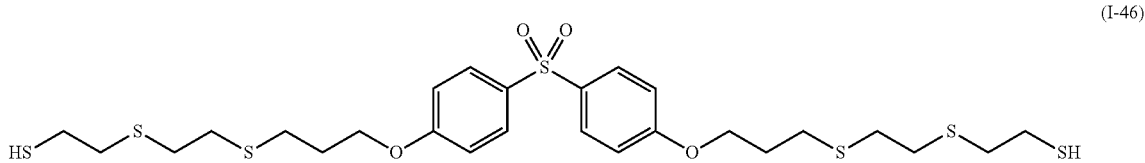

(I-46)

Example 8

Synthesis of Adduct of N,N-diallyl pyromellitimide and 3-thiapentane-1,5-dithiol In a four-necked eggplant flask having a volume of 500 ml were charged 44.44 g (150.0 mmol) of N,N-diallyl pyromellitimide, 115.74 g (750.0 mmol) of 3-thiapentane-1,5-dithiol, 0.25 g (1.5 mmol) of azobisisobutyronitrile, and 200.00 g of toluene, followed by stirring at 100° C. for 48 hours.

The reaction mixture obtained was concentrated and purified by a silica gel column chromatography (hexane/chloroform=1/9 (v/v)), to thereby obtain 54.99 g of a light yellow solid (yield: 60.6%).

$^1$H-NMR spectral data of the light yellow solid was as follows.

$^1$H-NMR (d$_6$-DMSO) δ: 8.18 (s, 2H), 3.72 (t, 4H), 2.66 (m, 20H), 2.52 (t, 2H), 1.88 (t, 4H).

Figure 8:
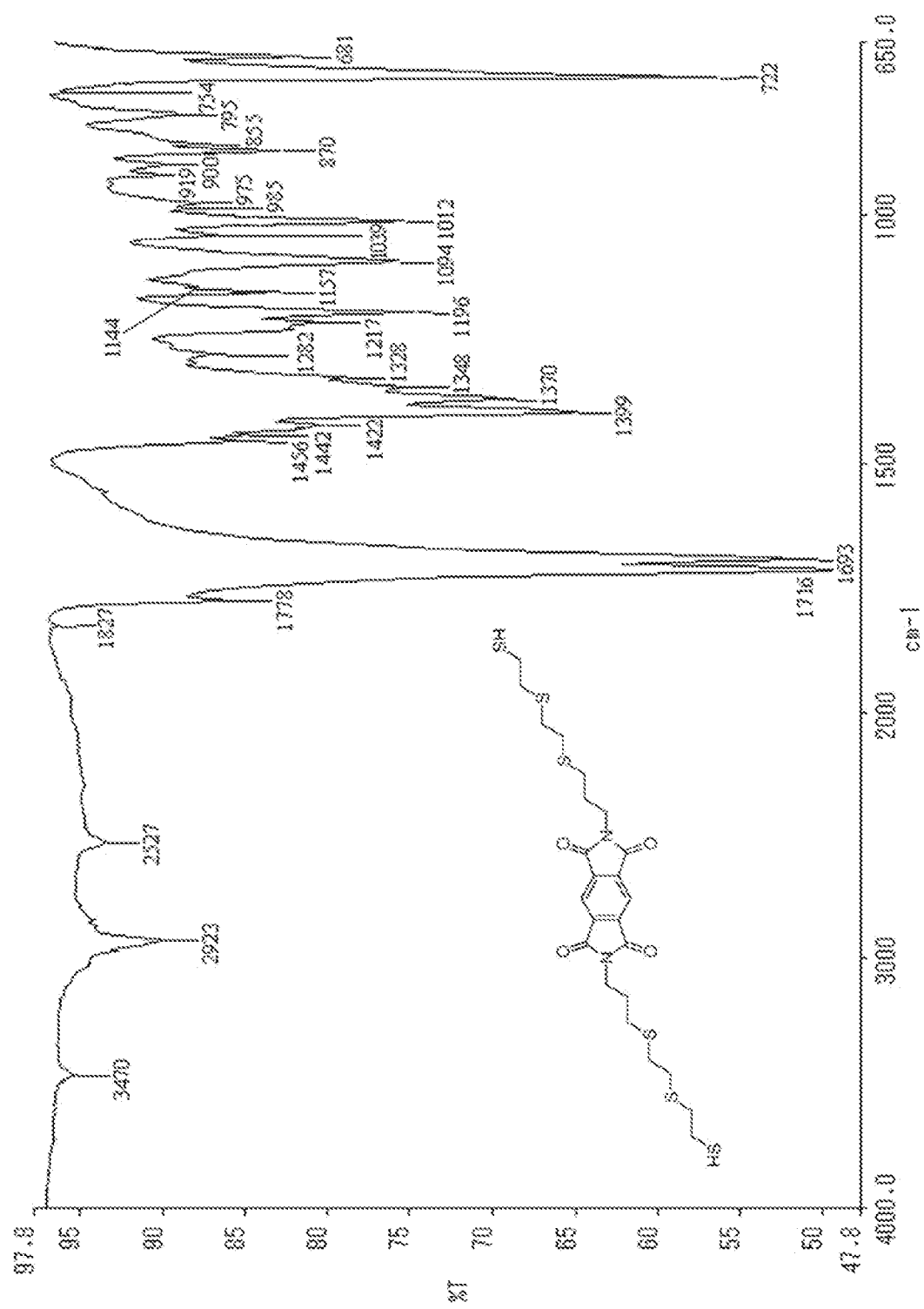
FIG. 8 is an IR spectral chart of a light yellow solid obtained in Example 8.

IR spectral data of the light yellow solid was as shown in the chart of FIG. 8.

It was identified from these spectral data that the light yellow solid obtained was the target thiol compound represented by the chemical formula (I-86) (thiol equivalent: 360.4).

$^1$H-NMR (d$_6$-DMSO) δ: 3.44 (t, 2H), 2.97-2.86 (m, 2H), 2.73-2.62 (m, 16H), 2.53-2.49 (m, 5H), 2.17 (dt, 2H), 1.96 (quin, 2H), 1.73 (t, 2H), 1.44 (quin, 2H).

Figure 9:
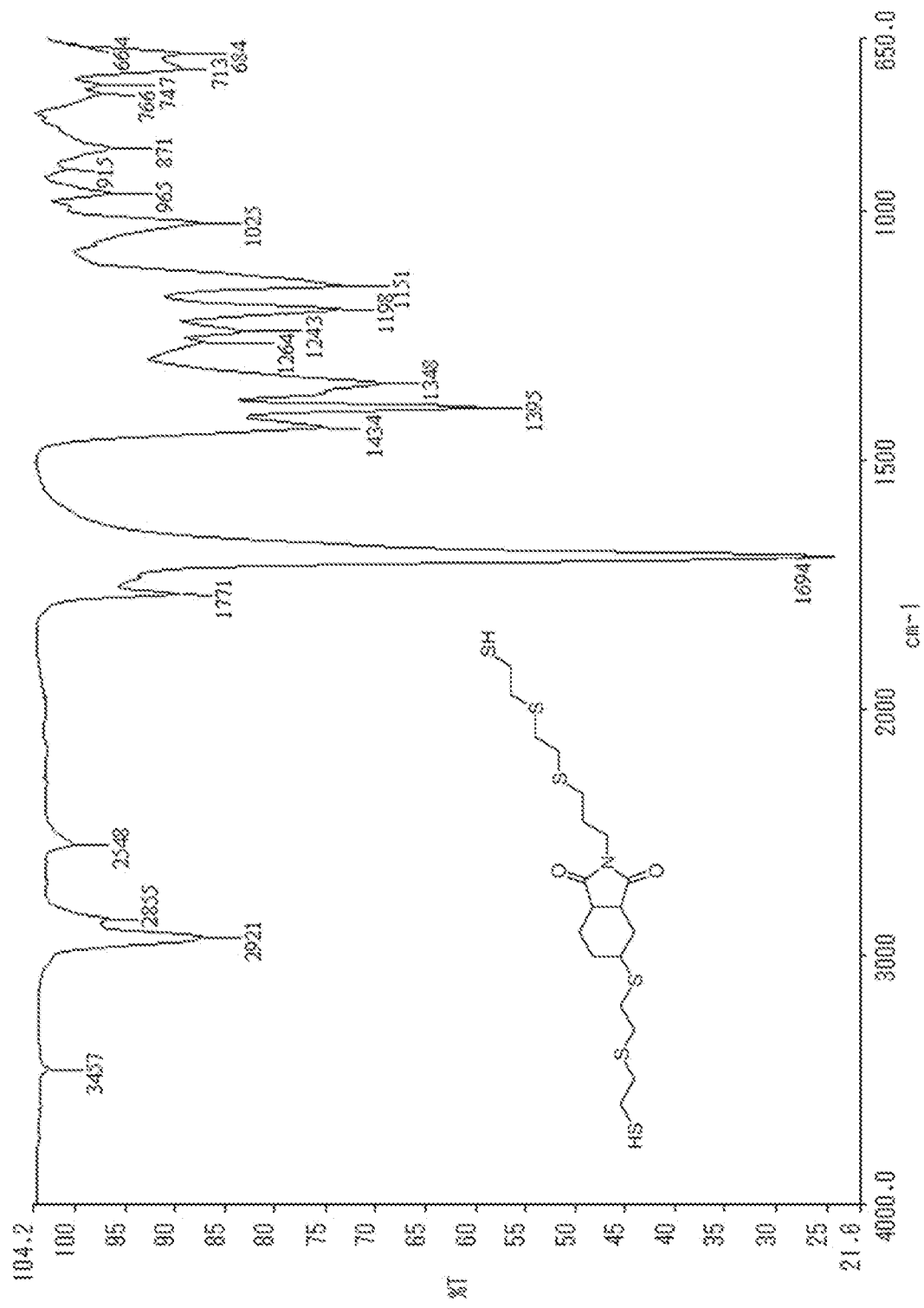
FIG. 9 is an IR spectral chart of a yellow liquid obtained in Example 9.

IR spectral data of the yellow liquid was as shown in the chart of FIG. 9.

It was identified from these spectral data that the yellow liquid obtained was the target thiol compound represented by the chemical formula (I-88) (thiol equivalent: 275.0).

[Chem. 58]

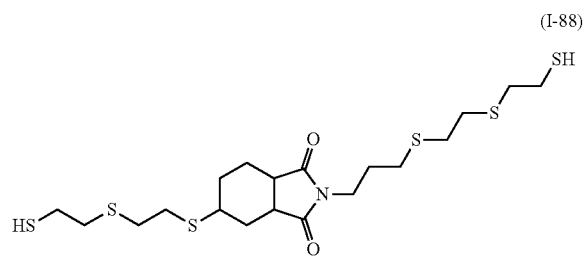

(I-88)

[Chem. 57]

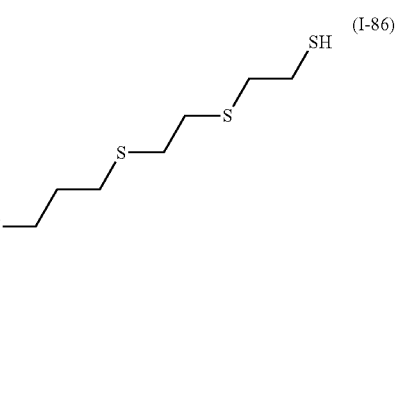

(I-86)

Example 9

Synthesis of Adduct of N-allyl-tetrahydrophthalimide and 3-thiapentane-1,5-dithiol In a four-necked eggplant flask having a volume of 500 ml were charged 28.68 g (150.0 mmol) of N-allyl-tetrahydrophthalimide, 115.74 g (750.0 mmol) of 3-thiapentane-1,5-dithiol, 0.36 g (1.5 mmol) of benzoyl peroxide, and 200.00 g of toluene, followed by stirring at 100° C. for 48 hours.

The reaction mixture obtained was concentrated and purified by a silica gel column chromatography (hexane/chloroform=1/9 (v/v)), to thereby obtain 52.49 g of a yellow liquid (yield: 70.0%).

$^1$H-NMR spectral data of the yellow liquid was as follows.

Example 10

Synthesis of Adduct of 4-(4-vinylbenzyloxy)allylbenzene and 3-thiapentane-1,5-dithiol In a four-necked eggplant flask having a volume of 500 ml were charged 37.55 g (150.0 mmol) of 4-(4-vinylbenzyloxy)allylbenzene, 115.74 g (750.0 mmol) of 3-thiapentane-1,5-dithiol, 0.36 g (1.5 mmol) of benzoyl peroxide, and 200.00 g of toluene, followed by stirring at 100° C. for 48 hours. The reaction mixture obtained was concentrated and purified by a silica gel column chromatography (hexane/chloroform=1/9 (v/v)), to thereby obtain 61.46 g of a yellow liquid (yield: 73.3%).

$^1$H-NMR spectral data of the yellow liquid was as follows.

$^1$H-NMR (d$_6$-DMSO) δ: 7.39 (d, 2H), 7.30-7.27 (m, 2H), 7.06-7.01 (m, 2H), 7.03 (t, 1H), 6.88 (t, 1H), 5.08 (s, 2H), 2.83-2.80 (m, 4H), 2.75-2.58 (m, 20H), 2.48 (quin, 2H), 1.10 (d, 2H).

Figure 10:
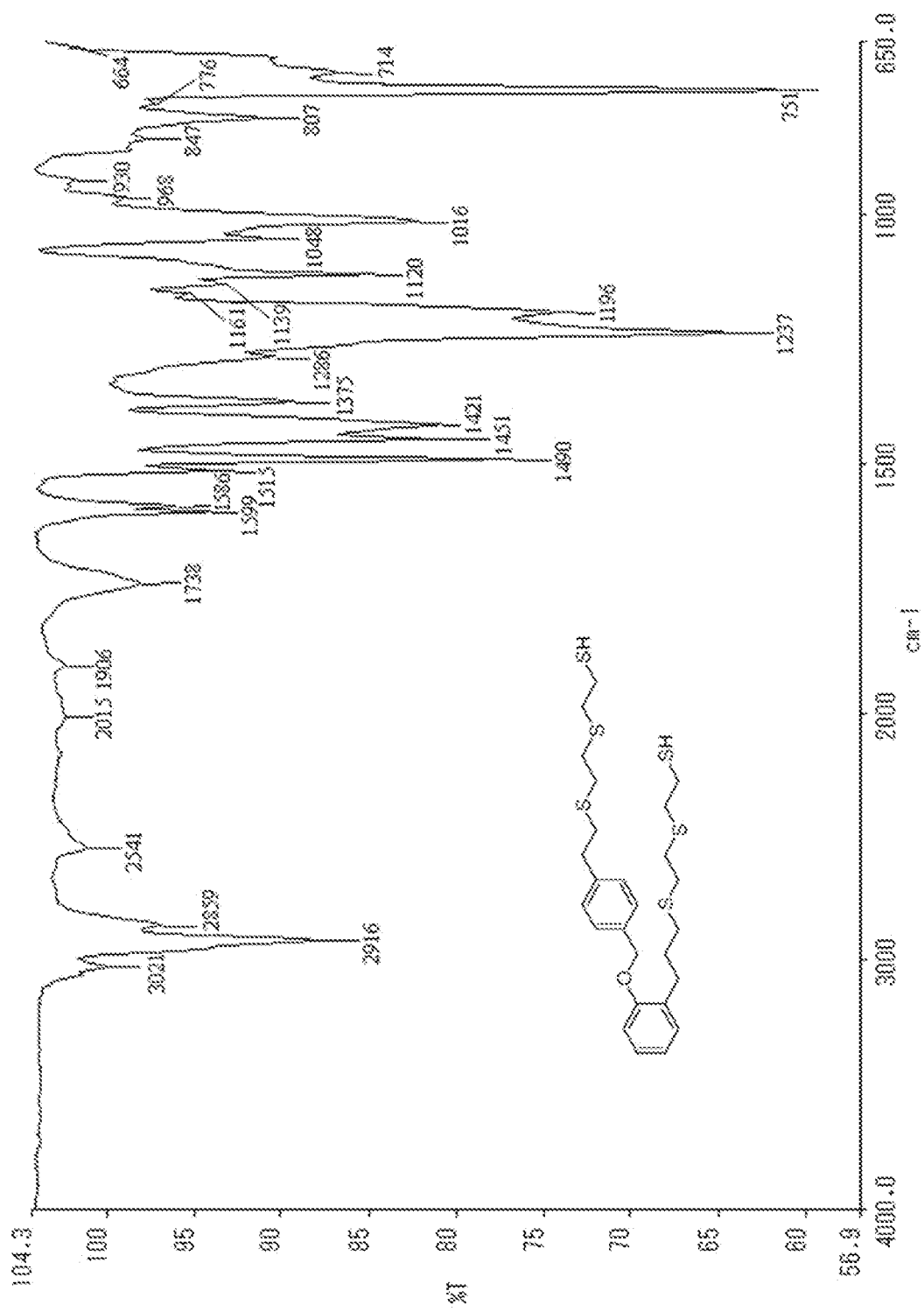
FIG. 10 is an IR spectral chart of a yellow liquid obtained in Example 10.

IR spectral data of the yellow liquid was as shown in the chart of FIG. 10.

It was identified from these spectral data that the yellow liquid obtained was the thiol compound represented by the chemical formula (I-77) (thiol equivalent: 297.8).

[Chem. 59]

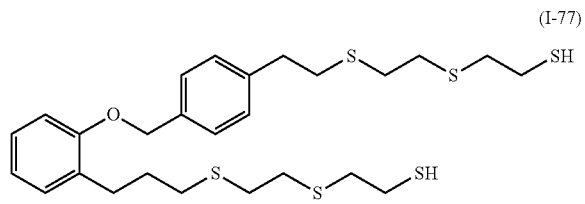

(I-77)

Example 11

An epoxy resin composition was prepared by mixing 80.0 parts by weight of the thiol compound synthesized in Example 1 and 20.0 parts by weight of TS-G as curing agents, and 0.8 parts by weight of dimethylbenzylamine as a curing accelerator, and 83.0 parts by weight of jER828 as an epoxy compound.

The amount of the curing accelerator used was adjusted such that the gelation time (80° C.) of the epoxy resin composition was 2 minutes±20 seconds.

Evaluation tests (measurement of the storage modulus of the cured product and measurement of the adhesive strength when used as an adhesive) were performed on this epoxy resin composition. The obtained test results were shown in Table 1.

Examples 12 to 19, and Comparative Example 1

Epoxy resin compositions having compositions shown in Table 1 were prepared in the same manner as in Example 11, and the epoxy resin compositions were subjected to the evaluation tests. The test results obtained are shown in Table 1.

Although the present invention has been described in detail by using specific embodiments, it will be apparent to those skilled in the art that various modifications and variations are possible without departing from the spirit and scope of the present invention. The present application is based on a Japanese Patent Application (Japanese Patent Application No. 2019-000860) filed on Jan. 7, 2019, contents of which are incorporated herein by reference.

INDUSTRIAL APPLICABILITY

The thiol compound of the present invention is expected to be used as a curing agent for resins and also expected to be used as an intermediate raw material of various sulfur-containing compounds.

In addition, the resin composition containing the thiol compound of the present invention is expected to be used for various purposes such as adhesion, sealing, encapsulation, casting, molding, painting and coating, and thus the present invention has great industrial applicability.

The invention claimed is:

1. A thiol compound represented by the chemical formula (I):

Y-A-Y　　(I)

in the chemical formula (I),

A represents a divalent group represented by any one of the chemical formula (A-1) to the chemical formula (A-23), and Y's each represent a group represented by the chemical formula (Y),

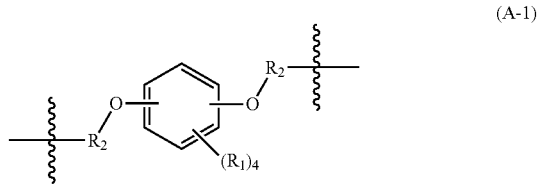

(A-1)

TABLE 1

| | | Example | | | | | | | | | Comparative Example |
|---|---|---|---|---|---|---|---|---|---|---|---|
| | | 11 | 12 | 13 | 14 | 15 | 16 | 17 | 18 | 19 | 1 |
| (A) Curing agent | Thiol compound of the present invention (note) | 80.0 | 80.0 | 80.0 | 80.0 | 80.0 | 80.0 | 80.0 | 80.0 | 80.0 | |
| | TS-G | 20.0 | 20.0 | 20.0 | 20.0 | 20.0 | 20.0 | 20.0 | 20.0 | 20.0 | |
| | PEMP | | | | | | | | | | 100.0 |
| (B) Curing accelerator | Dimethylbenzylamine | 0.8 | 0.8 | 0.7 | 0.6 | 0.2 | 2.0 | 0.8 | 1.0 | 1.4 | 7.7 |
| (C) Epoxy compound | jER828 | 83.0 | 86.0 | 75.0 | 65.0 | 92.0 | 80.0 | 69.0 | 78.0 | 72.9 | 153.0 |
| Storage modulus E' (GPa) | | 0.02 | 0.02 | 0.30 | 0.32 | 0.02 | 0.01 | 0.46 | 0.07 | 0.17 | 0.10 |
| Tensile shear adhesive strength (MPa) | Before PCT | 6.90 | 6.89 | 11.71 | 7.24 | 5.83 | 6.11 | 14.42 | 11.06 | 10.24 | 14.20 |
| | After PCT | 5.77 | 2.92 | 5.75 | 4.86 | 3.24 | 4.04 | 7.54 | 6.30 | 7.59 | N.D. |
| | Strength residual ratio (%) | 83.6 | 42.4 | 49.1 | 67.1 | 55.6 | 66.1 | 52.3 | 57.0 | 74.1 | N.D. |

(note):
the thiol compounds of the present invention used in Examples 11 to 19 are the thiol compounds synthesized in Examples 1 to 7 and the thiol compounds synthesized in Examples 9 and 10, respectively.

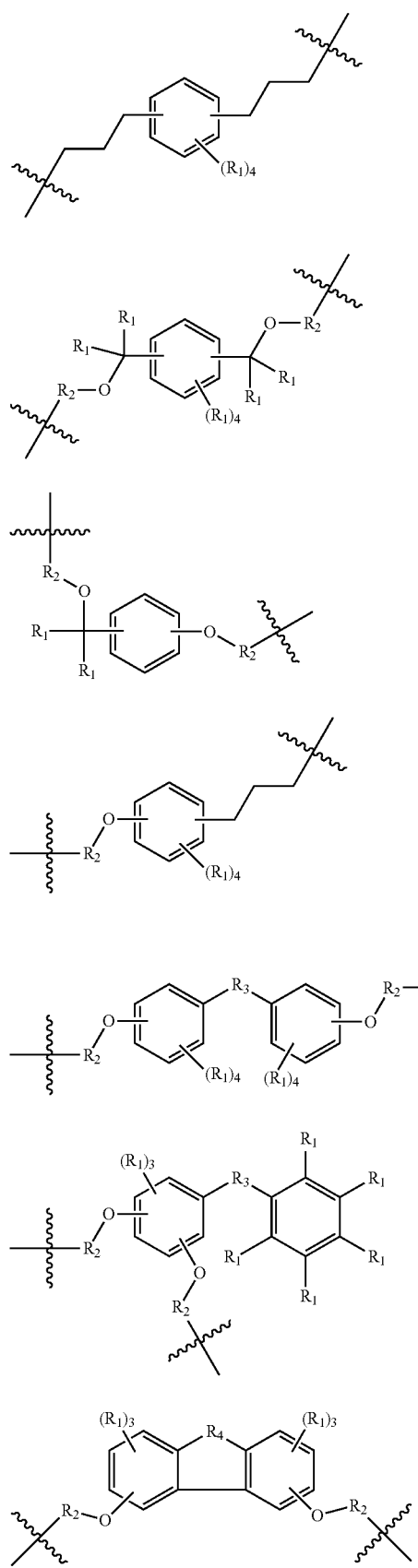
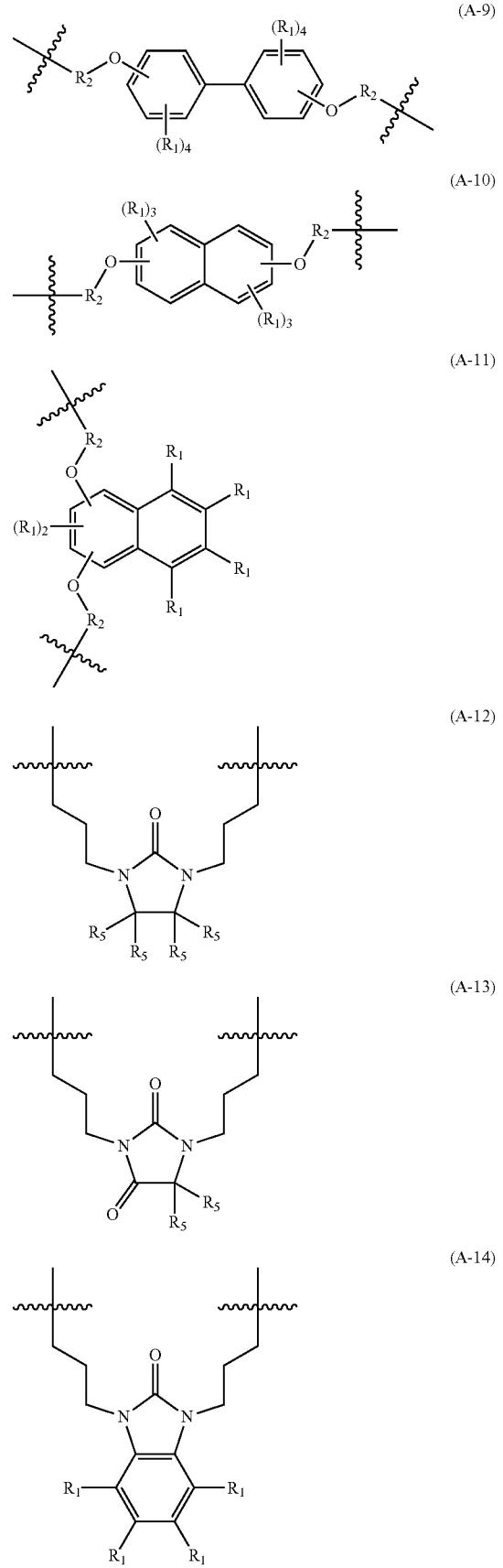

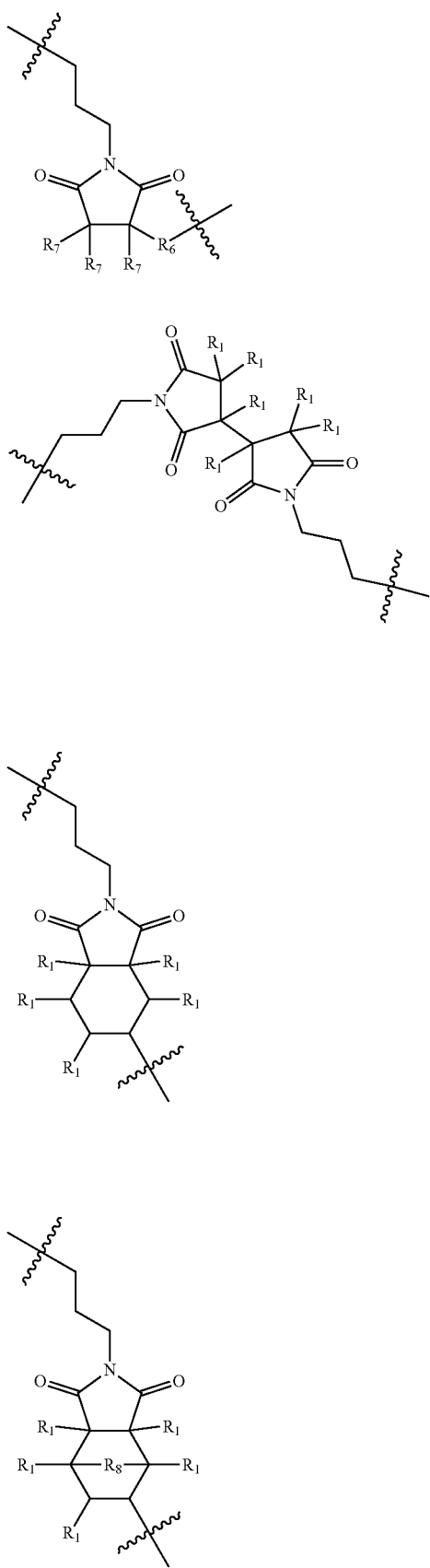
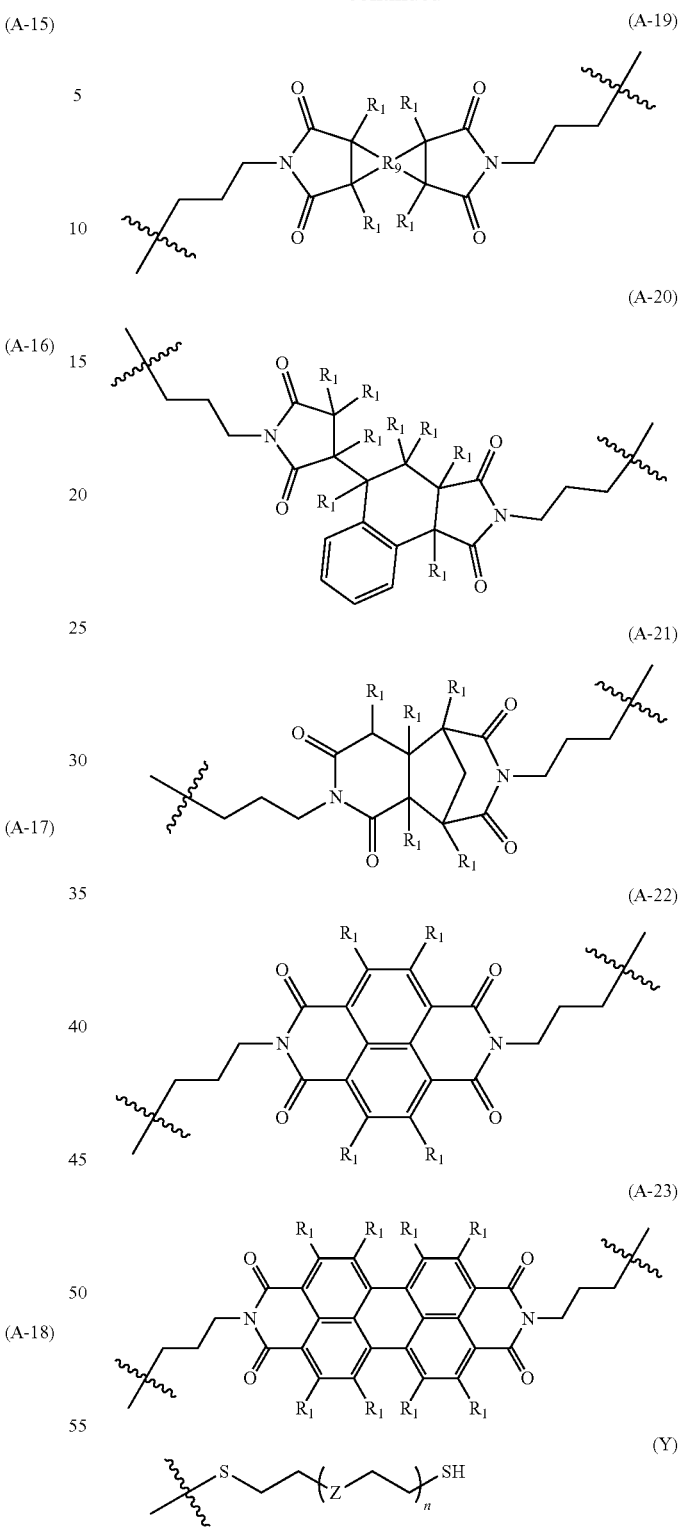
in the chemical formula (A-1) to the chemical formula (A-23),
$R_1$'s are the same as or different from each other and each represent a hydrogen atom, a linear, branched or cyclic alkyl group or alkoxy group having 1 to 10 carbon atoms, or an aryl group, $R_2$'s are the same as or different from each other and each represent a divalent group represented by any one of the chemical formula (R2-1) to the chemical formula (R2-4), $R_3$ represents a divalent group represented by any one of the chemical formula (R3-1) to the chemical formula (R3-12), $R_4$ represents a divalent group represented by any one of the chemical formula (R3-1) to the chemical formula (R3-4), the chemical formula (R3-6) or any one of the chemical formula (R3-8) to the chemical formula (R3-12), $R_5$'s are the same as or different from each other and each represent a hydrogen atom, a linear, branched or cyclic alkyl group having 1 to 10 carbon atoms, $R_6$ represents an atomic bonding, or a divalent group represented by the chemical formula (R3-1) or any one of the chemical formula (R6-1) to the chemical formula (R6-6), $R_7$'s are the same as or different from each other and each represent a hydrogen atom, a linear, branched or cyclic alkyl group having 1 to 10 carbon atoms, or an aryl group, $R_7$'s may be linked to each other to form a ring, $R_8$ represents a divalent group represented by the chemical formula (R3-1), the chemical formula (R3-10) or the chemical formula (R8-1), and $R_9$ represents a tetravalent group represented by any one of the chemical formula (R9-1) to the chemical formula (R9-15);

in the chemical formula (Y),

Z's represent the same as or different from each other, and each represent an oxygen atom or a sulfur atom, and n represents an integer of 1 to 3; and the wavy line portions in the chemical formula (A-1) to the chemical formula (A-23) and the chemical formula (Y) each represent an atomic bonding,

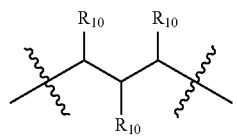

(R2-1)

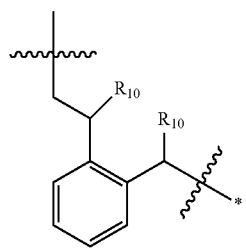

(R2-2)

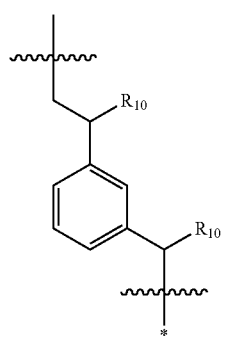

(R2-3)

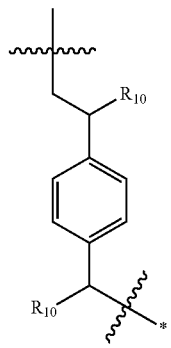

(R2-4)

in the chemical formula (R2-1) to the chemical formula (R2-4), $R_{10}$'s are the same as or different from each other and each represent a hydrogen atom or a methyl group, the wavy line portions each represent an atomic bonding, and those with * (asterisk) each represent a bond to an oxygen atom,

(R3-1)

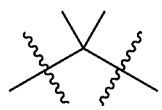

(R3-2)

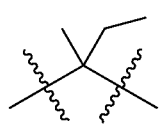

(R3-3)

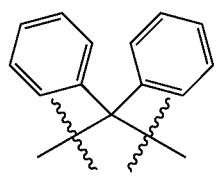

(R3-4)

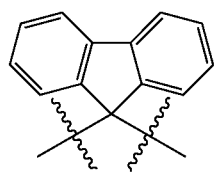

(R3-5)

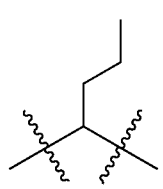

(R3-6)

(R3-7) 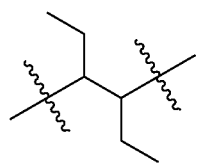

(R3-8) 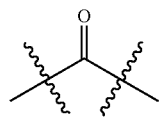

(R3-9) 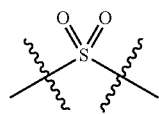

(R3-10) 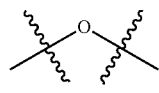

(R3-11) 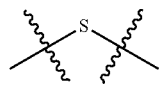

(R3-12) 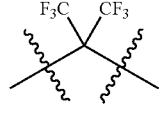

in the chemical formula (R3-1) to the chemical formula (R3-12), the wavy line portions each represent an atomic bonding, (R6-1) 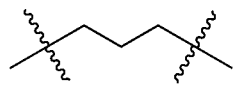

(R6-2) 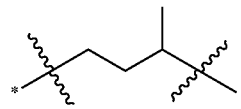

(R6-3) 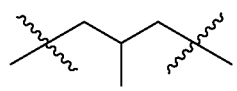

(R6-4) 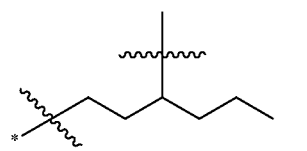

(R6-5) 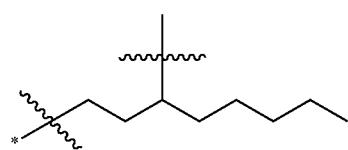

(R6-6) 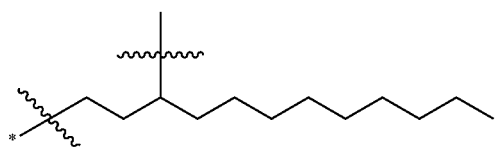

in the chemical formula (R6-1) to the chemical formula (R6-6), the wavy line portions each represent an atomic bonding, and those with * (asterisk) each represent a bond to an imide ring), (R8-1) 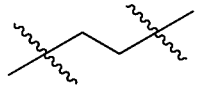

in the chemical formula (R8-1), the wavy line portions each represent an atomic bonding, and (R9-1) 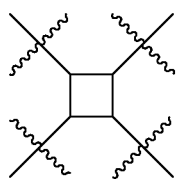

(R9-2) 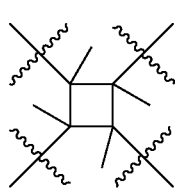

(R9-3) 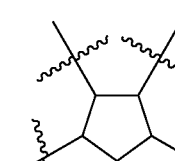

(R9-4) 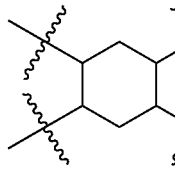

(R9-5) 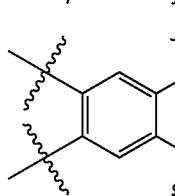

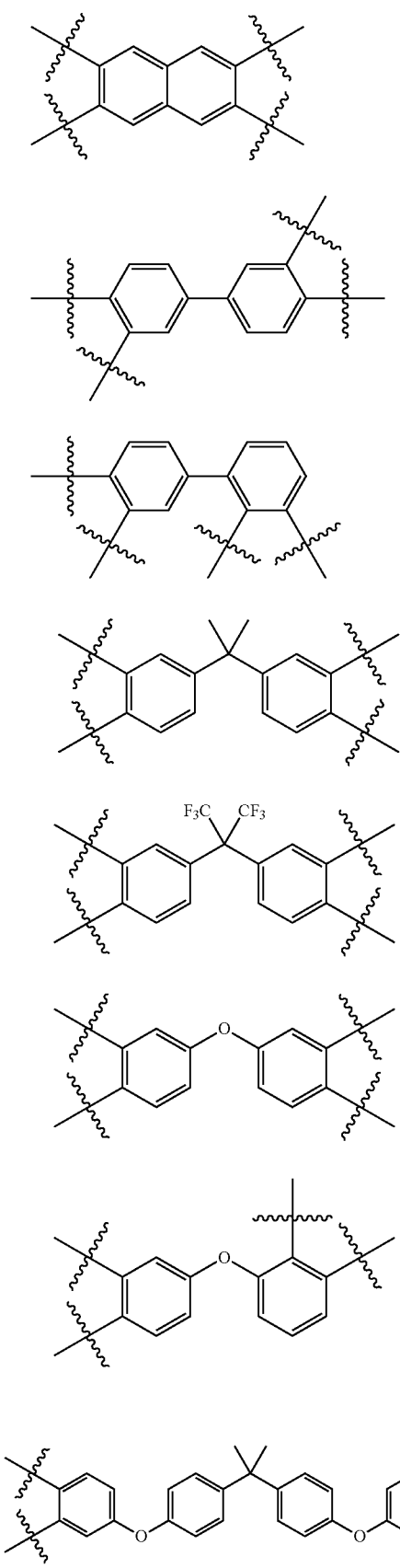

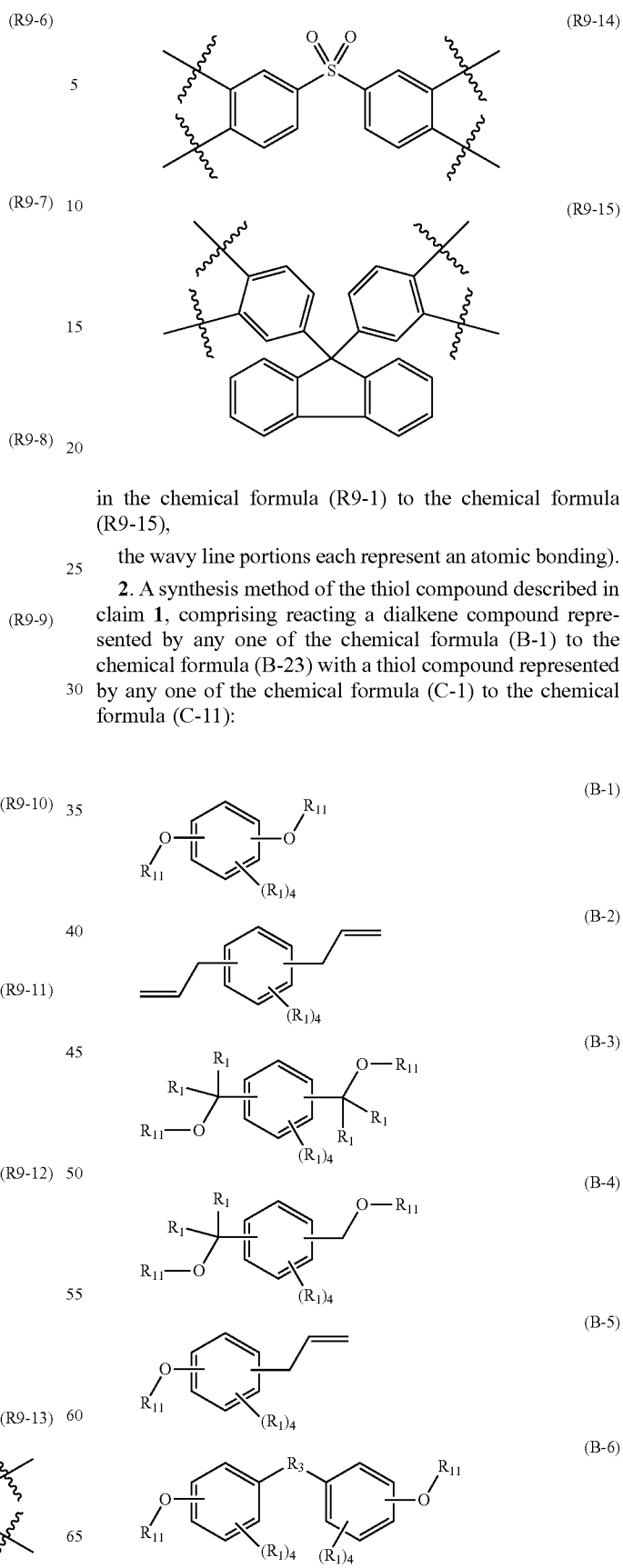

in the chemical formula (R9-1) to the chemical formula (R9-15), the wavy line portions each represent an atomic bonding).

2. A synthesis method of the thiol compound described in claim 1, comprising reacting a dialkene compound represented by any one of the chemical formula (B-1) to the chemical formula (B-23) with a thiol compound represented by any one of the chemical formula (C-1) to the chemical formula (C-11):

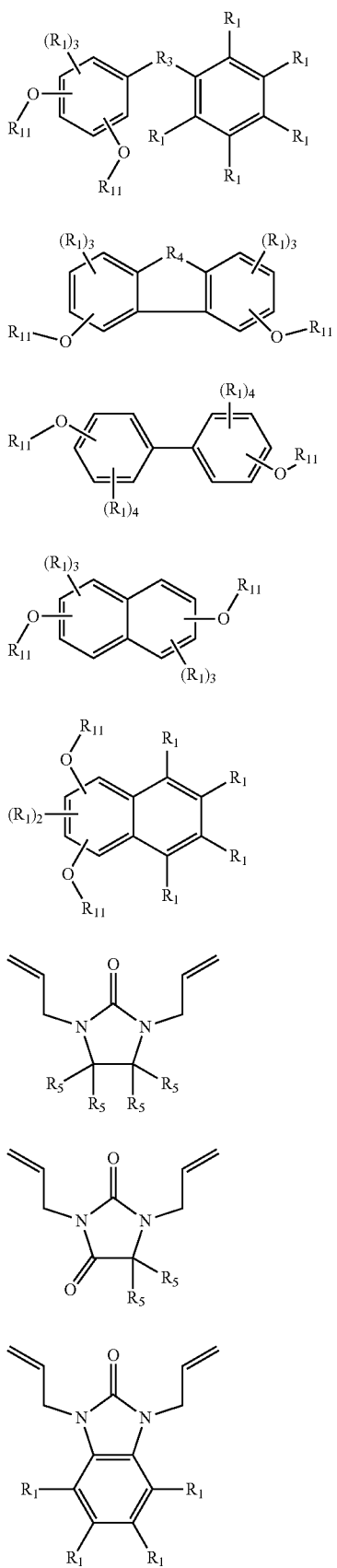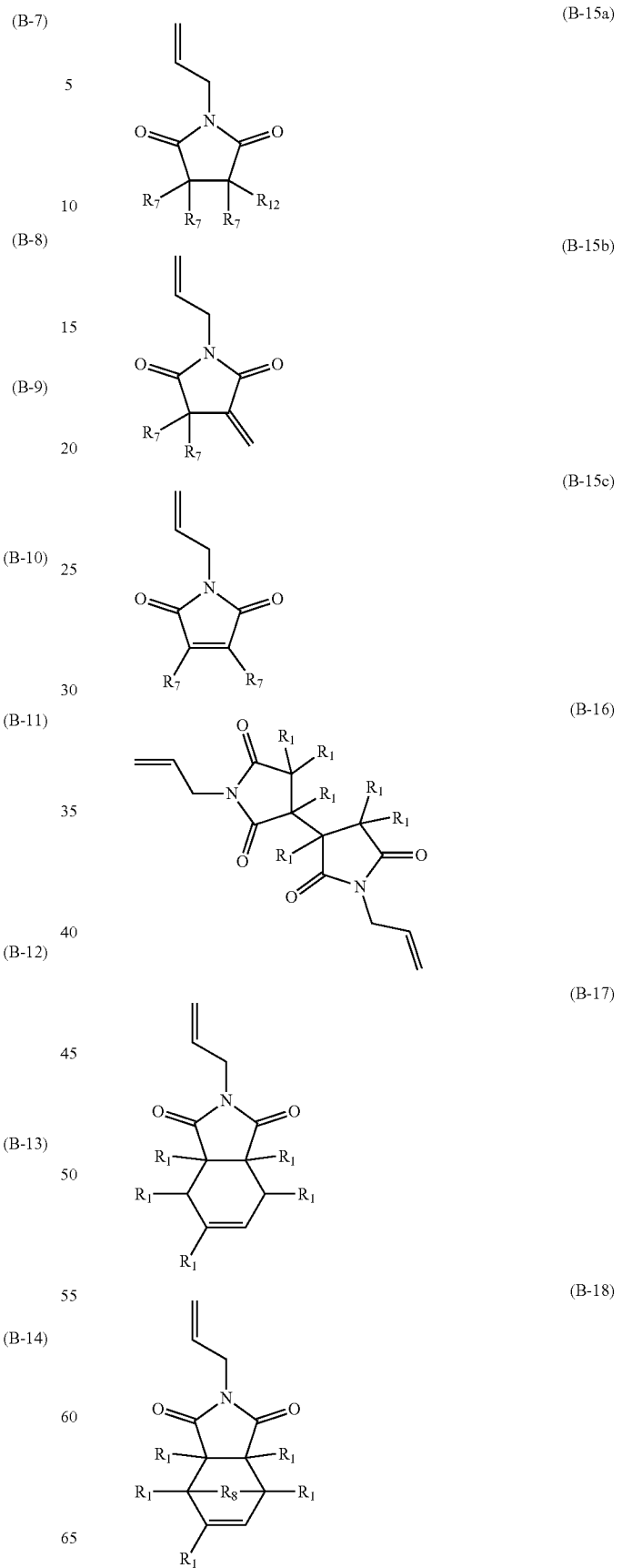

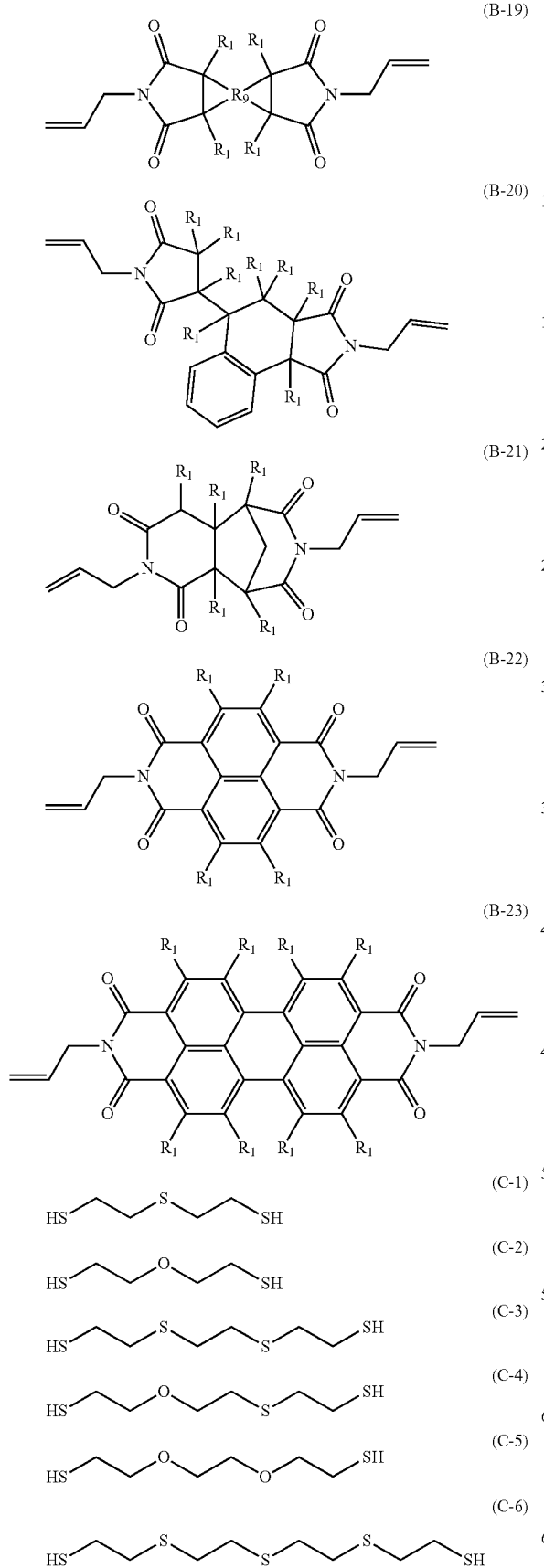
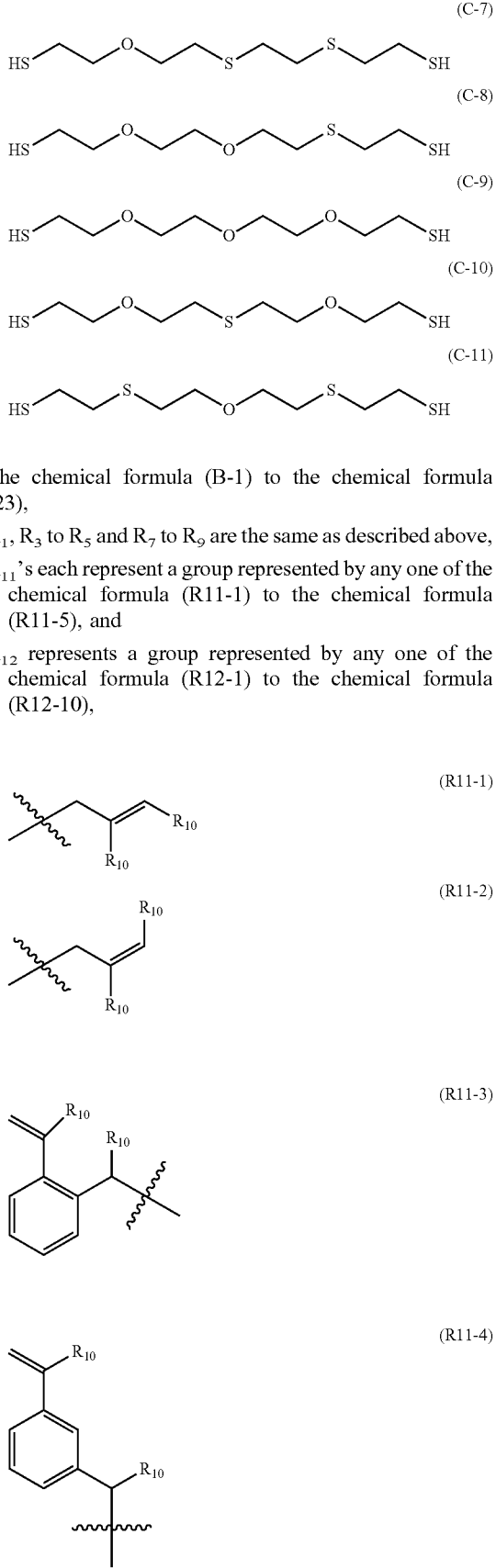
in the chemical formula (B-1) to the chemical formula (B-23),
$R_1$, $R_3$ to $R_5$ and $R_7$ to $R_9$ are the same as described above,
$R_{11}$'s each represent a group represented by any one of the chemical formula (R11-1) to the chemical formula (R11-5), and
$R_{12}$ represents a group represented by any one of the chemical formula (R12-1) to the chemical formula (R12-10), (R11-5)

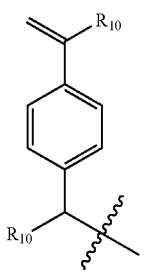

in the chemical formula (R11-1) to the chemical formula (R11-5), $R_{10}$'s each are the same as described above, and the wavy line portions each represent an atomic bonding, (R12-1)
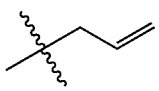

(R12-2)
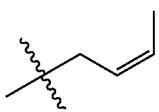

(R12-3)
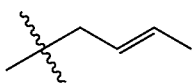

(R12-4)
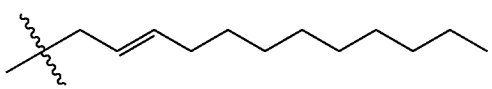

(R12-5)
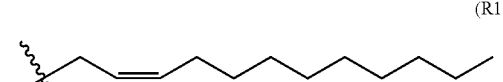

(R12-6)
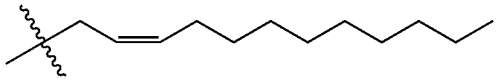

(R12-7)

(R12-8)
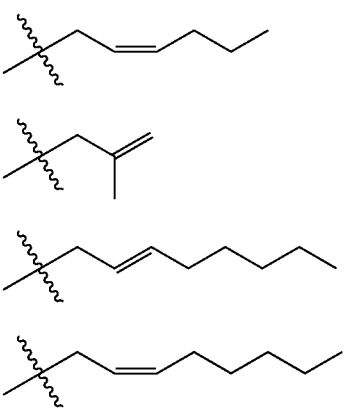

(R12-9)
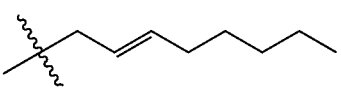

(R12-10)
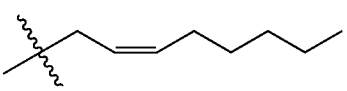

in the chemical formula (R12-1) to the chemical formula (R12-10), the wavy line portions each represent an atomic bonding).

3. A curing agent comprising the thiol compound described in claim 1.

4. A resin composition comprising the thiol compound described in claim 1, and an epoxy compound.

5. The resin composition according to claim 4, further comprising an amine as a curing accelerator.

6. The resin composition according to claim 4, further comprising, as a curing accelerator, a reaction product between an epoxy compound and an amine.

7. The resin composition according to claim 4, further comprising, as a curing accelerator, a reaction product between a compound having one or more isocyanate groups in a molecule and a compound having at least any of a primary amino group and a secondary amino group in a molecule.

8. An adhesive comprising the resin composition described in claim 4.

9. A sealant comprising the resin composition described in claim 4.

10. A resin composition comprising the thiol compound described in claim 1, and an enic compound having a carbon-carbon double bond in a molecule.

11. An adhesive comprising the resin composition described in claim 10.

12. A sealant comprising the resin composition described in claim 10.

* * * * *